US011100640B2

(12) United States Patent
Smith

(10) Patent No.: US 11,100,640 B2
(45) Date of Patent: Aug. 24, 2021

(54) SYSTEMS AND METHODS FOR LESION ANALYSIS

(71) Applicant: AI METRICS, LLC, Hoover, AL (US)

(72) Inventor: Andrew Dennis Smith, Hoover, AL (US)

(73) Assignee: AI METRICS, LLC, Hoover, AL (US)

(*) Notice: Subject to any disclaimer, the term of this patent is extended or adjusted under 35 U.S.C. 154(b) by 0 days.

(21) Appl. No.: 17/106,927

(22) Filed: Nov. 30, 2020

(65) Prior Publication Data
US 2021/0166377 A1  Jun. 3, 2021

Related U.S. Application Data

(60) Provisional application No. 62/942,126, filed on Nov. 30, 2019.

(51) Int. Cl.
G06T 7/00 (2017.01)
G16H 10/60 (2018.01)
G06T 7/11 (2017.01)

(52) U.S. Cl.
CPC .............. G06T 7/0012 (2013.01); G06T 7/11 (2017.01); G16H 10/60 (2018.01); G06T 2207/20084 (2013.01); G06T 2207/30096 (2013.01)

(58) Field of Classification Search
None
See application file for complete search history.

(56) References Cited

U.S. PATENT DOCUMENTS

| 10,109,374 | B1* | 10/2018 | Givoly | G16H 50/70 |
| 10,743,829 | B2* | 8/2020 | Smith | G06T 7/0016 |
| 10,839,964 | B2* | 11/2020 | Ohad | G16H 70/00 |
| 2008/0130968 | A1 | 6/2008 | Daw et al. | |
| 2008/0292194 | A1 | 11/2008 | Schmidt et al. | |
| 2009/0180677 | A1 | 7/2009 | Li et al. | |
| 2010/0131873 | A1* | 5/2010 | Mejia | G16H 30/40 715/764 |
| 2011/0010192 | A1* | 1/2011 | Backhaus | G16H 40/67 705/2 |

(Continued)

FOREIGN PATENT DOCUMENTS

WO   WO-2015031296 A1 * 3/2015 ............. G16H 50/20

OTHER PUBLICATIONS

Abajian, Aaron C., Mia Levy, and Daniel L. Rubin. "Informatics in radiology: improving clinical work flow through an AIM database: a sample web-based lesion tracking application." Radiographics 32.5 (2012): 1543-1552. (Year: 2012).*

(Continued)

Primary Examiner — Samah A Beg
(74) Attorney, Agent, or Firm — Workman Nydegger

(57) ABSTRACT

A system for facilitating lesion analysis is configurable to identify a user profile associated with a user accessing the system. The user profile indicates a radiology specialty associated with the user. The system is also configurable to access a plurality of cross-sectional medical images associated with a particular patient and identify a subset of cross-sectional medical images from the plurality of cross-sectional medical images that correspond to the radiology specialty indicated by the user profile. The system is also configurable to present the subset of cross-sectional medical images to the user in navigable form.

22 Claims, 43 Drawing Sheets

(56) References Cited

U.S. PATENT DOCUMENTS

| | | | | |
|---|---|---|---|---|
| 2011/0029326 A1* | 2/2011 | Venon | ................... | G06Q 10/06 |
| | | | | 705/3 |
| 2014/0358585 A1* | 12/2014 | Reiner | ................... | G16H 80/00 |
| | | | | 705/3 |
| 2015/0045651 A1 | 2/2015 | Crainiceanu et al. | | |
| 2015/0205917 A1 | 7/2015 | Mabotuwana et al. | | |
| 2015/0235365 A1 | 8/2015 | Mankovich et al. | | |
| 2016/0364862 A1* | 12/2016 | Reicher | ................... | G06K 9/66 |
| 2017/0119334 A1* | 5/2017 | Smith | ................... | G06T 7/0016 |
| 2018/0060534 A1 | 3/2018 | Reicher et al. | | |
| 2018/0353148 A1* | 12/2018 | Smith | ................... | G06T 11/005 |
| 2019/0108635 A1 | 4/2019 | Hibbard et al. | | |
| 2020/0043600 A1* | 2/2020 | Glottmann | ............ | G06F 40/154 |
| 2020/0312428 A1* | 10/2020 | Reeves | ................... | G16H 10/60 |
| 2020/0337665 A1* | 10/2020 | Smith | ................... | A61B 6/5211 |

OTHER PUBLICATIONS

Folio, Les R., Laura B. Machado, and Andrew J. Dwyer. "Multimedia-enhanced radiology reports: concept, components, and challenges." RadioGraphics 38.2 (2018): 462-482. (Year: 2018).*

International Search Report and Written Opinion received for PCT Patent Application No. PCT/US20/62614, dated Mar. 4, 2021, 9 pages.

Eisenhauer, Elizabeth A., et al. "New response evaluation criteria in solid tumours: revised RECIST guideline (version 1.1)." European journal of cancer 45.2 (2009): 228-247. (Year: 2009).

* cited by examiner

FIG. 32

Findings

Target Lesions
- LN Axillary L
  3.8 x 2.5 cm
- LN Lower Paratrach
  2.5 x 1.8 cm
- LN Periportal
  6.6 x 4.0 cm
- LN Mesenteric
  4.4 x 3.6 cm
- LN External Iliac L
  5.3 x 3.6 cm
- LN Inguinal L
  3.3 x 2.3 cm

Non-Target Lesions
- LN Axillary Bilat
  Present / Pathologic
- LN Mediastinal Multiple
  Present / Pathologic
- LN Abd Multiple - Gast...
  Present / Pathologic
- LN Retroperit Multiple
  Present / Pathologic
- LN Mesenteric Multiple
  Present / Pathologic
- LN Pelvic Side Bilat
  Present / Pathologic
- LN Inguinal Bilat
  Present / Pathologic

Other Findings
- Abd Other -- Newly Identified - Hypervascular liver lesion

Slice 22 of 273

2002
2802
2806
2008

Slice 11 of 271
Review AI segmentation

Absent / Not Pathologic
Present / Pathologic
Unequivocal Progression
Not Evaluated 2804
3202
3208
3204
3206

Exit Autopilot

Target Lesions
LN Axillary L
LN Lower Paratrach     2808
LN Periportal
LN Mesenteric
LN External Iliac L
LN Inguinal L

Non-Target Lesions
LN Axillary Bilat
LN Mediastinal Multiple
LN Abd Multiple - Gast...
LN Retroperit Multiple
LN Mesenteric Multiple
LN Pelvic Side Bilat
LN Inguinal Bilat

New Sites of Disease +

Other Findings +
Abd Other -- Hypervascular liver lesion

Unlock Preview Scroll

Notes
Optional additional notes
(300 character maximum)

FIG. 33

Left panel:

- Exit Autopilot  ← 2804
- Target Lesions
  - LN Axillary L
  - LN Lower Paratrach
  - LN Periportal
  - LN Mesenteric
  - LN External Iliac L
  - LN Inguinal L
- Non-Target Lesions  ← 2808
  - LN Axillary Bilat
  - LN Mediastinal Multiple
  - LN Abd Multiple - Gast...
  - LN Retroperit Multiple
  - LN Mesenteric Multiple
  - LN Pelvic Side Bilat
  - LN Inguinal Bilat
- New Sites of Disease +
- Other Findings +
  - Abd Other - Hypervascular liver lesion
- Lock Preview Scroll
- Notes
  - Optional additional notes (300 character maximum)

Slice 106 of 271
Review AI segmentation
- Resolved
- Improved
- Unchanged
- Worsened
- Not Evaluated Labels on image: 3302, 3308, 3304, 3306

Right panel:

Slice 115 of 273
Labels on image: 2802, 2806, 2102, 2104

Findings
- Target Lesions
  - LN Axillary L  3.8 x 2.5 cm
  - LN Lower Paratrach  2.5 x 1.8 cm
  - LN Periportal  6.6 x 4.0 cm
  - LN Mesenteric  4.4 x 3.6 cm
  - LN External Iliac L  5.3 x 3.6 cm
  - LN Inguinal L  3.3 x 2.3 cm
- Non-Target Lesions
  - LN Axillary Bilat  Present / Pathologic
  - LN Mediastinal Multiple  Present / Pathologic
  - LN Abd Multiple - Gast...  Present / Pathologic
  - LN Retroperit Multiple  Present / Pathologic
  - LN Mesenteric Multiple  Present / Pathologic
  - LN Pelvic Side Bilat  Present / Pathologic
  - LN Inguinal Bilat  Present / Pathologic
- Other Findings
  - Abd Other -- Newly Identified - Hypervascular liver lesion

Oncologic Provider Report  3402

<sub>3410</sub>

Bar chart showing Target Lesion Length (cm) vs Study Date:
- 1/1/00: 17.8 cm Baseline Lowest
- 2/2/00: SD, 15.1 cm, -15.2% Lowest

| Criteria | Freeform RECIST |
|---|---|
| Response | Stable Disease (SD) |

| New Sites of Disease | No |
|---|---|

3404 — Target Lesions | Latest Metrics
- LN Axillary L — 3.0 x 1.7 cm
- LN Lower Paratrach — 2.6 x 1.6 cm
- LN Periportal — 7.0 x 3.7 cm
- LN Mesenteric — 4.0 x 3.1 cm
- LN External Iliac L — 4.6 x 3.2 cm
- LN Inguinal L — 2.8 x 1.8 cm 3406 — Non-Target Lesions | Response
- LN Axillary Bilat — Pathologic
- LN Mediastinal Multiple — Pathologic
- LN Abd Multiple
- Gastrohepatic — Pathologic
- LN Retroperit Multiple — Pathologic
- LN Mesenteric Multiple — Pathologic
- LN Pelvic Side Bilat — Pathologic
- LN Inguinal Bilat — Pathologic

3408

Summary
| Current Sum | 15.1 cm |
|---|---|
| % Change from Baseline | -15.2% |
| % Change from Lowest | N/A |
| % Change from Prior | -15.2% |

Other Findings
| Abd Other (Hypervascular liver lesion) | Unchanged |
|---|---|
| First Identified 1/1/00 | Needs Follow Up |

Reader
| Report Date | 2/2/00 |
|---|---|
| Report Status | Draft |

Notes

Detailed Results Report

3502

| Target Lesion | 1/1/00 | 2/2/00 |
|---|---|---|
| LN Axillary L<br>Lymph node | 3.8 x 2.5 cm | 3.0 x 1.7 cm |
| LN Lower Paratrach<br>Lymph node | 2.5 x 1.8 cm | 2.6 x 1.6 cm |
| LN Periportal<br>Lymph node | 6.6 x 4.0 cm | 7.0 x 3.7 cm |
| LN Mesenteric<br>Lymph node | 4.4 x 3.6 cm | 4.0 x 3.2 cm |
| LN External Iliac L<br>Lymph node | 5.3 x 3.6 cm | 4.6 x 3.2 cm |
| LN Inguinal L<br>Lymph node | 3.3 x 2.3 cm | 2.8 x 1.8 cm |
| Sum (cm) | 17.8 | 15.1 |
| % Change from Baseline | Baseline | -15.2% |
| % Change from Lowest | | Lowest |
| % Change from Prior | | -15.2% |

| Non-target Lesion | 1/1/00 | 2/2/00 |
|---|---|---|
| LN Axillary Bilat<br>Lymph node | Pathologic | Pathologic |
| LN Mediastinal Multiple<br>Lymph node | Pathologic | Pathologic |
| LN Abd Multiple<br>Lymph node | Pathologic | Pathologic |
| LN Retroperit Multiple<br>Lymph node | Pathologic | Pathologic |
| LN Mesenteric Multiple<br>Lymph node | Pathologic | Pathologic |
| LN Pelvic Side Bilat<br>Lymph node | Pathologic | Pathologic |

*FIG. 35*

SYSTEMS AND METHODS FOR LESION ANALYSIS

CROSS-REFERENCE TO RELATED APPLICATIONS

This application claims the benefit of and priority to U.S. Provisional Patent Application No. 62/942,126, filed Nov. 30, 2020 and entitled "SYSTEMS AND METHODS FOR LESION ANALYSIS." The foregoing application is incorporated herein by reference in its entirety.

BACKGROUND

Assessment of changes in tumor burden is an important feature for defining tumor response in clinical practice and clinical trials. Both tumor shrinkage and development of disease progression are important endpoints in clinical practice and clinical trials as these often determine objective response to treatment. In order to standardize tumor response assessment, various response criteria have been described, including Response Evaluation Criteria in Solid Tumors (RECIST) version 1.0 or more commonly version 1.1, modified RECIST (mRECIST), World Health Organization (WHO) Criteria, Choi Criteria, Vascular Tumor Burden (VTB) Criteria, Morphology Attenuation Size and Structure (MASS) Criteria, immune-related Response Criteria (irRC), immune-related RECIST (irRECIST), Cheson Criteria, Lugano Classification lymphoma response criteria, International Working Group consensus response evaluation criteria in lymphoma (RECIL), Positron Emission Tomography Response Criteria in Solid Tumors (PERCIST), European Organization for Research and Treatment of Cancer (EORTC) Response Criteria, Prostate Cancer Working Group 3 (PCWG3) criteria, Response Assessment in Neuro-Oncology (RANO) Criteria, immune RANO (iRANO), International Myeloma Working Group (IMWG) consensus criteria, etc.

In order to assess objective response, an estimate of the overall tumor burden at baseline is needed and used as a comparator for subsequent measurements. Each tumor response criteria specifies parameters that define a measurable lesion at baseline. For example, RECIST 1.1 defines a non-nodal lesion as measurable if it measures ≥1.0 cm in long axis at baseline and defines a lymph node as measurable if it measures ≥1.5 cm in short axis at baseline. When one or more measurable lesions are present at baseline, each tumor response criteria specifies which lesions should be considered as target lesions. Target lesions are typically selected based on being the largest in size or most metabolically active but also should lend themselves to reproducible repeated measurements. Most tumor response criteria limit the number of total target lesions and limit the number of target lesions per organ. For example, RECIST 1.1. limits the total number of target lesions to 5 and the total number of target lesions per organ to 2. Each tumor response criteria specifies how the target lesions should be measured. For example, RECIST 1.1 states that non-nodal lesions should be measured in the longest dimension on axial cross-sectional images, while lymph nodes should be measured in short axis on axial cross-sectional images. The total tumor burden is then a mathematical calculation made from the individual target lesions. For example, the sum of the diameters (longest for non-nodal lesions, short axis for nodal lesions) for all target lesions is calculated and reported as the baseline sum diameters per RECIST 1.1.

The baseline measurements are used as a reference to characterize objective tumor regression or progression in the measurable dimension of the disease. All other lesions (or sites of disease) are identified as non-target lesions. The site of disease of all non-target lesions should be recorded at baseline. At subsequent time points, measurement of non-target lesions is not required, and these lesions are typically followed and defined as 'complete response' (CR), 'unequivocal progressive disease' (PD), 'non-CR/non-PD', or 'not evaluable' (NE). Alternatively, the non-target lesions could be qualitatively evaluated, such as 'present', 'absent', 'larger', or 'smaller'.

While most tumor response criteria utilize measured changes in target lesion length or size as a means of defining objective response, some criteria (e.g., Lugano, PERCIST and EORTC Response Criteria) utilize measured changes in target lesions radiotracer activity as a means of defining objective response, and other criteria use a combination of both. Different tumor response criteria may utilize different metrics, mathematical calculations, or cut points to define objective response, and computer implemented methods that automate one or more processes or method acts and/or ensure user compliance with one or more criteria may be used to reduce errors and improve efficiency in tumor response assessment.

A critical component of any tumor response criteria is the choice of target lesions on the baseline exam. In clinical practice and clinical trials, the choice of target lesions is at the discretion of the physician reviewer, which could be a radiologist, oncologist, radiation oncologist, surgeon, etc. Most tumor response criteria provide guidance on target lesion selection. For example, RECIST 1.1 provides guidance on which lesions are measurable or non-measurable and then provides additional details on how to select target lesions. In general target lesions and lymph nodes are selected based on their size, though the target lesions must be representative of all involved organs and should lend themselves to reproducible repeated measurements. Furthermore, tracking of target lesions over time is advantageous for obtaining accurate and precise objective response.

Conventional methods for tracking lesions (e.g., target lesions and/or non-target lesions) include navigating to an appropriate cross-sectional image, identifying a lesion for analysis, and recording the size of the lesion, the organ location in which the lesion resides, and the image number or slice position of the cross-sectional image depicting the identified lesion.

Existing processes for tracking/analyzing lesions suffer from a number of shortcomings. For example, manually outlining or tracing identified lesions to determine lesion size is a time-consuming process and is subject to variation due to different approaches taken by different physician reviewers. Furthermore, upon identifying an appropriate lesion for analysis and determining the size thereof, a reviewing physician often manually records the organ location in which the lesion resides and the image number or slice position in which the lesion is depicted.

To track lesions over time, a reviewing physician typically navigates through cross-sectional images captured at a later timepoint to find an image that depicts the same lesion analyzed previously. The reviewing physician then repeats the processes of determining the size of the lesion and recording the organ location, often also recording image number or slice position with or without the series number or name. Often, an additional step of preparing a report for oncological or patient review must be performed by the reviewing physician or another entity.

Thus, conventional processes for tracking and/or reporting on lesion progression over time can be laborious and/or time-intensive, particularly where numerous lesions were analyzed at the previous timepoint. Because of the mundane nature of these processes, reviewing physicians often become prone to dictation error when analyzing lesions, such as when recording lesion size, organ location, and/or image number or slice position.

Furthermore, tumor response analysis may be performed independently by different physicians focusing on different portions of a patient's body. Facilitating coordinated tumor response analysis by different physicians and generating composite reports at that include analysis from different specialists is associated with several challenges.

There is a need for a method and/or system for determining and/or reporting an objective tumor response using cross-sectional medical images in a manner that improves reviewer speed, efficiency, and/or accuracy.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments are directed to systems and methods for lesion analysis. In some implementations, a system for facilitating lesion analysis is configurable to identify a user profile associated with a user accessing the system. The user profile indicates a radiology specialty associated with the user. The system is also configurable to access a plurality of cross-sectional medical images associated with a particular patient and identify a subset of cross-sectional medical images from the plurality of cross-sectional medical images that correspond to the radiology specialty indicated by the user profile. The system is also configurable to present the subset of cross-sectional medical images to the user in navigable form.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which:

FIG. 32 illustrates an example of a display interface rendering associated with a system for facilitating lesion analysis as the system determines a lesion marker for a matching non-target lesion that corresponds to a previously analyzed non-target lesion, according to the present disclosure;

FIG. 33 illustrates an example of a display interface rendering associated with a system for facilitating lesion analysis as the system determines a lesion marker for a matching lesion that is not a target lesion or a non-target lesion and that corresponds to a previously analyzed lesion that was not a target lesion or a non-target lesion, according to the present disclosure;

FIG. 34 illustrates an example of a display interface rendering associated with a system for facilitating lesion analysis as the system provides a summary report based on one or more lesions analyzed at different timepoints, according to the present disclosure;

FIG. 35 illustrates an example of a display interface rendering associated with a system for facilitating lesion analysis as the system provides a detailed table report based on one or more lesions analyzed at different timepoints, according to the present disclosure;

DETAILED DESCRIPTION

Figure 1:
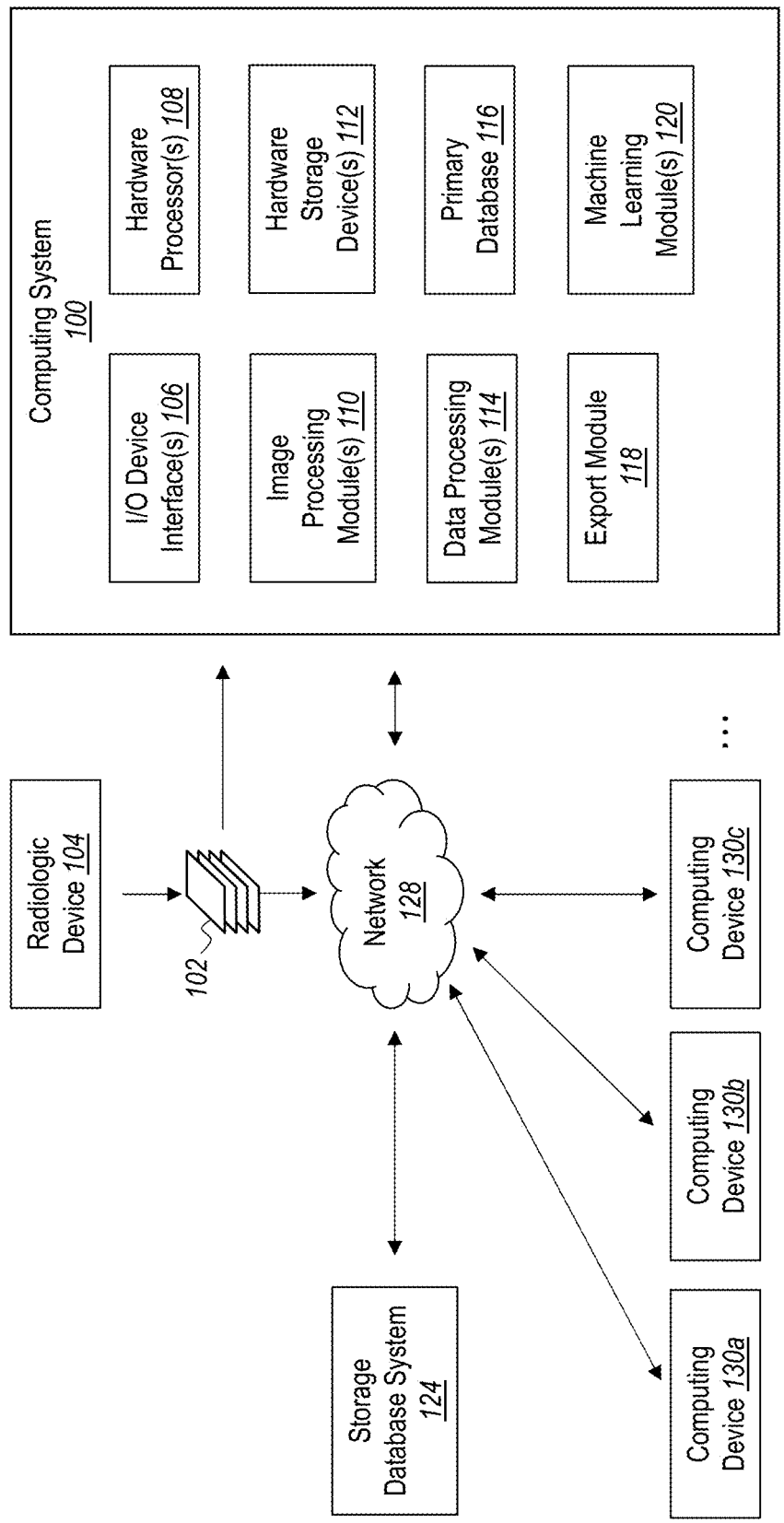
FIG. 1 illustrates a schematic representation of a system for facilitating lesion analysis using one or more cross-sectional images, according to the present disclosure.

While the detailed description may be separated into sections, the contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, modules, devices, methods, and/or terminology.

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Disclosed embodiments are directed to systems and methods for lesion analysis. In one embodiment, a system for lesion analysis is configurable to perform various acts. In some embodiments, the acts include presenting a cross-sectional medical image to a user on a display, receiving user input directed to a pixel region corresponding to a lesion represented in the cross-sectional medical image, identifying a predicted shape of the lesion represented in the cross-sectional medical image based on contrast between the pixel region corresponding to the lesion and a surrounding pixel region, automatically determining location information for the lesion based on the predicted shape of the lesion, and associating the location information for the lesion with the lesion represented in the cross-sectional medical image or with the cross-sectional medical image.

In some embodiments, the acts include identifying a user profile associated with a user accessing the system. The user profile indicates a radiology specialty associated with the user. The acts also include accessing a plurality of cross-sectional medical images associated with a particular patient and identifying a subset of cross-sectional medical images from the plurality of cross-sectional medical images that correspond to the radiology specialty indicated by the user profile. The acts also include presenting the subset of cross-sectional medical images to the user in navigable form.

In some embodiments, the acts include identifying a user profile associated with a user accessing the system. The user profile indicates system interaction preferences for the user. The system interaction preferences for the user include an interaction presentation. The acts further include accessing a plurality of cross-sectional medical images, displaying the plurality of cross-sectional medical images to the user in navigable form within a user interface, and identifying a plurality of controls within the user interface. The plurality of controls includes controls for: selecting a position within a pixel region corresponding to a lesion represented in the cross-sectional medical images, tracing the pixel region associated with the lesion represented in the cross-sectional medical images, and selecting location information for the lesion. The acts further include associating at least one the plurality of controls with the interaction presentation indicated in the system interaction preferences of the user profile, detecting user input operating the at least one of the plurality of controls, and presenting the interaction presentation.

In some embodiments, the acts include accessing a first database comprising one or more entries including location information associated with one or more lesions represented in one or more cross-sectional medical images from a first plurality of cross-sectional medical images of a patient and displaying representations of each of the one or more entries. The acts also include receiving user input selecting a particular entry of the one or more entries. The particular entry is selected by either a user selection of the representation of the particular entry or a user selection of a control for navigating to a next entry (where the particular entry is the next entry). The acts further include presenting the cross-sectional medical image and the lesion represented therein associated with the particular entry selected by the received user input and rendering a lesion marker associated with the particular entry overlaid on lesion represented in the cross-sectional medical image corresponding to the particular entry.

The methods and systems of the present disclosure are useful for evaluating tumor response to chemotherapy, targeted therapy, immunotherapy, radiation therapy, surgical therapy, ablative therapy, hyperthermia therapy, photodynamic therapy, laser therapy, gene therapy, biologic vector therapy, artificial vector therapy, and other forms of therapy. Further, the methods and systems of the present disclosure are applicable and useful to evaluate primary tumors, locoregional spread of tumors, and metastatic tumors; benign and malignant tumors; and a variety of tumor types, including: skin cancer, lung cancer, prostate cancer, breast cancer, colorectal cancer, kidney cancer, lymphoma, thyroid cancer, brain cancer, bone cancer, connective tissue cancer, muscle cancer, liver cancer, gastrointestinal cancer, pancreatic cancer, esophageal cancer, stomach cancer, melanoma, gynecologic cancer, cardiac cancer, and/or others.

Those skilled in the art will recognize that at least some of the presently disclosed embodiments may solve at least some of the problems associated with conventional processes for analyzing and/or tracking lesions. For instance, by providing automated segmentation/shape prediction of lesions and/or automated location identification for lesions, the disclosed systems and/or methods may allow for increased speed and/or efficiency when analyzing or tracking target lesions. Automated segmentation may also reduce variance caused by different segmentation approaches taken by different reviewing physicians when analyzing target lesions. Furthermore, automated location identification can similarly increase the speed of non-target lesion analysis and/or tracking.

Additionally, dictation errors may be avoided by automated recordation of key information (e.g., segmentation information, location information, image number or slice location of key cross-sectional images including analyzed lesions) as disclosed herein, thereby improving accuracy. Also, the disclosed embodiments may provide for increased speed when tracking lesions over time by providing functionality for predicting matching cross-sectional images to identify a matching lesion at a later timepoint that corresponds to a lesion that was analyzed at a previous timepoint.

Furthermore, coordinated analysis from physicians with different specialties and/or subspecialties may be facilitated by selectively providing subsets of cross-sectional images based on a specialty or subspecialty associated with a particular user. Also, composite reports may be generated that include analysis from multiple physicians with different specialties and/or subspecialties to provide comprehensive reports in an efficient and/or accurate manner. A composite report could be a patient-level report that includes a graph, table, key images, and structured text that is a composite of information from all subspecialty radiologists that evaluated images from the same patient. However, it should be appreciated that in some embodiments, each subspecialty report can be generated at any time outside of its specific inclusion within a composite report. That is, in some embodiments, the a patient-level report can include only one subspecialty report, and in some embodiments, a single subspecialty report can be generated by a physician for review with the patient and/or for updating patient charts and histories.

In addition, by providing personalized interaction presentation preferences for practitioners reviewing cross-sectional images for lesion analysis as described herein, the mundanity of lesion analysis may be at least partially reduced, thereby potentially increasing the accuracy of lesion tracking/analysis.

Thus, at least some embodiments of the present disclosure enable the rapid identification and tracking of lesions (e.g., target lesions, non-target lesions, and/or other lesions) throughout a clinical trial or treatment regimen so that reviewers can increase, speed, efficiency, and/or accuracy when analyzing lesions (e.g., over multiple timepoints) to evaluate tumor response.

Systems for Lesion Analysis

Referring now to FIG. 1, depicted is a schematic representation of a system for lesion analysis (e.g., for determining an objective tumor response to an anti-cancer therapy) using one or more cross-sectional images, which can implement or serve as a basis for one or more embodiments of the present disclosure. FIG. 1, generally, includes a computing system 100 configured for use in lesion analysis. In a basic configuration, a computing system includes one or more hardware processors and one or more hardware storage device that have computer-executable instructions stored thereon. The one or more processors may execute the computer-executable instructions to cause the computing system to perform certain functions and/or operations. A computing system may be in wired or wireless communication (e.g., via a network) with one or more other devices, such as other computing systems or processing centers, storage devices or databases, sensors or sensor systems (e.g., cameras and/or imaging devices), etc. to facilitate carrying out the operations detailed in the computer-executable instructions. Additional details concerning components of computing systems and computing environments will be described hereinafter.

Referring again to FIG. 1, a computing system 100 for carrying out lesion analysis is depicted as including various components, including hardware processor(s) 108, hardware storage device(s) 112, I/O device interface(s) 106, image processing module(s) 110, data processing module(s) 114, export module 118, primary database 116, and/or machine learning module(s) 120. It will be appreciated, however, that a system 100 for carrying out lesion analysis may comprise any number of additional or alternative components.

As used herein, the terms "executable module," "executable component," "component," "module," or "engine" can refer to any combination of hardware components or software objects, routines, or methods that may configure a computer system 100 to carry out certain acts. For instance, the different components, modules, engines, devices, and services described herein may be implemented as objects or processors that execute on computer system 100 (e.g. as separate threads). While FIG. 1 depicts several independent modules 110, 114, 118, 120, one will understand the characterization of a module is at least somewhat arbitrary. In at least one implementation, the various modules 110, 114, 118, 120 of FIG. 1 may be combined, divided, or excluded in configurations other than that which is shown. For example, any of the functions described herein with reference to any particular module 110, 114, 118, 120 may be performed by any number and/or combination of processing units, software objects, modules, computing centers (e.g., computing centers that are remote to computing system 100), etcetera. As used herein, the individual modules 110, 114, 118, 120 are provided for the sake of clarity and explanation and are not intended to be limiting.

The computing system 100 may obtain one or more cross-sectional medical images 102 for analysis of lesions represented in the cross-sectional images 102. The cross-sectional medical images may be captured by a radiologic device 104. In some implementations, the radiologic device 104 and the computing system 100 are physically connected such that the one or more cross-sectional images 102 are transferred directly via the physical connection. Alternatively, or additionally, the computing system 100 can obtain the cross-sectional images 102 indirectly via a network 128 to which both the radiologic device 104 and the computing system 100 are connected (whether via wired connections, wireless connections, or some combination), as known in the art. The network 128 may be any number of private networks, such as an intranet of a hospital or a private cloud or server, or the network 128 may be any number of public networks, such as a public cloud or any other public network accessible via an internet connection.

The radiologic device 104 illustrated in FIG. 1 can include any medical imaging device that generates cross-sectional images. By way of non-limiting example, a radiologic device 104 may comprise at least one of: x-ray computed tomography (CT), computed tomography perfusion (CTP) imaging, positron emission tomography (PET), single-photon emission computed tomography (SPECT), magnetic resonance imaging (MRI), or ultrasound. Consequently, in some instances, the cross-sectional images may include digital medical image data in the form of: CT images, CTP images, PET images, SPECT images, MM images, or ultrasound images, respectively.

Upon obtaining the cross-sectional images 102, the computing system 100 may store the cross-sectional images 102 in a primary database 116 or a hardware storage device 112 for immediate or later access and/or lesion analysis. In some instances, at least some of the cross-sectional images 102 are not stored on storage media that are local to the computing system 100 (e.g., primary database 116, hardware storage device(s) 112), but rather remain stored on remote computer-readable media such as storage database system 124, hardware storage device(s) of a remote computing device 130a, 130b, 130c, and/or any other remote repository. Those skilled in the art will recognize that in such and/or other instances, the operations associated with lesions analysis described herein referring to computing system 100 may be performed in a distributed and/or asynchronous manner by various computing devices.

As will be described in more detail with reference to FIGS. 2-39, the computing system 100 may operate singly or in combination with other computing systems (e.g., where at least some the cross-sectional images 102 are stored remotely, and/or one or more modules described herein are associated with a cloud service accessed by computing system 100) to analyze one or more lesions represented in one or more of the cross-sectional images 102. The computing system 100 may render the cross-sectional images 102 utilizing one or more hardware processors 108 (e.g., including a graphics processing unit (GPU)) for display on an I/O device interface 106, such as a monitor or other display screen. I/O device interface(s) 106 include any type of input or output device. Such devices include, but are not limited to, touch screens, displays, a mouse, a keyboard, a controller, head-mounted displays, speakers, sensors, sensor systems, and so forth. Any type of input or output device may be included among I/O device interface(s) 106, without limitation.

Utilizing I/O device interface(s) 106, the computing system may receive user input directing the analysis of the cross-sectional images 102 and one or more lesions represented therein. For instance, a user may operate a mouse, keyboard, touchscreen, and/or other controller to select a pixel or pixel region of a cross-sectional image 102 associated with a lesion represented in the cross-sectional image. In some instances, the user may trace an outline, boundary, or shape of a lesion shown in a cross-sectional image. In other instances, the user may select, provide, and/or modify organ location information associated with a lesion under analysis. Additional examples and implementation details regarding user input received by the computing system 100 via I/O device interface(s) 106 to facilitate lesion analysis (e.g., lesion identification/marking, longitudinal analysis, report generation, etc.) will be described in more detail hereafter.

As described herein, the computing system 100 may automate various aspects of lesion analysis to improve accuracy, reduce read times, and/or improve efficiency of lesion tracking and/or analysis. In some instances, the computing system 100 utilizes image processing module(s) 110 to automate segmentation of lesions identified in a cross-sectional image 102 to provide a predicted shape for the lesions. For example, in response to receiving user input (e.g., via I/O device interface(s) 106) selecting a pixel region within a lesion shown in a cross-sectional image 102, the image processing module 110 may analyze the intensity of pixels within the pixel region. The image processing module 110 may determine that a boundary of the lesion exists where the contrast between pixels of the pixel region and pixels surrounding the pixel region exceeds a predetermined threshold level. The image processing module 110 may provide a predicted shape of the lesion based on the detected boundary, and the image processing module 110 may interpolate between boundary pixels to account for outlier boundary pixels and/or to provide a smooth lesion boundary.

In some instances, the image processing module 110 utilizes multiple different contrast threshold levels or edge sensitivity levels to determine multiple predicted shapes for the lesion, and the computing system 100 may allow or prompt the user to select a desired predicted shape as the segmentation for the lesion under analysis. In other instances, the threshold contrast or edge sensitivity is selectively modifiable by the user, and it will be appreciated that any other constraints may be applied to guide the segmentation process (e.g., shape, size, contour, angular, and/or curvature constraints). By way of example, in some implementations, the image processing module 110 may attempt to identify one or more (separate) pixel regions in neighboring cross-sectional images (e.g., at a higher or lower slice location or image number) that correspond to the pixel region of the lesion selected by the user, and perform contrast analysis on the separate pixel regions of the neighboring images to determine predicted shapes for the separate pixel regions. The image processing module 110 may then utilize the shapes and/or sizes of the predicted shapes for the neighboring pixel regions as inputs for determining the predicted shape of lesion within the cross-sectional image under analysis.

As noted above, tracking target lesions over time is advantageous for obtaining accurate and precise evaluations of objective tumor response. To track a target lesion over multiple timepoints, a reviewer identifies a previously analyzed target lesion within a set of cross-sectional images captured at a timepoint subsequent to the timepoint at which the target lesion was previously analyzed.

In some embodiments, the image processing module 110 at least partially automates the identification of a later-timepoint cross-sectional image that includes the same lesion that was analyzed in a previous-timepoint cross-sectional image. For example, the image processing module 110 may identify a predicted matching cross-sectional medical image (e.g., within a later-timepoint set of cross-sectional images) that corresponds to a previously captured cross-sectional image that included a lesion that was previously analyzed by image co-registration, feature matching, intensity similarity, and/or other techniques. The image processing module 110 may operate within various constraints to identify a predicted matching cross-sectional image, such as similarity thresholds or a search window within which to search for a matching image (e.g., a search window identified and/or centered based on a slice location of the previous-timepoint cross-sectional image). The image processing module 110 may expand the search window and/or selectively modify other inputs and/or constraints if no later-timepoint cross-sectional image meets or exceeds a predefined threshold of similarity to the previous-timepoint cross-sectional image containing the previously analyzed lesion.

The computing system 100, as shown in FIG. 1, also includes machine learning module(s) 120, which may be configured to perform any of the operations, method acts, and/or functionalities disclosed herein. For example, machine learning module(s) 120 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As used herein, reference to any type of machine learning may include any type of artificial intelligence algorithm, device, structure, and/or architecture. Any amount or type of training data (e.g., datasets comprising cross-sectional medical images, control inputs provided by users, and/or, as ground truth, data corresponding to lesion analysis (e.g., lesion identification, segmentation, etc.) performed using the cross-sectional medical images) may be used (and/or later refined) to train a machine learning model to provide output for facilitating any of the disclosed operations.

In some instances, the computing system 100 utilizes machine learning module 120 to at least partially automate the localization of target lesions and/or non-target lesions. In some implementations, the machine learning module 120 is trained to identify location information for a lesion based on various input (e.g., type of cross-sectional image under analysis). For example, in some implementations, the computing system 100 provides the predicted shape (e.g., as determined above utilizing the image processing module 110, and/or as modified/indicated by user input) to the machine learning module 120 as input and causes the machine learning module to identify the location information for the analyzed lesion based on the predicted shape.

It should be noted that the machine learning module 120 may also be trained to receive other input for identifying location information for a lesion. In some instances, the machine learning module 120 receives as input a form of metadata indicative of an anatomical or organ location of the lesion. Such metadata may be associated with the particular cross-sectional image under review, the set of cross-sectional images 102 of which the particular cross-sectional image is a part, or even a user profile associated with the user performing the lesion analysis. For example, cross-sectional image or image set metadata may include an identifier of a slice location or image number or applicable anatomical location for the images captured (e.g., chest, abdomen, head, neck). Also, the user profile of the reviewer may indicate a radiology subspecialty (e.g., neuroradiology or thoracic radiology, which can include chest or abdomen subspecialties) which may inform the identification of the anatomical information associated with the lesion under analysis. In other instances, the machine learning module 120 receives as input pixel coordinates of user input directed at the lesion or of a pixel region within the lesion to guide the identification of the location information for the lesion. In yet other instances, the machine learning module analyzes structures neighboring the identified lesion and/or analyzes the cross-sectional image as a whole to identify the location information for the identified lesion.

As depicted in FIG. 1, the computing system 100 also includes data processing module(s) 114 and an export module 118. The data processing module 114, in some implementations, operates to determine or obtain lesion metrics associated with a lesion (e.g., a target lesion) under analysis or review. For instance, the data processing module 114 may, for one or more lesions at one or more timepoints, determine a major axis, a minor axis, and/or pixel area based on predicted lesion shape. The data processing module 114 may also perform calculations on lesion axes (e.g., comparing sums of the lengths of lesion axes over time) or other metrics to determine tumor response and/or disease progression based on predefined tumor response criteria as discussed above.

The data processing module 114 and/or the export module 118, in some implementations, is also responsible for organizing and/or storing data/information associated with analyzed lesions. For example, the data processing module 114 may store and/or copy within one or more lists or databases the predicted shape, axes (major and/or minor), slice location or cross-sectional image number, location information, key images (e.g., images showing close-up views of a lesion), or any combinations or representations thereof associated with any number of lesions at any number of timepoints. For example, in some embodiments, any of the foregoing types of data associated with the lesions become stored in association with and/or within the cross-sectional images themselves (e.g., as metadata or as a modified version of the cross-sectional images with data implemented or embedded therein). In some instances, the data/information become stored within hardware storage device(s) 112, remote storage database system(s) 124 (e.g., within a cloud server), and/or on one or more remote computing device(s) 130*a*, 130*b*, 130*c* (via network 128).

In some implementations, and as will be discussed hereafter, the data processing module 114 and/or export module 118 may compile or generate reports based on any of the data/information described herein for oncological and/or patient review. Such reports may comprise one or more results and/or output of lesion analysis performed by one or more than one physician.

It will be appreciated that the computing devices 130*a*, 130*b*, 130*c* can have any or all of the components and modules described above for the general computing system 100. In some instances, the computing system 100 can include the workstation of a physician reviewer. Alternatively, the computing system 100 can include a server for hosting or facilitating user interaction with cross-sectional images and/or computer-executable instructions (e.g., in the form of software or an SaaS platform) for standardizing target lesion identification and selection within cross-sectional images, as described herein. Similarly, the computing devices 130*a*, 130*b*, 130*c* can represent the workstations of other reviewers, or the computing devices 130*a*, 130*b*, 130*c* can be user profiles or virtual instances of computing system 100. For instance, different physician reviewers with different specialties and/or subspecialties may perform lesion analysis on different subsets of one or more sets of cross-sectional medical images, and such analysis may be performed at the same or different times. Such analysis by multiple reviewing physicians may be compiled into a composite report by any of the computing systems/devices described herein.

Regardless of the physical and/or virtual organization of the computing system 100 and/or the associated computing devices 130*a*, 130*b*, 130*c*, embodiments of the present disclosure enable cross-sectional images to be received and/or viewed at any of the foregoing system/devices 100, 130*a*, 130*b*, 130*c*. The ellipsis shown in FIG. 1 indicate that any number of computing systems (e.g., 1, 2, or more than 3) may be in communication with computing system 100 via network 128.

Example Implementations of Lesion Analysis

The following discussion refers to FIGS. 2-39 and provides additional details, examples, and implementations related to systems and methods for analyzing lesions in cross-sectional medical images. It will be appreciated that the contents of the accompanying Figures are not mutually exclusive. For instance, any feature, component, or embodiment shown in any one of the accompanying Figures may be combined with one or more features, components, or embodiments shown in any other accompanying Figure.

Figure 2:
FIG. 2 illustrates an example of a display interface rendering associated with a system for facilitating lesion analysis as the system presents one or more cross-sectional medical images, according to the present disclosure.

FIG. 2 illustrates an example of a display interface rendering associated with a system for lesion analysis (e.g., computing system 100) as the system presents cross-sectional medical images within a user interface. The display interface rendering may be displayed to a user on one or more I/O device interfaces 106 (e.g., on a screen or monitor). As shown, the display interface rendering includes a rendering of a cross-sectional medical image 202, which may comprise one cross-sectional image of a set or plurality of cross-sectional medical images (i.e., the rendered image is slice 1 of 273, as indicated in the upper-left corner of the rendered image) that is available to the user. The cross-sectional medical images may be captured by a radiologic device 104, as described above, and may be associated with a particular patient.

As indicated hereinabove with reference to FIG. 1, the user may access the system through a local connection with the system (e.g., by interfacing with the system itself or through a local network to which the system is connected) or a remote connection with the system (e.g., via a cloud service).

The user interface includes an icon 204 representative of a user-operated controller (shown in FIG. 2 as a mouse cursor) and/or various controls (e.g., buttons of a mouse that controls the mouse cursor) for performing various functions. Other controls may be operable for providing user input within the user interface not shown in FIG. 2 (e.g., keyboard or other physical controls that are operable by the user to interface with the system).

Figure 3:
FIG. 3 illustrates an example of a display interface rendering associated with a system for facilitating lesion analysis as the system displays a different cross-sectional medical image in response to user input, according to the present disclosure.

FIG. 3 illustrates an example of a display interface rendering as the system displays a different cross-sectional medical image 302 in response to user input. In particular, in FIG. 3, the system displays slice 20 of 273 (whereas slice 1 of 273 was presented as shown in FIG. 2). The user may provide input at an I/O device interface 106 (e.g., by scrolling a mouse wheel or moving the mouse cursor while operating a control) to navigate from one cross-sectional medical image to another in order to view different cross-sectional medical images. By navigating through the cross-sectional images provided in the set, a user (e.g., a reviewer) may navigate to a suitable lesion (e.g., a target lesion or a non-target lesion) represented in a cross-sectional image upon which to carry out lesion analysis, as described herein.

Figure 4:
FIG. 4 illustrates an example of a display interface rendering associated with a system for facilitating lesion analysis as the system receives user input selecting a pixel region associated with a target lesion represented in the displayed cross-sectional medical image, according to the present disclosure.

FIG. 4 illustrates an example of a display interface rendering as the system presents the cross-sectional medical image 302 (e.g., from FIG. 3) and receives user input selecting a pixel region 402 associated with a target lesion 404 represented in the displayed cross-sectional medical image 302. In the depicted example, the user has triggered a control for selecting a target lesion 404 for which to measure lesion metrics (e.g., axis length, pixel area, location information, etc.), causing, in this example, the mouse cursor 406 to change shape (e.g., to a cross rather than an arrow as shown in FIGS. 2 and 3). In the example shown in FIG. 4, the cursor 406 has navigated over a lesion 404 in the axillary region to provide user input directed to a pixel region 402 within the lesion 404 represented in the cross-sectional image 302. The user may provide the user input via an I/O device interface, such as by pressing a mouse button.

Figure 5:
FIG. 5 illustrates an example of a display interface rendering associated with a system for facilitating lesion analysis as the system provides a zoomed view of the target lesion, according to the present disclosure.

FIG. 5 illustrates an example of a display interface rendering as the system provides a zoomed view of the target lesion 404 within the cross-sectional medical image 302. In some embodiments, in response to the user input described with reference to FIG. 4 (e.g., pressing a mouse button), the system zooms (e.g., automatically) the presentation of the cross-sectional medical image 302 toward the lesion 404 represented in the cross-sectional medical image 302 that the user input was directed toward (e.g., toward the pixel or pixel region 402 selected by the user input). The zoomed presentation may provide for more accurate and/or rapid analysis of the lesion 404 by enabling users to more easily recognize the features of the analyzed lesion 404. In some instances, the system auto-zooms so that the selected target lesion 404 is centered (or as nearly centered as possible given the location of the lesion) in the viewing area.

In some implementations, the degree of magnification is modifiable. For instance, the degree of magnification may be automatically modified based on the size and/or location of the selected target lesion 404. In some instances, the degree of magnification can be adjusted by a user (e.g., according to their individual user profile or other settings). By way of non-limiting example, the image may be magnified within a range of about 100% to about 500% or more. In some embodiments, a standard or preset magnification setting is 200%.

Following segmentation and/or further identification of the target lesion 404 (as will be described in more detail hereinbelow), the system can return the magnification and view to the original 100% view of the cross-sectional medical image 302 (e.g., as shown in FIG. 4). The foregoing can be done automatically or in response to user input. In some embodiments, the magnification/zoom feature is performed automatically by the system to maximize the ease and speed of traditional radiology workflows.

Figure 6:
FIG. 6 illustrates an example of a display interface rendering associated with a system for facilitating lesion analysis as the system provides a predicted shape of the target lesion, according to the present disclosure.

FIG. 6 illustrates an example of a display interface rendering as the system provides a predicted shape 602 of the target lesion 404. The predicted shape 602 may be thought of as a predicted segmentation for the lesion 404 selected by the user. In some embodiments, the system provides the predicted shape 602 utilizing, at least in part, image processing module(s) 110 and/or machine learning module(s) 120 based on contrast or intensity analysis of one or more cross-sectional images and/or other factors/inputs as described hereinabove with reference to FIG. 1. In the example depicted in FIG. 6, the system presents a rendering of the predicted shape 602 of the lesion 404 overlaid on the lesion 404 as represented in the cross-sectional image 302 to the user. By providing automated segmentation (e.g., shape prediction), at least some presently disclosed embodiments may increase the rate at which lesions are analyzed in cross-sectional medical images.

Figure 7:
FIG. 7 illustrates an example of a display interface rendering associated with a system for facilitating lesion analysis as the system displays major and minor axes based on the predicted shape of the target lesion, according to the present disclosure.

FIG. 7 illustrates an example of a display interface rendering as the system displays a major axis 702 and a minor axis 704 based on the predicted shape 602 of the target lesion 404. For instance, the system may calculate major axis 702 and/or the minor axis 704 for the analyzed lesion 404 utilizing, at least in part, data processing module(s) 114 and/or machine learning module(s) 120. Upon determining the major axis 702 and/or the minor axis 704, the system may display one or both of them overlaid on the lesion 404 in the cross-sectional image 302, as illustrated in FIG. 7. The respective lengths of the major axis 702 and the minor axis 704 may also be presented by the system, as shown in FIG. 7.

Figure 8:
FIG. 8 illustrates an example of a display interface rendering associated with a system for facilitating lesion analysis as the system selectively disables a display of the predicted shape, according to the present disclosure.

FIG. 8 shows an example of a display interface rendering as the system selectively disables a display of the predicted shape 602 of the target lesion 404, while maintaining a display of the major axis 702 and the minor axis 704 associated with the lesion 404. The system may selectively disable the presentation of the predicted shape 602 in response to received user input (e.g., to allow the user to rapidly verify that the segmentation provided by the system for the target lesion 404 is desirable or correct). Those skilled in the art will appreciate, in view of the present disclosure, that the system need not calculate and/or present major and/or minor axes for all analyzed lesions. For instance, for some types of lesions, the minor axis may be considered more critical for analyzing tumor response (e.g., when analyzing lymph nodes) so calculations and/or presentations of the major axis may be omitted.

The system may prompt the user to accept or reject the predicted shape 602 or segmentation provided by the system, as indicated in FIG. 8 by the right-facing arrow button for accepting the predicted shape 602 and the left-facing arrow button for rejecting the predicted shape 602 shown in/over the upper-left portion of the displayed cross-sectional image 302.

Figure 9:
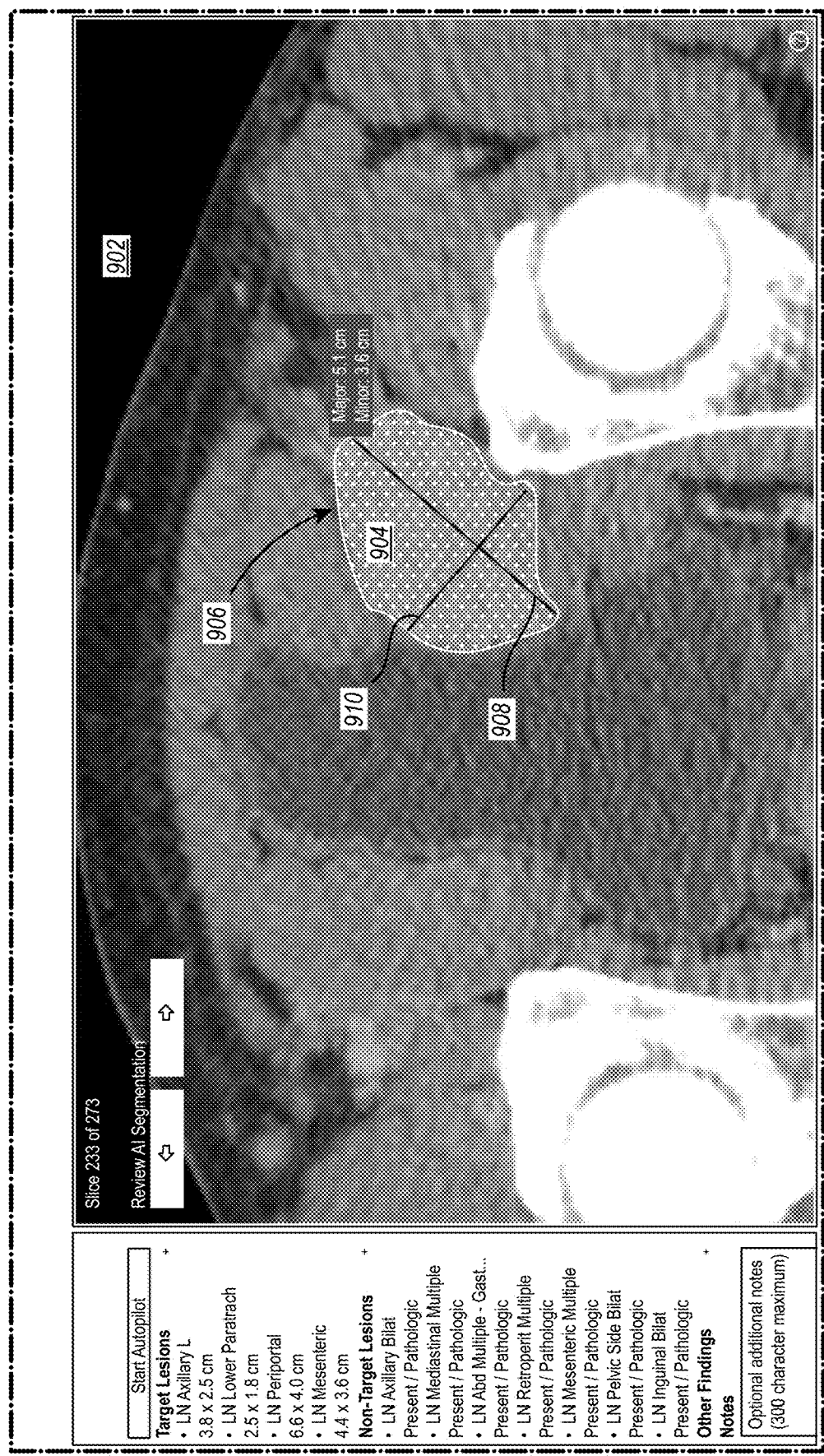
FIG. 9 illustrates an example of a display interface rendering associated with a system for facilitating lesion analysis as the system provides a predicted shape of another target lesion, according to the present disclosure.

In some instances, the system (e.g., utilizing image processing module(s) 110 and/or machine learning module(s) 120) may provide an undesirable predicted shape or segmentation for a lesion selected by user input (e.g., due to variations in quality/resolution of cross-sectional medical images). For instance, FIG. 9 illustrates an example of a display interface rendering as the system displays a cross-sectional medical image 902 (e.g., image slice 233 of 273) and provides a predicted shape 904 of a target lesion 906 proximate to the pelvis of the patient (e.g., in response to user input). As shown, the system presents a rendering of the predicted shape 904 or segmentation and the major axis 908 and the minor axis 910 overlaid on the target lesion 906 within the cross-sectional image 902 and prompts the user to accept or reject the predicted shape 904 or segmentation (indicated by the buttons shown over the upper-left portion of the cross-sectional image 902).

Although the major axis 908 and the minor axis 910 generated by the system based on the predicted shape 904 may appear correct, the user may believe that a more desirable segmentation of the lesion 906 may be achieved manually. Thus, in some instances, the user may reject the predicted shape 904 generated by the system and/or provide user input that modifies the predicted shape 904 or segmentation for the target lesion 906.

Figure 10:
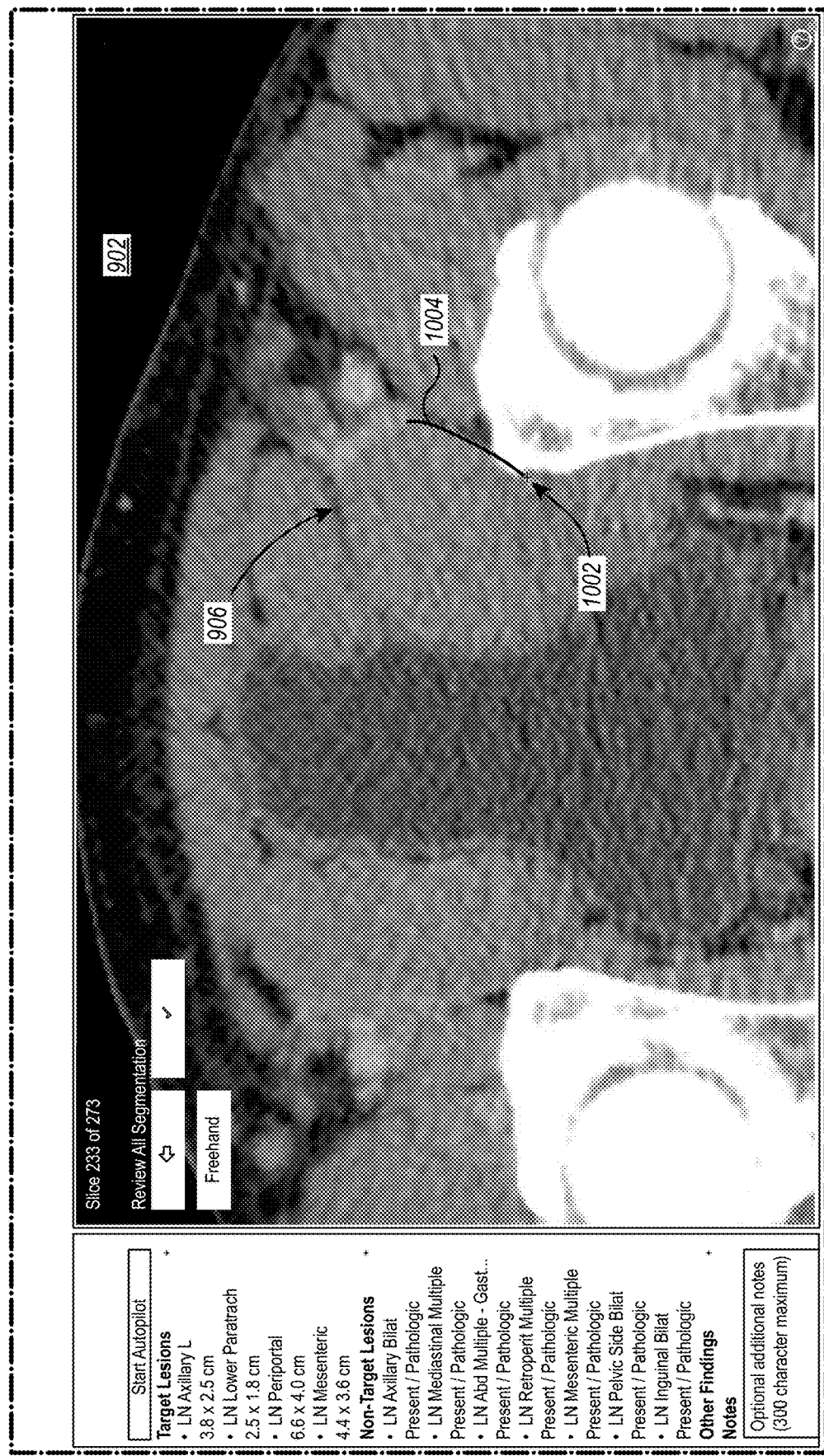
FIGS. 10-12 illustrate examples of display interface renderings associated with a system for facilitating lesion analysis as the system receives user input modifying the predicted shape the target lesion, according to the present disclosure.
Figure 11:
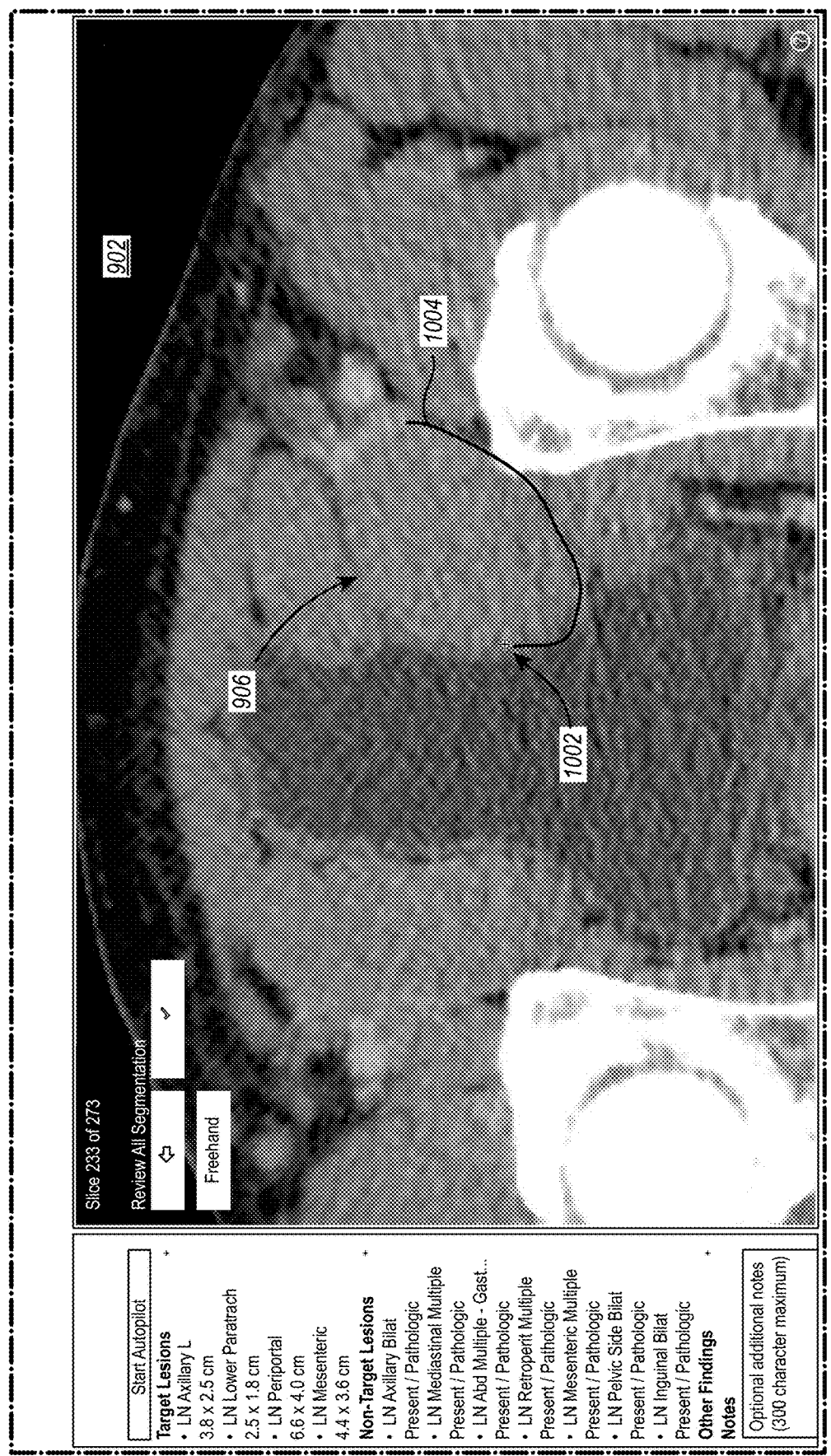
Figure 12:
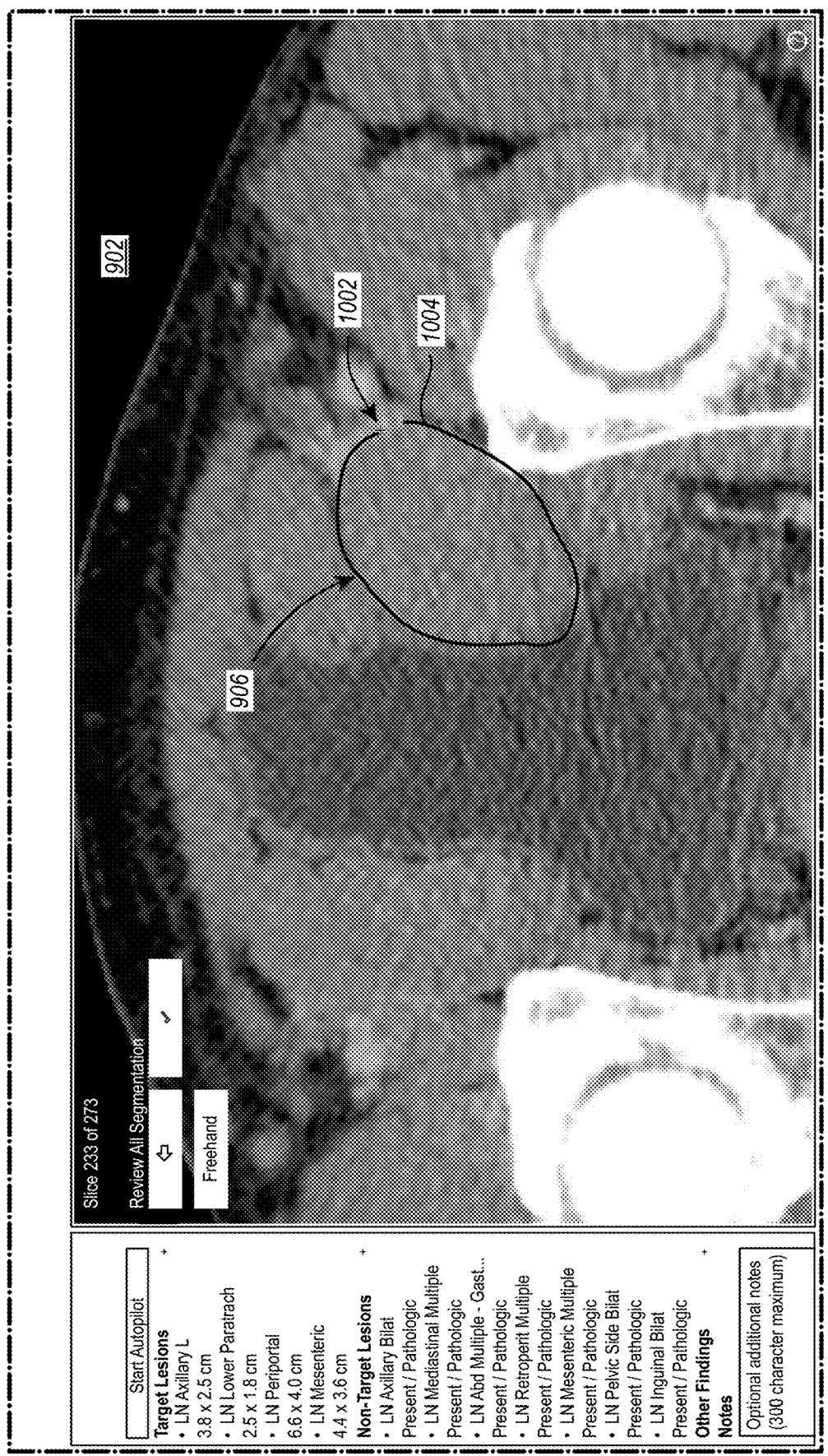

FIGS. 10-12 illustrate examples of display interface renderings as the system receives user input modifying/defining the predicted shape the target lesion 906. In some embodiments, as depicted, the system provides a free-form region of interest trace tool to allow the user to modify the segmentation of the lesion 906. For example, FIGS. 10-12 show that a user may control an icon 1002 (e.g., by selecting a mouse button and moving the mouse, or by operating a touch screen, etc.) to manually trace a line 1004 that modifies or defines a predicted shape/segmentation for the target lesion 906.

Figure 13:
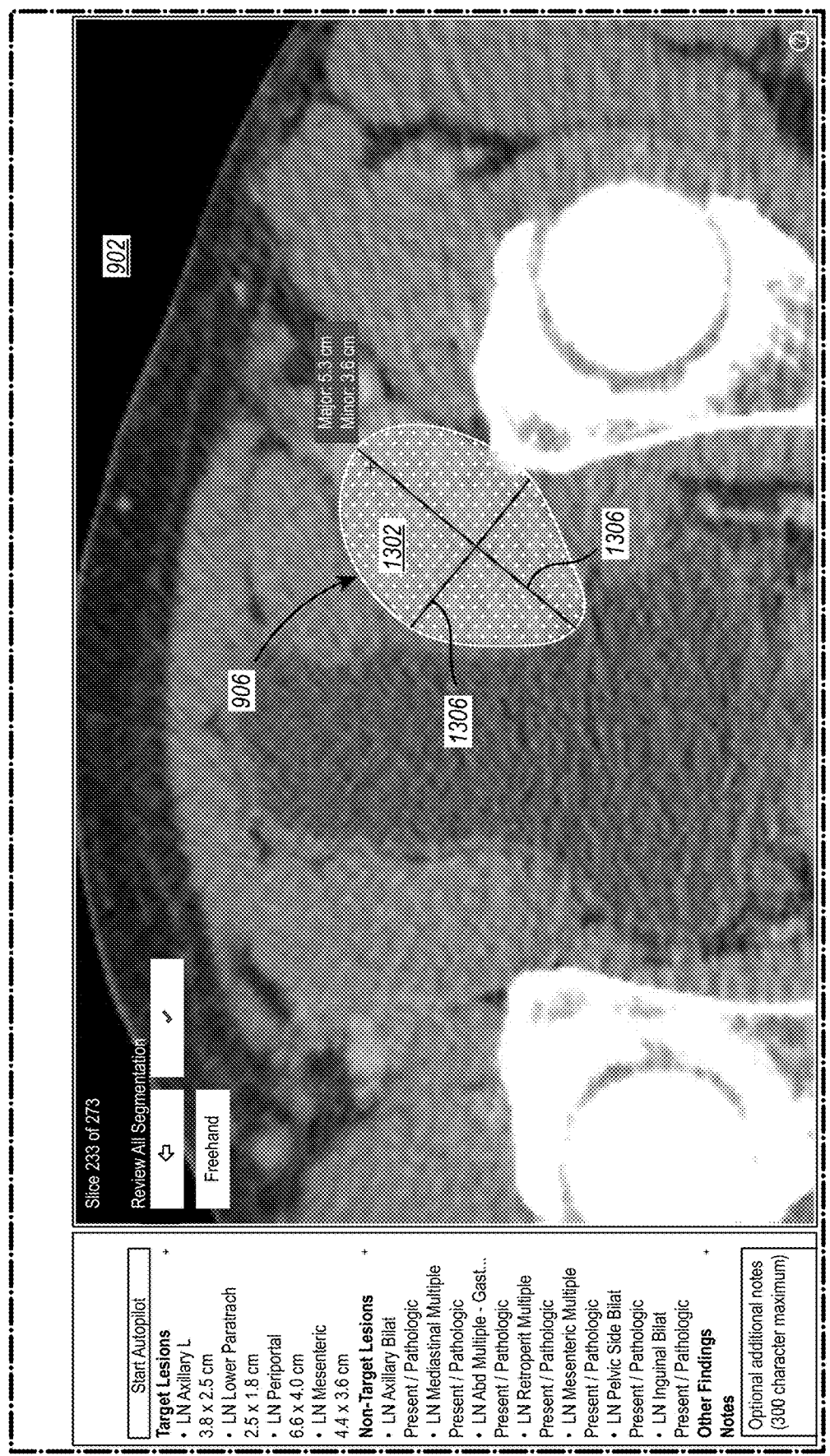
FIG. 13 illustrates an example of a display interface rendering associated with a system for facilitating lesion analysis as the system displays the predicted shape of the target lesion as modified by the received user input, according to the present disclosure.

Based on the user input modifying/defining the predicted shape/segmentation for the target lesion 906, the system may provide an updated predicted shape 1302 of the target lesion 906 (and/or a major axis 1304, a minor axis 1306, and/or other lesion metrics for the target lesion 906), as shown in FIG. 13. In some instances, the system utilizes at least a part of the user input modifying the predicted shape (e.g., as shown in FIGS. 10-12) as an input to generate the updated predicted shape 1302 of the target lesion 906 (e.g., as an additional constraint/input that affects the boundaries of the updated predicted shape 1302), while in other instances the system receives user input corresponding to a complete trace of the target lesion 906 such that the system makes no further predictions about the shape and accepts the user input as the updated predicted shape 1302 or updated segmentation of the target lesion 906.

Figure 14:
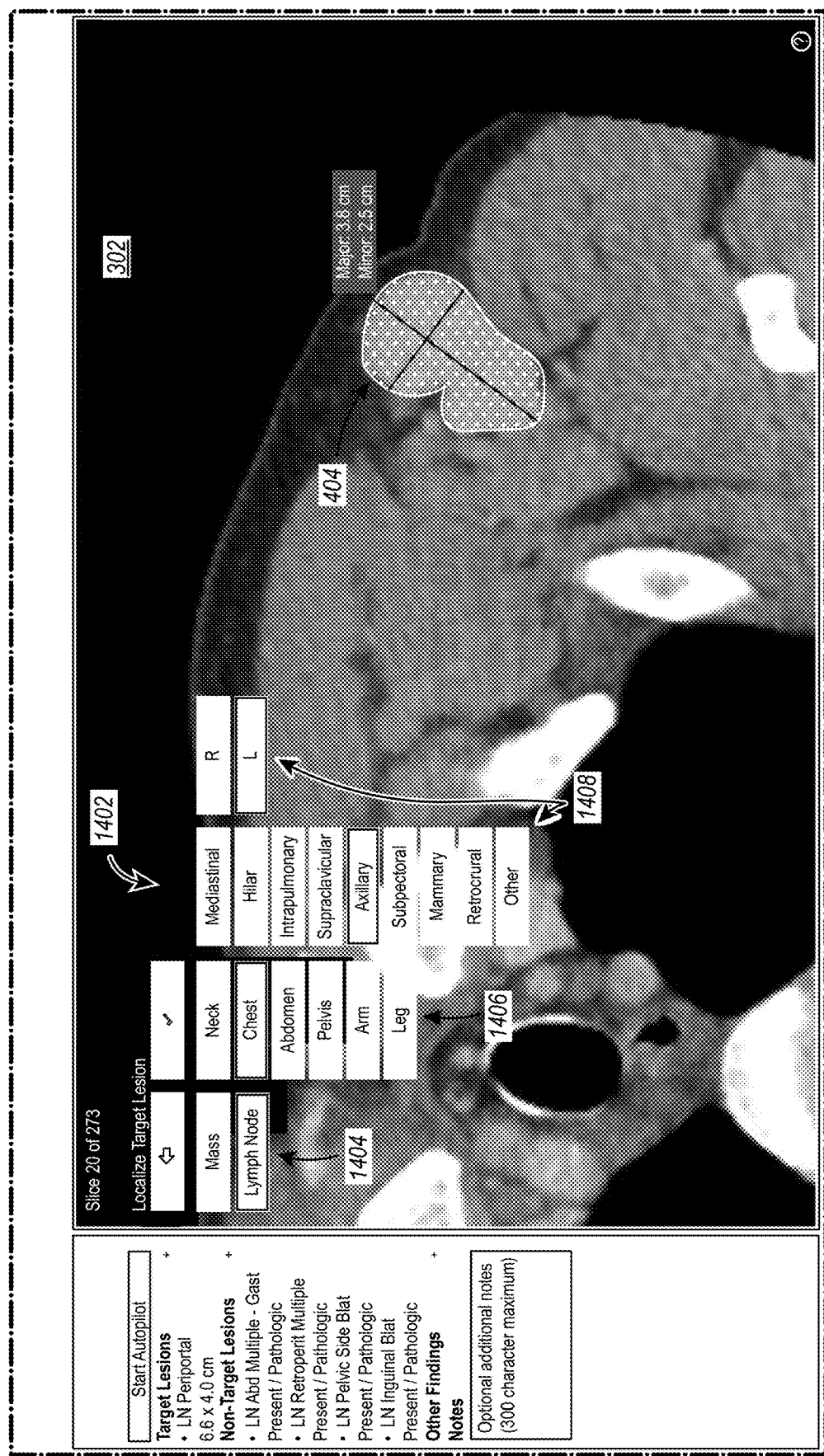
FIG. 14 illustrates an example of a display interface rendering associated with a system for facilitating lesion analysis as the system provides automatically determined location information for the target lesion depicted in FIGS. 6-8, according to the present disclosure.

FIG. 14 illustrates an example of a display interface rendering as the system provides automatically determined location information 1402 for the target lesion 404 in the axillary region shown and described with reference to FIGS. 6-8. A system may utilize any combination of components (e.g., image processing module(s) 110, data processing module(s) 114, machine learning module(s) 120, hardware processor(s) 108) to generate location information 1402 for a target lesion.

As shown, the location information 1402 includes an indication region 1404 of whether the lesion under analysis is a mass or a lymph node, an indication region 1406 of whether the lesion is located within the neck, chest, abdomen, pelvis, arm, or leg of the patient, as well as other indication regions 1408 of the anatomical location of the lesion. In the embodiment shown, the system automatically determined that the lesion 404 is a lymph node located in the left axillary region of the chest of the patient. This information is reflected in the location information 1402 presented by the system contemporaneously with a presentation of a rendering of the lesion 404 in the cross-sectional image 302 (as well as the predicted shape/segmentation of the lesion 404 and the major and minor axes of the lesion). For instance, indication region 1404 of the location information 1402 has the label/button "Lymph Node" emphasized, selected, or highlighted; indication region 1406 of the location information 1402 has the label/button "Chest" emphasized, selected, or highlighted; and indication regions 1408 of the location information 1402 have the labels/buttons of "Axillary" and "L" (indicating "Left") emphasized, selected, or highlighted.

In some instances, as shown in FIG. 14, the system presents the location information 1402 to the user and allows the user to accept or modify the location information 1402 provided by the system. For instance, FIG. 14 shows a check mark button shown over the upper-left portion of the rendered cross-sectional image 302, which a user may select upon determining that the location information 1402 generated by the system appears accurate or desirable. Furthermore, the various elements of the indication regions 1404, 1406, 1408 of the location information 1402 may, in some implementations, be presented as selectable buttons, enabling a user to easily modify the location information 1402 for a target lesion.

As noted above with reference to FIG. 1, the system may utilize (at least in part) machine learning module(s) 120 to automatically determine location information for the lesion. The machine learning module 120 may be trained to identify location information based on an input of a predicted shape/segmentation of the lesion and/or coordinates of user input selecting the lesion (described above), or the machine learning module 120 may be trained/configured to utilize other additional or alternative inputs such as other structures present in the cross-sectional image or other characteristics of the cross-sectional image as a whole, metadata associated with the cross-sectional images, a user profile, and/or other identifiers.

Figure 15:
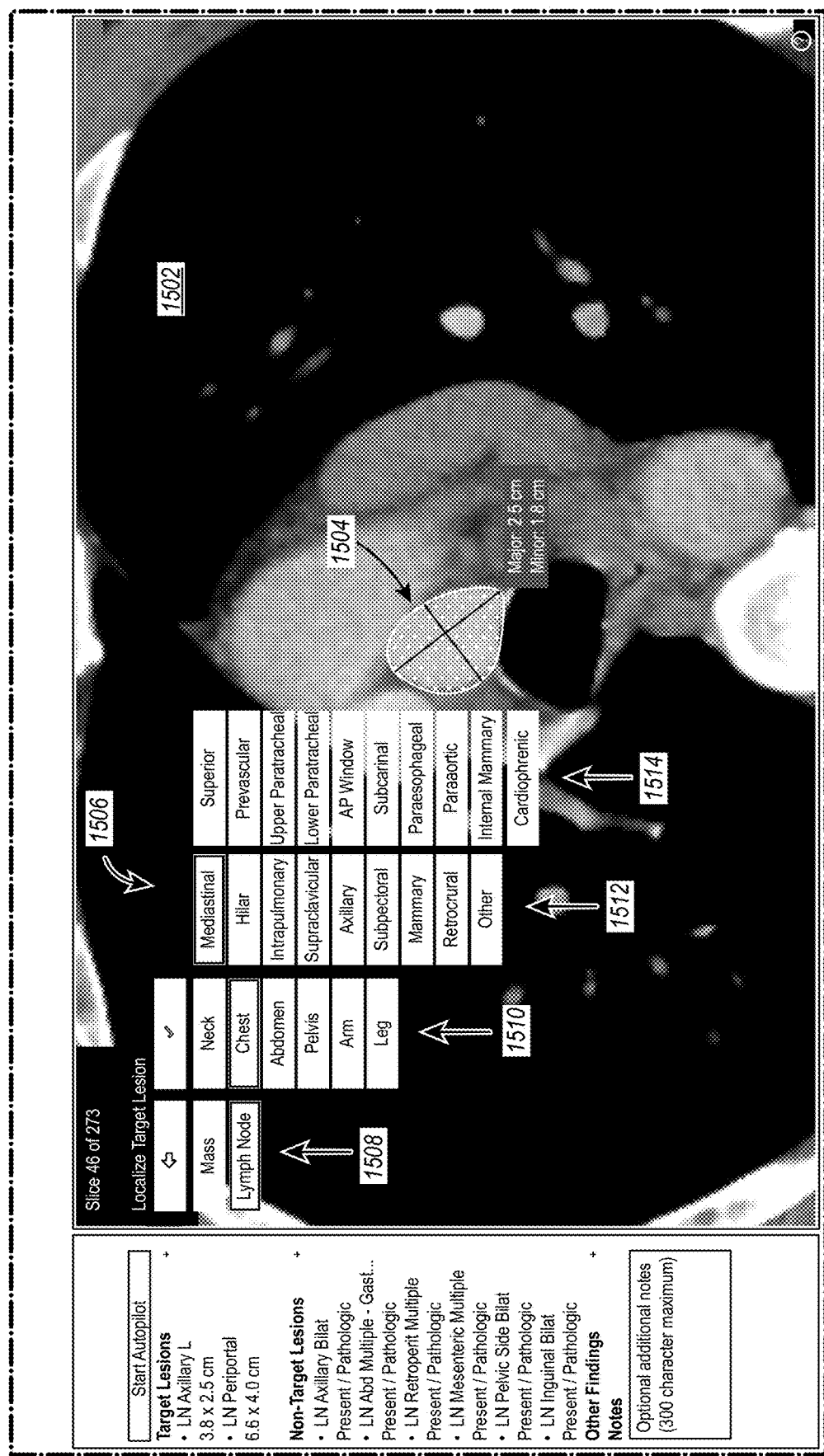
FIG. 15 illustrates an example of a display interface rendering associated with a system for facilitating lesion analysis as the system provides automatically determined location information for another target lesion, according to the present disclosure.

FIG. 15 illustrates an example of a display interface rendering associated with a system for lesion analysis as the system presents a cross-sectional medical image 1502 (slice 46 of 273) and provides automatically determined location information 1506 for a target lesion 1504 in the mediastinal region. As noted above, the system may present the automatically determined location information 1506 for the target lesion 1504 and prompt the user to either accept the location information 1506 or modify the location information 1506. In the example shown, the location information 1506 includes an indication region 1508 that indicates that the lesion 1504 being analyzed is a lymph node, an indication region 1510 that indicates that the lesion 1504 is located in the chest of the patient, and an indication region 1512 that indicates that the lesion 1504 is located in the mediastinal region of the chest.

However, the location information 1506 also includes an indication region 1514 with no particular element thereof emphasized, selected, or highlighted, thereby prompting the user to make a selection among the elements of the indication region 1514 to modify the location information 1506. Here, the system prompts the user to specify within the indication region 1514 of the location information 1506 whether the target lesion 1504 is a superior, prevascular, upper or lower paratracheal, AP window, subcarinal, paraesophageal, paraaortic, internal mammary, or cardiophrenic lymph node within the mediastinal region. Accordingly, in some implementations, the system provides location information to a certain level of granularity but allows the user to add additional details if the user desires (e.g., where the system is unable to provide a granular location estimate).

Figure 16:
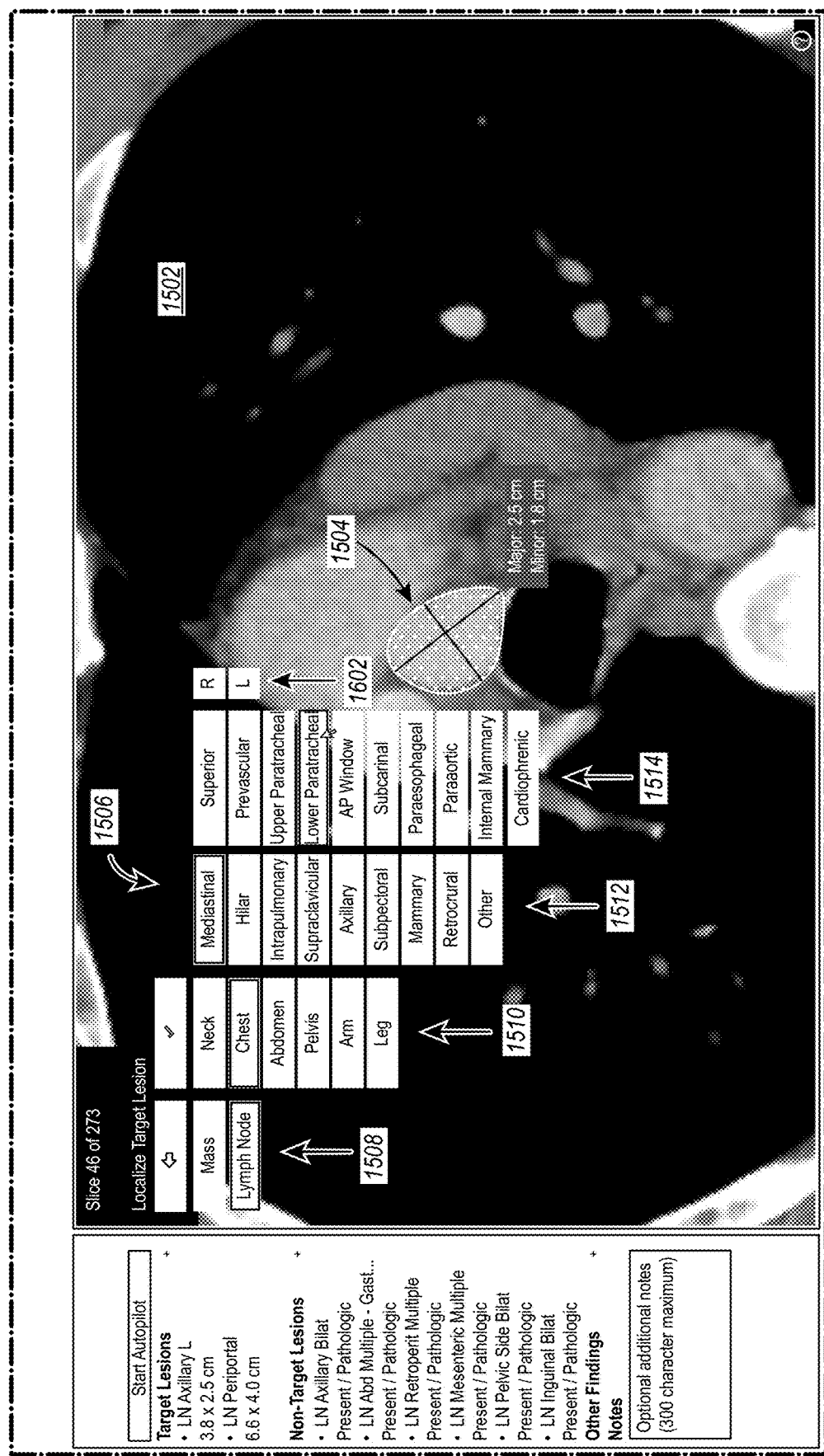
FIG. 16 illustrates an example of a display interface rendering associated with a system for facilitating lesion analysis as the system receives user input adding to the location information for the target lesion previously provided by the system, according to the present disclosure.

FIG. 16 illustrates an example of a display interface rendering as the system receives user input within the indication region 1514 of the location information 1506, where the user input indicates that the target lesion 1504 identified with reference to FIG. 15 is a lower paratracheal lymph node in the mediastinal region of the chest. In response to this user input, as shown in FIG. 16, the system generates an additional indication region 1602 and further prompts the user to input whether the target lesion 1504 is "left" or "right," and the user may elect whether to so specify before choosing to accept or reject the location information provided by the system and/or as modified by the user (e.g., using the check mark button in the upper-left region to accept, or the leftward arrow button in the upper-left region to reject). As will be described hereinafter, location information for a target lesion, whether solely generated by the system or at least partially modified by a user, may be stored for use in lesion analysis.

Figure 17:
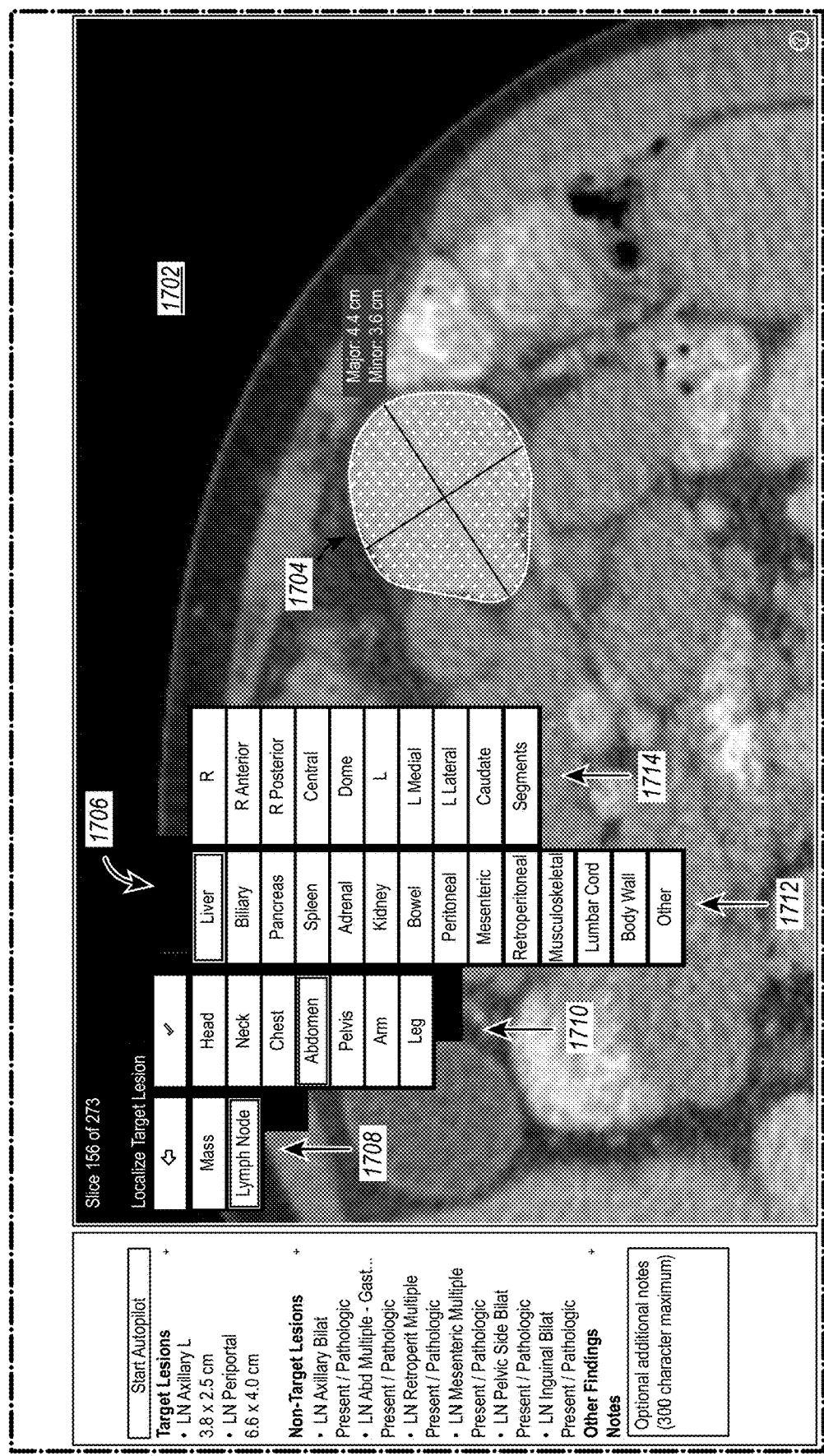
FIG. 17 illustrates an example of a display interface rendering associated with a system for facilitating lesion analysis as the system provides automatically determined location information for another target lesion, according to the present disclosure.

In some instances, the system provides location information that is at least partially incorrect. For instance, FIG. 17 illustrates an example of a display interface rendering as the system displays a cross-sectional image 1702 (slice 156 of 273) and provides automatically determined location information 1706 for a target lesion 1704 that is a lymph node located in the mesenteric region of the patient. In the instance shown, the system provides location information 1706 that includes an indication region 1708 indicating that the target lesion 1704 is a mass, an indication region 1710 indicating that the target lesion 1704 is located within the abdomen of the patient, an indication region 1712 indicating that the target lesion 1704 is located in the liver, and an indication region 1714 allowing the user to select additional location information for the target lesion 1704. As noted above, the various elements of the various indication regions 1708, 1710, 1712, and 1714 of the location information 1706 may be provided as selectable buttons, enabling a user to modify the location information 1706 before accepting or rejecting the location information 1706 (e.g., via the check mark button or the leftward arrow button in the upper-left region).

Figure 18:
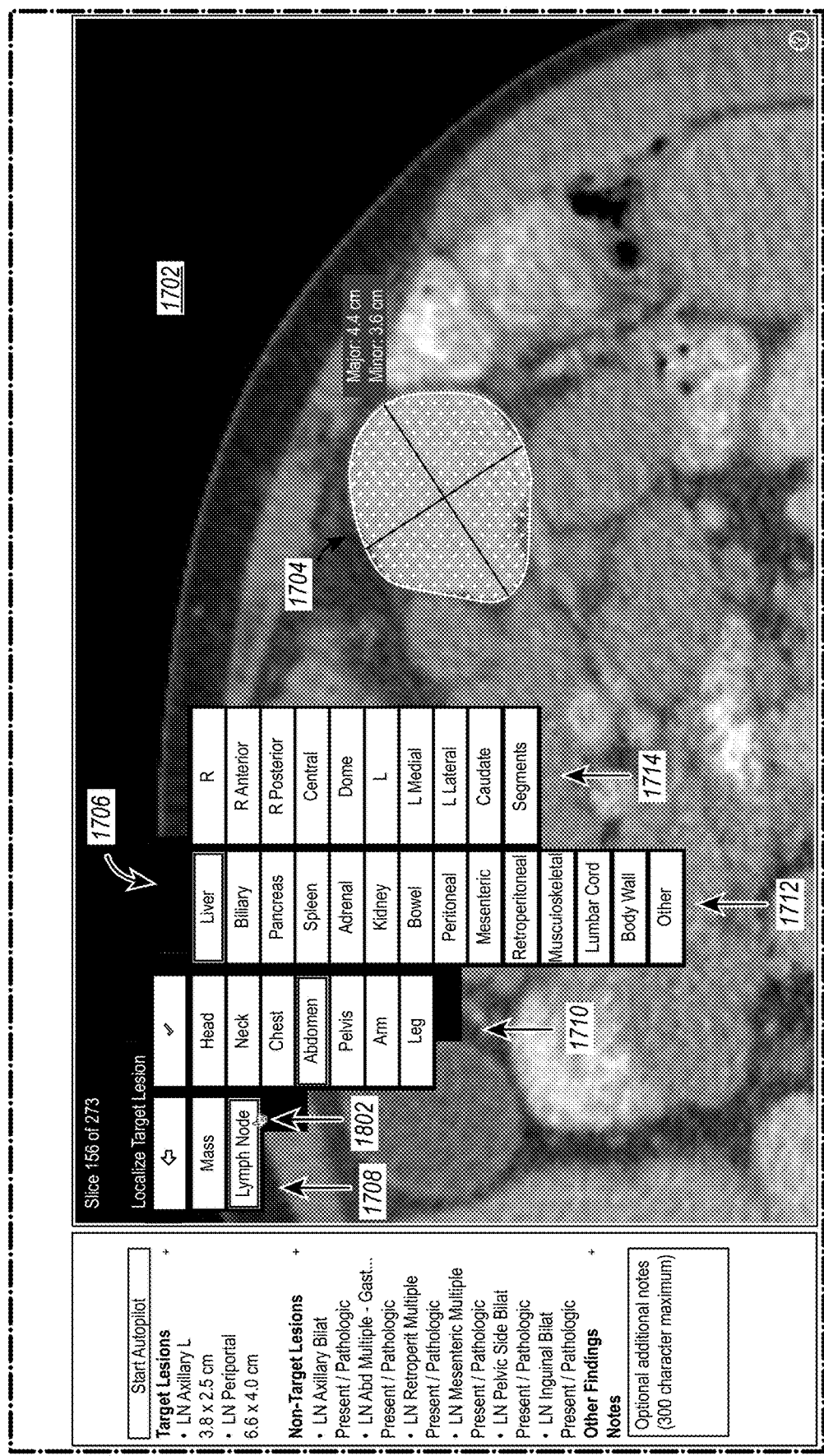
FIG. 18 illustrates an example of a display interface rendering associated with a system for facilitating lesion analysis as the system receives user input modifying the location information for the target lesion previously provided by the system, according to the present disclosure.

The user may determine that the location information 1706 provided by the system is at least partially inaccurate in the particular instance and choose to modify the location information 1706. FIG. 18 illustrates an example of a display interface rendering as the system receives user input modifying the location information 1706 for the mesenteric lymph nodes target lesion 1704 previously provided by the system. As shown, the cursor 1802 has been navigated (e.g., via a mouse or other interface device) over the selectable "Lymph Node" element/button of the indication region 1708 of the location information 1706 to provide user input to the system to modify the location information 1706 associated with the target lesion 1704 to indicate that the target lesion is a lymph node rather than a mass.

Figure 19:
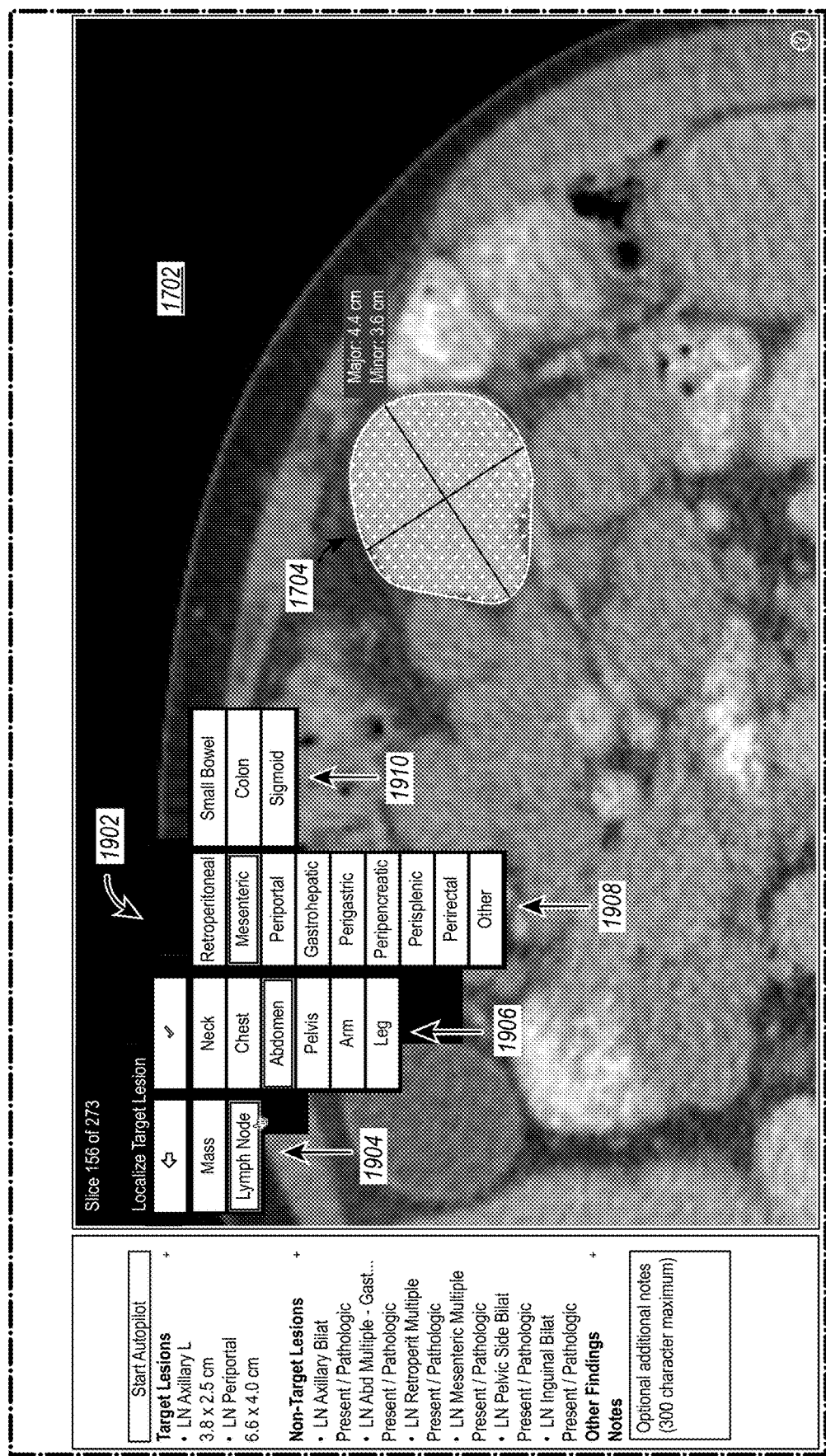
FIG. 19 illustrates an example of a display interface rendering associated with a system for facilitating lesion analysis as the system provides updated location information for the target lesion based on received user input modifying previously provided location information for the target lesion, according to the present disclosure.

FIG. 19 illustrates an example of a display interface rendering as the system responds to the received user input described with reference to FIG. 18 (e.g., selecting the "Lymph Node" element/button of the indication region 1708 of the location information 1706). As shown in FIG. 19, the system provides updated location information 1902 for the target lesion 1704. For example, in some implementations, the system automatically determines the updated location information 1902 by providing the predicted shape of the target lesion 1704 and/or at least a portion of the initial location information 1706 as modified by the user (e.g., specifying "Lymph Node") as input to a machine learning module 120 to cause the machine learning module 120 to identify updated the location information 1902 for the lesion 1704. Put differently, at least a portion of the user modifications to the initial location information 1706 may act as an additional constraint or input for the identification process performed by the machine learning module 120 to determine the updated location information 1902.

In the example shown in FIG. 19, based at least in part on the received user input (e.g., specifying "Lymph Node"), the system generates the updated location information 1902 for the target lesion 1704, including an indication region 1904 that the target lesion 1704 is a lymph node, an indication region 1906 that the target lesion 1704 is in the abdomen of the patient, an indication 1908 that the target lesion 1704 is in the mesenteric region of the abdomen, and an indication region 1910 allowing the user to further select from among "small bowel," "colon," or "sigmoid." After determining that the updated location information 1902 is desirable/acceptable (whether additional modifications are performed or not), the user may choose to accept the updated location information 1902 (e.g., by selecting the check mark button in the upper-left region).

Upon establishing location information for a lesion, whether in fully automated or partially automated fashion, the system may associate the location information with the lesion represented in the cross-sectional medical image and/or with the cross-sectional medical image itself (e.g., at least partially utilizing data processing module(s) 114), thereby allowing the location information to be used for lesion analysis.

Figure 20:
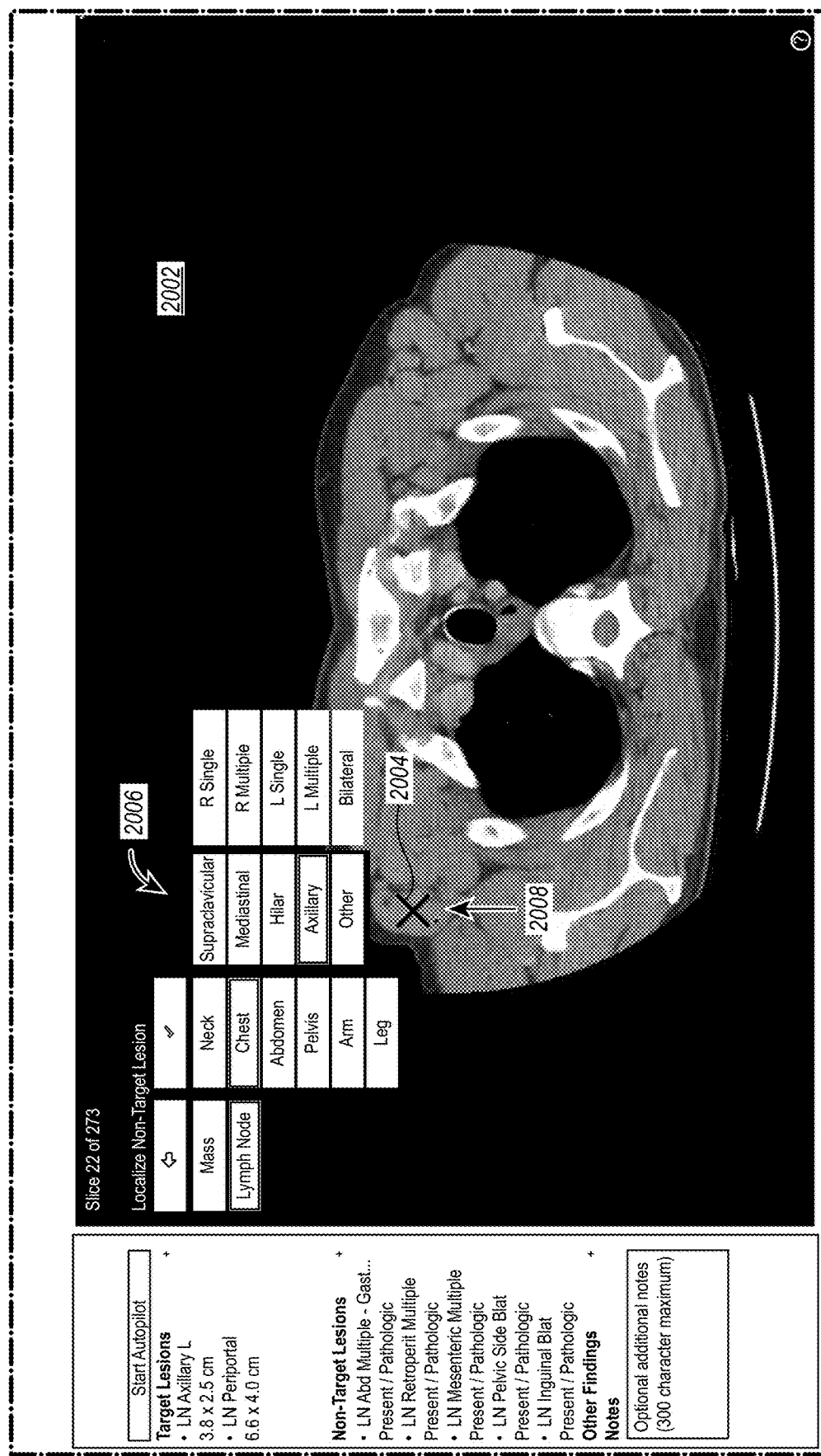
FIG. 20 illustrates an example of a display interface rendering associated with a system for facilitating lesion analysis as the system provides a lesion marker and location information for a non-target lesion based on received user input, according to the present disclosure.

Although FIGS. 2-19 have focused, in at least some respects, on analysis of target lesions, it will be appreciated that at least some of the principles disclosed herein are applicable to non-target lesions or other findings as well. For instance, FIG. 20 illustrates an example of a display interface rendering associated with a system for lesion analysis as the system displays a cross-sectional image 2002 (slice 22 of 273) and illustrates a lesion marker 2004 and location information 2006 for a non-target lesion 2008 based at least in part on received user input. For instance, in the example shown, the system received user input electing to identify a non-target lesion and user input directed to another axillary lymph node (e.g., user input selecting a pixel region associated with the non-target lesion 2008). The system, in response, may utilize coordinate information associated with user input selecting the non-target lesion (or the pixel region within the non-target lesion 2008) and/or other information (e.g., image slice number) to generate location information 2006 for the non-target lesion 2008. In some instances, the system identifies a predicted shape associated with the selected non-target lesion 2008 to generate the location information 2006 at least in part based on the predicted shape. In the depicted example, the system presents the location information 2006 indicating that the non-target lesion 2008 is a lymph node located in the axillary region of the chest and prompts the user to accept or modify the location information.

As shown, the system refrains from rendering the predicted shape or any minor and/or major axes that could be derived therefrom overlaid on the cross-sectional medical image 2002 (e.g., to facilitate faster analysis of non-target lesions). Rather than minor and/or major axes and/or predicted shape/segmentation information, the system simply provides the lesion marker 2004 in the form of an "X" over the non-target lesion 2008 to indicate the location of the non-target lesion 2008 within the cross-sectional image 2002 (e.g., for review at subsequent timepoints, as discussed hereinafter). In addition, in at least some instances, the system provides less granular location information for non-target lesions than it does for target lesions, and the system may provide location information that generalizes at least some location details for non-target lesions (e.g., to facilitate faster analysis of non-target lesions). Accordingly, those skilled in the art will recognize that machine learning module(s) 120 and/or other components of the present disclosure may include different algorithms for identifying location information for target lesions and non-target lesions.

Figure 21:
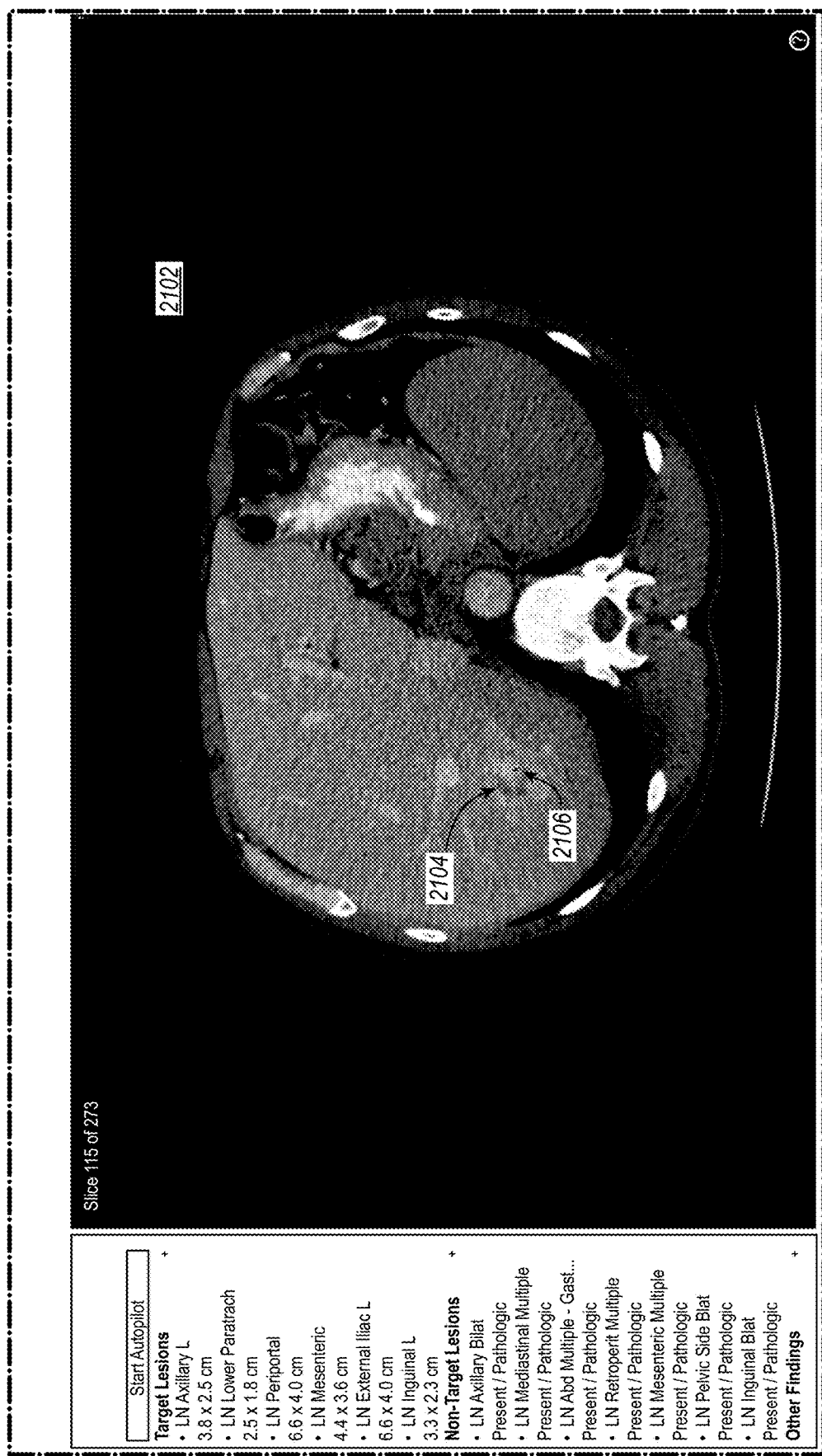
FIG. 21 illustrates an example of a display interface rendering associated with a system for facilitating lesion analysis as the system displays a cross-sectional image including a representation of a lesion that is not a target lesion or a non-target lesion; according to the present disclosure
Figure 22:
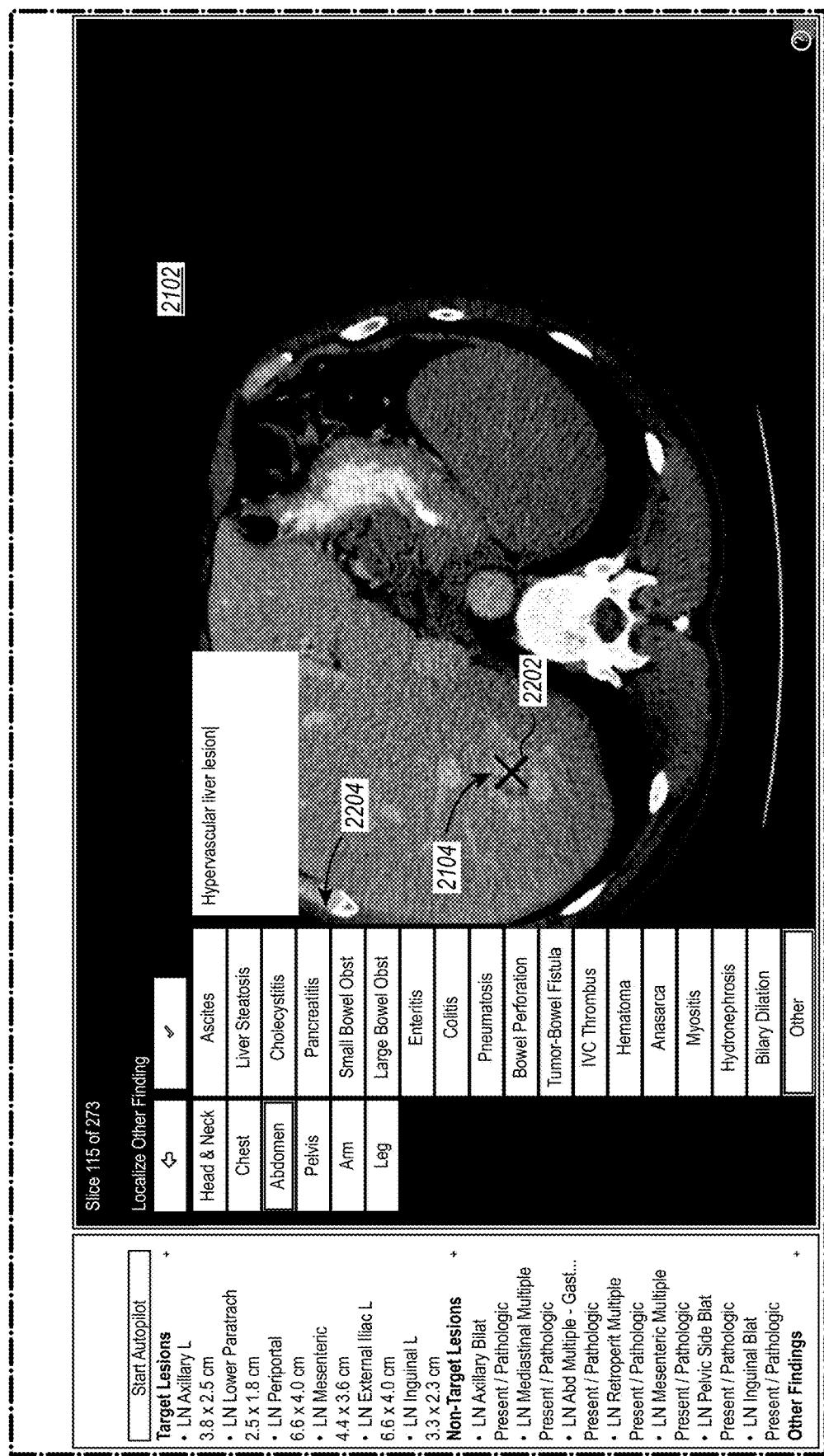
FIG. 22 illustrates an example of a display interface rendering associated with a system for facilitating lesion analysis as the system provides a lesion marker and location information for the lesion that is not a target lesion or a non-target lesion based on received user input, according to the present disclosure.

In some implementations, the system is configured to track lesions or other findings aside from target and non-target lesions. For instance, FIG. 21 illustrates an example of a display interface rendering as the system displays a cross-sectional image 2102 (slice 115 of 273) including a representation of a lesion 2104 that is not a target lesion or a non-target lesion. The mouse cursor 2106 is positioned over the lesion 2104 of interest. FIG. 22 illustrates an example of a display interface rendering as the system displays a lesion marker 2202 and location information 2204 for the lesion 2104 of interest shown in FIG. 21. The lesion marker 2202 may positionally correspond with the user input received selecting/identifying the lesion of interest (e.g., selection of a pixel region within the cross-sectional image 2102), and the location information 2204 may be entirely provided by user input (e.g., utilizing selectable buttons or providing text input, as shown in FIG. 22). Providing functionality for identifying a lesion of interest that is not a target lesion or a non-target lesion may allow for reviewers to force subsequent reviewers to review such lesions of interest, which may provide a more comprehensive lesion analysis over multiple timepoints.

In some embodiments, the system is configured to prompt the user to characterize the other finding(s) according to established clinical guidelines for indeterminate or incidental findings from literature, a clinical or radiologic society, or published national or international guidelines. Examples may include characterizing other findings according to the American College of Radiology (ACR) Reporting and Data Systems (ACR RADS) including BI-RADS, C-RADS, HI-RADS, LI-RADS, Lung-RADS, NI-RADS, O-RADS, PI-RADS, or TI-RADS. For example, the system may prompt the user to characterize a lung nodule per Lung-RADS or by other methods such as Fleischner Criteria. The system may prompt the user to characterize any incidental finding using established criteria or methods known in the art. For example, the system could prompt the user to characterize an adrenal nodule following guidelines from the ACR Incidental Finding Committee, including white papers from a society or established group of experts. Furthermore, the system could assist the user by providing recommendations on follow up or management of the incidental findings using these same or newly established guidelines.

As noted above, information related to lesion location, predicted lesion shape/segmentation, lesion axes, lesion pixel area, slice location or image number of the cross-sectional image depicting the lesion, and/or other lesion metrics may be stored (e.g., utilizing data processing module(s) 114) in computer-readable storage (e.g., within hardware storage device(s) 112, primary database 116, etc.). Such information may be stored in any suitable form, such as a series of entries in a list or other data structure.

In some implementations, the system is configurable to display representations of the stored lesion information contemporaneously with cross-sectional images of the set of cross-sectional images that include the analyzed lesions.

Figure 23:
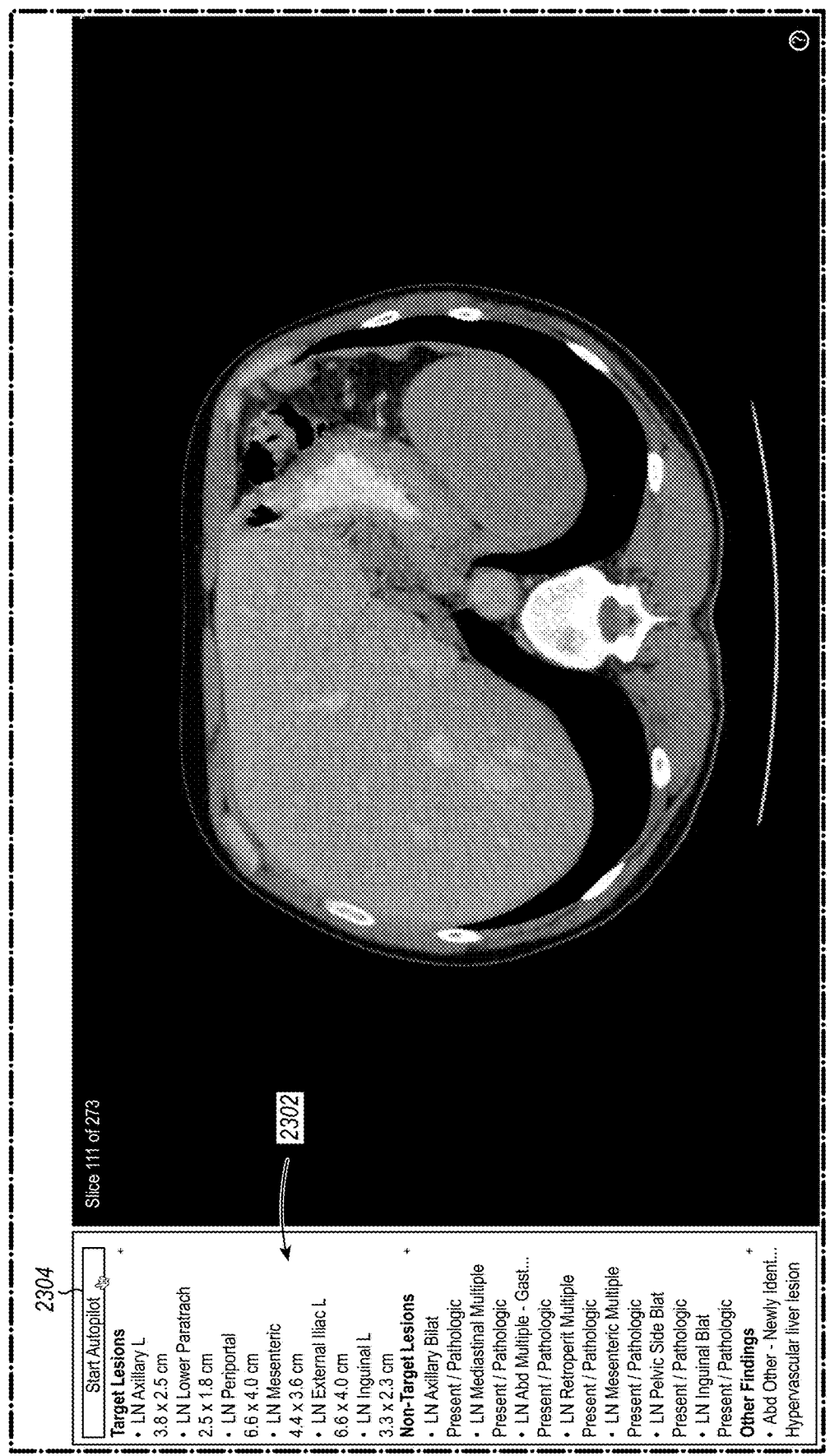
FIG. 23 illustrates an example of a display interface rendering associated with a system for facilitating lesion analysis as the system provides a list of analyzed lesions within a plurality of cross-sectional medical images, according to the present disclosure.

FIG. 23 illustrates an example of a display interface rendering as the system provides a rendering of a list 2302 of information related to analyzed lesions within the plurality of cross-sectional medical images along a left side of the user interface. As shown, the list 2302 includes at least some information for analyzed lesions, such as abbreviations indicating location information for each lesion and/or the length of axes (if any) associated with each lesion. The list 2302 may persist within the user interface during lesion analysis and may be dynamically updated in real time to reflect newly identified/classified/labeled lesions.

In some instances, the system provides functionality for a guided presentation of the tracked lesions, and this guided presentation may be driven at least in part by the representations of the stored lesion information (e.g., for error checking purposes or to check the lesion analysis of another reviewer). Providing a guided presentation of analyzed lesions may greatly expedite processes for reviewing the user's own lesion analysis or the lesion analysis of other reviewers, particularly where several lesions were analyzed in one or more sets of cross-sectional images. Providing a guided presentation of analyzed lesions may also expedite processes for performing lesion analysis on cross-sectional images taken at different timepoints, as described hereinafter. In the example list 2302 shown in FIG. 23, the user may initiate the guided presentation of the analyzed lesions by providing user input selecting the "Start Autopilot" button 2304 in the user interface.

Figure 24:
FIGS. 24-26 illustrate examples of display interface renderings associated with a system for facilitating lesion analysis as the system provides a guided presentation of the analyzed lesions within the plurality of cross-sectional images, according to the present disclosure.
Figure 25:
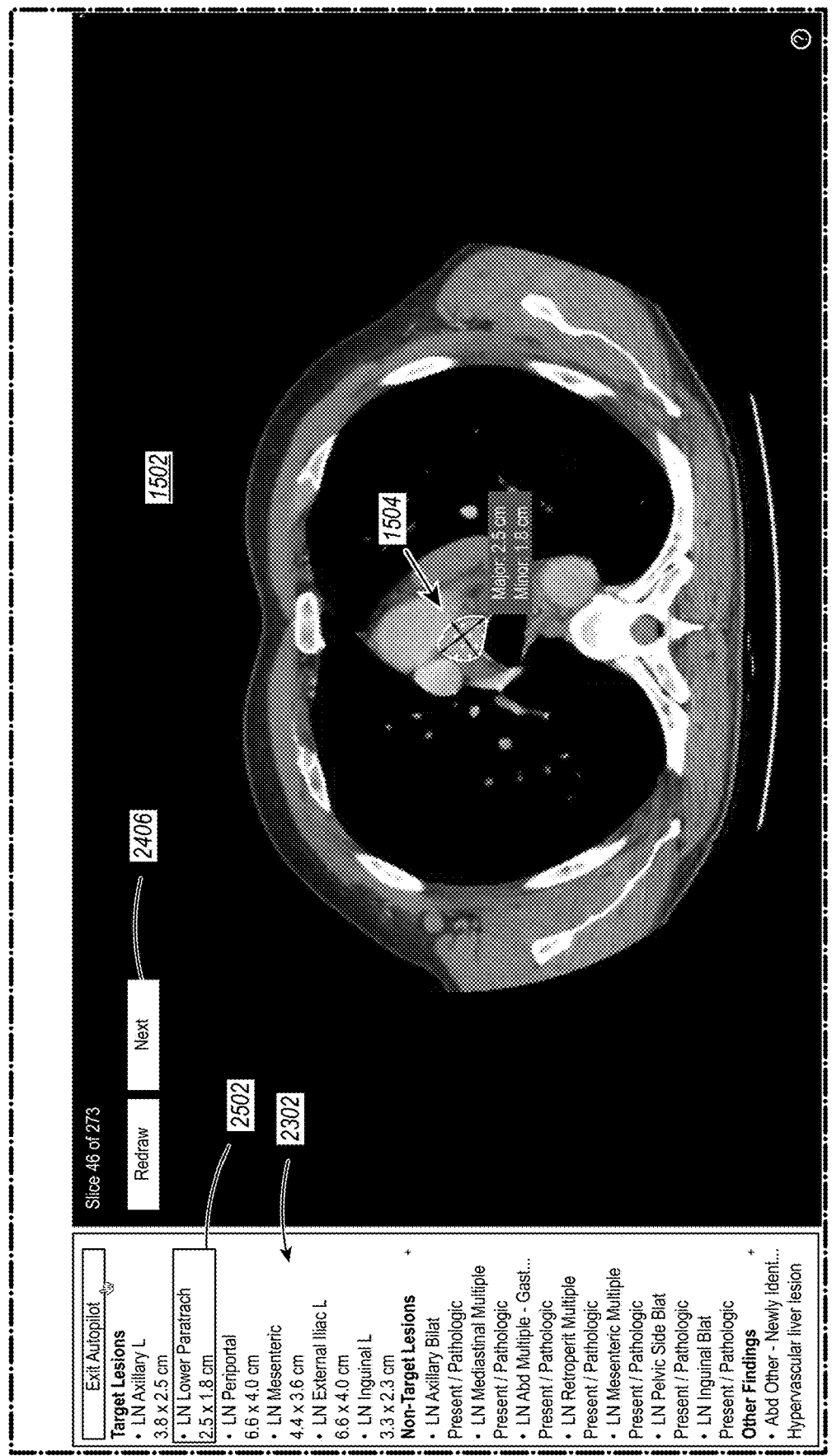
Figure 26:

FIGS. 24-26 illustrate examples of display interface renderings as the system provides a guided presentation of the analyzed lesions within the plurality of cross-sectional images. In the example shown in FIG. 24, the user has provided the user input indicated in the description of FIG. 23 (i.e., selecting the "Start Autopilot" button 2304), and the system, in response, has navigated to the cross-sectional image 302 corresponding to the first entry 2402 in the list 2302 of analyzed lesions shown in the left side of the user interface. As shown, the first entry 2402 corresponds to the segmented axillary target lesion 404 shown and described with reference to FIGS. 6-8 and 14 hereinabove, so the system navigates to the cross-sectional image 302 that depicts the segmented axillary target lesion 404 and renders the applicable cross-sectional image 302 with the lesion predicted shape and major and minor axes overlaid on the target lesion 404 represented in the cross-sectional image 302 (major and/or minor axes associated with a lesion, whether a target lesion, a non-target lesion, or other finding, may be regarded as "lesion marker(s)"). Accordingly, a reviewer may quickly navigate to the first analyzed lesion within the set of cross-sectional images.

FIG. 24 shows that the user interface displayed may include functionality for readily allowing a reviewer to modify lesion information that has been stored in or in association with the list 2302. For instance, the user interface shown in FIG. 24 includes a "Redraw" button 2404, which may allow a reviewer to discard or modify lesion predicted shape and/or lesion location information associated with the list 2302. Such functionality may allow a reviewing physician to review lesion analysis performed previously (e.g., whether by the same reviewer or another reviewer) in a rapid and/or efficient manner. A user interface may also include functionality for discarding one or more entries of the list 2302.

FIG. 24 also shows that in some instances, during a guided presentation of analyzed lesions, the user interface provides controls for navigating to a next cross-sectional image in the list 2302 that includes an analyzed (or marked) lesion, as indicated by the "Next" button 2406. Accordingly, a user may provide input for navigating to and rendering a next cross-sectional image within the set of cross-sectional images for the particular patient that includes an analyzed or tracked lesion (e.g., as recorded in the list 2302). A user interface may also include a button or other interface element for navigating to a previous cross-sectional image that includes an analyzed (or marked) lesion (e.g., as recorded in the list 2302).

FIG. 25 shows a display interface rendering provided by the system after receiving user input activating a control for navigating to the next cross-sectional medical image in the list 2302 that includes a marked lesion (e.g., by selecting the "Next" button 2406). In response, the system navigates to and displays the next cross-sectional medical image that includes a marked lesion corresponding to the second entry 2502 in the list 2302, along with any applicable segmentation/axis data associated with the analyzed lesion. In the instance shown in FIG. 25, the second entry 2502 in the list 2302 is associated with the segmented mediastinal target lesion 1504 shown and described with reference to FIGS. 15-16.

In some instances, the system may provide functionality for allowing the user to navigate directly to any cross-sectional image associated with the list 2302 containing an analyzed lesion. For instance, a system may be configured to receive user input that selects one of the entries of the list 2302 (e.g., which entries may comprise representations of stored lesion metrics/data/images). Such user input may comprise navigating a mouse cursor over and selecting one of the entries of the list 2302, as shown in FIG. 26, which shows an icon 2602 positioned over and selecting an entry 2604 of the list 2302. The entry 2604 of the list 2302 selected in FIG. 26 comprises a representation of the stored data/information (e.g., location information, cross-sectional image, location within the cross-sectional image, etc.) associated with the axillary non-target lesion 2008 shown and described with reference to FIG. 20.

In response to the user input selecting entry 2604 of the list 2302, the system renders and presents the non-target lesion 2008 with the lesion marker 2004 (e.g., an "X" marker) indicating the location of the non-target lesion 2008 within the cross-sectional image 2002. It will be appreciated that the direct navigation described herein with reference to FIG. 26 may also be applied to selections of entries of the list 2302 that are associated with target lesions or other lesions/findings, as well as non-target lesions, and the system may, in some instances, display additional or different information associated with such lesions (e.g., segmentation information, major and/or minor axes, etc.).

Figure 27:
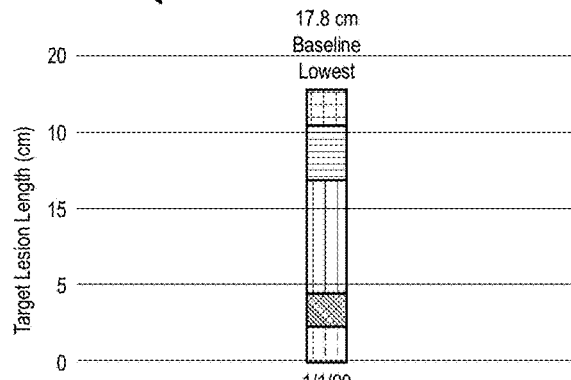
FIG. 27 illustrates an example of a display interface rendering associated with a system for facilitating lesion analysis as the system provides a report based on the analyzed lesions within the plurality of cross-sectional images, according to the present disclosure.

In some embodiments, in addition to providing functionality for a guided presentation of analyzed lesions, the system may also utilize the stored lesion metrics, data, and/or information (e.g., associated with entries of the list 2302) to generate reports. Such reports may be used, for instance, for oncological and/or patient review. FIG. 27 illustrates an example of a display interface rendering as the system provides report 2702 based on the analyzed lesions within the plurality of cross-sectional images. The report includes various information, such as a listing of target lesions 2704 (including composite length metrics for the target lesions), a listing of non-target lesions 2706, and a listing of other findings 2708, as well as information for each class of analyzed lesion (e.g., axis length for target lesions, status for non-target lesions, notes related to other findings, etc.).

The report 2702 of FIG. 27 also includes a graphical representation 2710 illustrating the composite length of the analyzed target lesions. The composite length may comprise a summation of various lengths of various analyzed target lesions. As noted above, a target lesion may have a minor axis and a major axis associated therewith, and the system may select from among the minor and major axes for contribution to the composite length depending on the tumor response criteria (e.g., under some tumor response criteria, the system may select minor axes for lymph nodes, and major axes for masses). The report 2702 also includes an indication of the tumor response criteria that informs the data/analysis provided in the report 2702, and reports may vary in form and/or content based on the tumor response criteria selected or applicable.

The report 2702 shown in FIG. 27 is related to lesion analysis performed for lesions present in cross-sectional images of a patient associated with a single timepoint (e.g., a single imaging session). The report 2702 also includes information showing the reader who performed the lesion analysis, as well as a date for the analysis or the imaging. Additional details concerning lesion analysis reports, including reports involving lesions analyzed at multiple timepoints and/or by multiple readers, will be provided hereinafter. Additional information could be added to the report including clinical history or a research study identification number.

Figure 28:
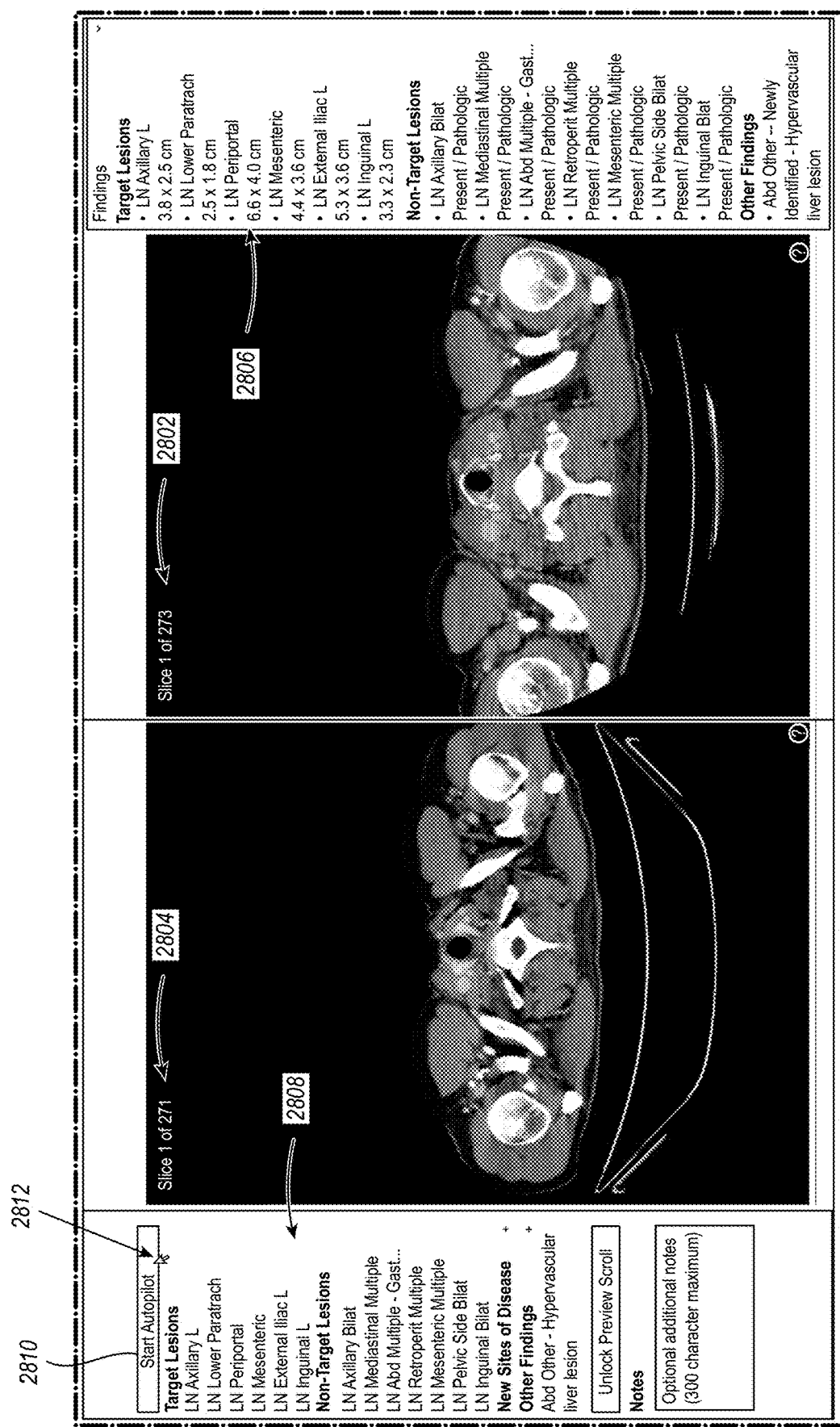
FIG. 28 illustrates an example of a display interface rendering associated with a system for facilitating lesion analysis as the system provides different sets of cross-sectional images captured at different timepoints, according to the present disclosure.

As mentioned with reference to FIG. 1, the system may facilitate lesion analysis of the same lesions over multiple timepoints to track objective tumor response over time in a manner that improves efficiency and/or reduces read times. FIG. 28 illustrates an example of a display interface rendering as the system provides different sets of cross-sectional images for a particular patient captured at different timepoints. In FIG. 28, the first cross-sectional image set 2802 shown on the right portion of the user interface of FIG. 28 corresponds to previous-timepoint cross-sectional images with lesion analysis already performed on at least some of the previous-timepoint cross-sectional images. The second cross-sectional image set 2804 shown on the left portion of the user interface of FIG. 28 corresponds to later-timepoint cross-sectional images. In the example shown in FIG. 28, the different sets of cross-sectional images 2802 and 2804 are displayed simultaneously such that the user can navigate through either set by manipulating I/O device interface(s) 106.

In some instances, the system accesses a database that includes entries with information associated with the previously analyzed lesions (e.g., location information/labeling, shape/segmentation, major and/or minor axes, pixel area, slice location, etc.) and may display one or more lists including representations of the information stored in the database. For instance, the system may render a first list 2806 associated with the previous-timepoint cross-sectional images (the first set of cross-sectional images 2802) to facilitate guided presentation functionality similar to the functionality described hereinabove with reference to FIGS. 23-26. In some instances, the system simultaneously presents a second list 2808 associated with the later-timepoint cross-sectional images (the second set of cross-sectional images 2804) that includes at least some of the information from the database with information for the previously analyzed lesions. For instance, because, in the example shown, the same lesions are analyzed over time to measure objective tumor response, the location information/labeling associated with previously analyzed lesions of the previous-timepoint cross-sectional images (the first set of cross-sectional images 2802) will be the same as the currently analyzed lesions in the later-timepoint cross-sectional images (the second set of cross-sectional images 2804). Accordingly, the location information shown in both the first list 2806 and the second list 2808 may be the same.

The second list 2808 shown in FIG. 28 in connection with the later-timepoint cross-sectional images (the second set of cross-sectional images 2804) may also be associated with a different database (or a different portion of the same database as the database that stores the information associated with the previously analyzed lesions) for storing information associated with the lesions as represented in the later-timepoint cross-sectional images, as will be now described below. Because the same lesions are analyzed over time, as noted above, location information of the previous-timepoint lesion analysis entries may be copied from the previous-timepoint database entries into the later-timepoint database entries for the later-timepoint lesion analysis.

Certain aspects and/or features of the guided presentation described hereinabove referring to FIGS. 23-26 may also apply in later-timepoint analysis of previously analyzed lesions, as depicted in FIGS. 28-33. For instance, a user may select a control (e.g., a "Start Autopilot" button 2810, as shown in FIG. 28) to initiate a guided analysis of lesions represented in the second set of cross-sectional images 2804 based at least in part on information associated with the previously analyzed lesions (e.g., represented in the first list 2806). FIG. 28 illustrates a user control icon 2812 positioned over the "Start Autopilot" button 2810, which may initiate a guided analysis of the lesions represented second list 2808 associated with the second set of cross-sectional images 2804 (e.g., the later-timepoint cross-sectional images), where the lesions represented in the second list 2808 correspond to the lesions represented in the first list 2806 (e.g., associated with the first set of cross-sectional images 2802).

In response to detecting user input associated with initiating a guided analysis of the later-timepoint lesions of the second list 2808 (whether by selecting a dedicated button for this purpose or by selecting an entry of one of the lists), the system may utilize various components (e.g., image processing module(s) 110, machine learning module(s) 120), etc.) to identify one or more later-timepoint cross-sectional images of the second set of cross-sectional images 2804 that correspond to one or more previous-timepoint cross-sectional images of the first set of cross-sectional images 2802. Such functionality may be carried out to identify a predicted matching cross-sectional image from the second set of cross-sectional images 2804 that matches a previous-timepoint cross-sectional image of the first set of cross-sectional images 2802. Cross-sectional images from the different sets of cross-sectional images may be regarded as "matching" when they both include substantially similar representations of structures of the body of the patient, include any lesions represented therein.

Providing such functionality may expedite the process of locating a later-timepoint cross-sectional image (from the second set of cross-sectional images 2804) that includes a representation of a lesion that is also represented in (and previously analyzed according to) a previous-timepoint cross-sectional image (from the first set of cross-sectional images 2802). The image processing module(s) 110 may utilize any suitable technique(s) for identifying a predicted matching cross-sectional image, such as image co-registration and/or other methods.

Figure 29:
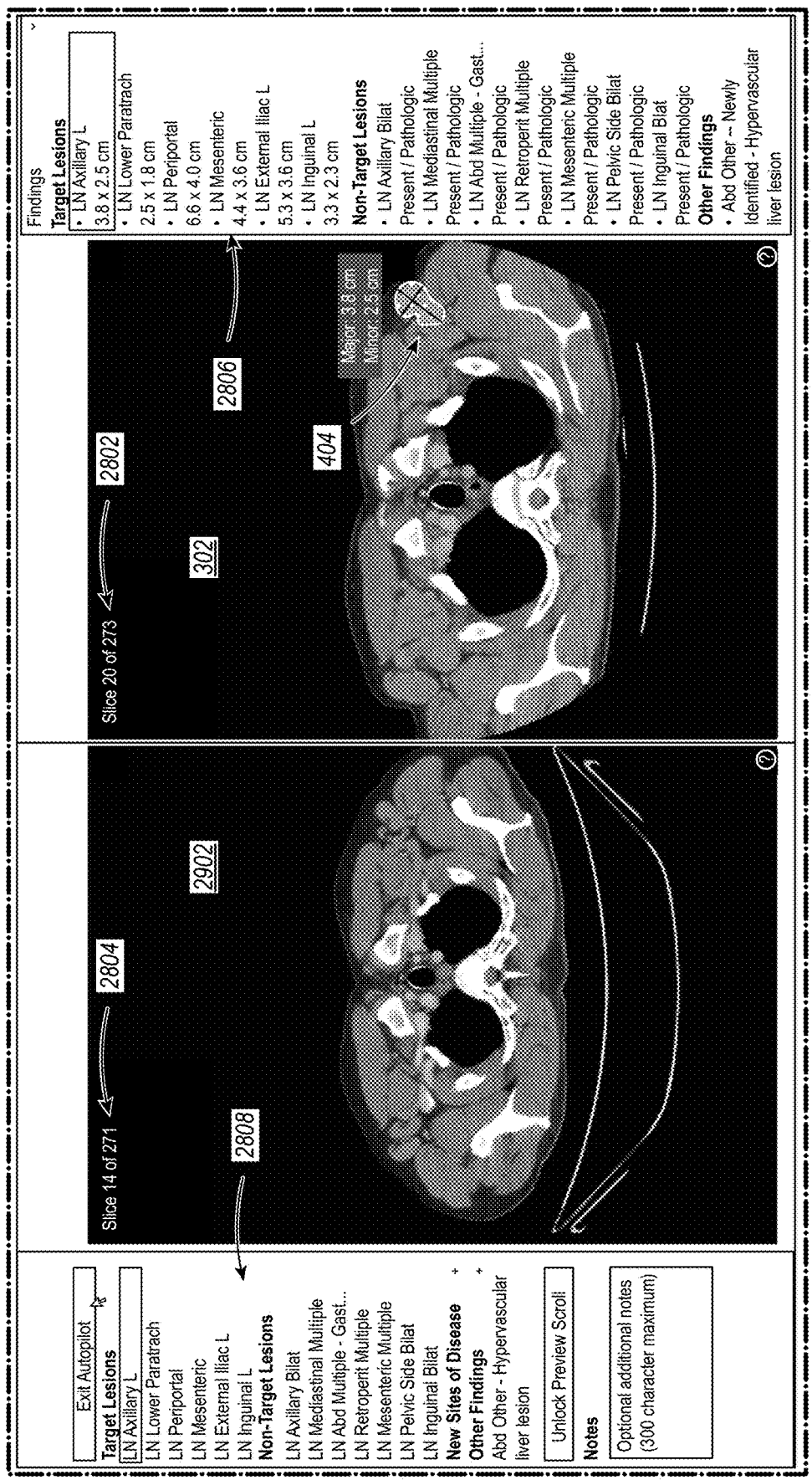
FIG. 29 illustrates an example of a display interface rendering associated with a system for facilitating lesion analysis as the system provides a predicted matching cross-sectional image that attempts to find a matching target lesion that corresponds to a previously analyzed target lesion, according to the present disclosure.

FIG. 29 illustrates an example of a display interface rendering as the system provides a predicted matching cross-sectional image that attempts to find a matching target lesion that corresponds to a previously analyzed target lesion. In FIG. 29, the system detected user input initiating the guided analysis of the second set of cross-sectional images 2804 based on information associated with previously analyzed lesions (represented in the first list 2806). In other instances, the system may initiate or continue guided analysis in response to receiving user input for navigating to a next cross-sectional image associated with an analyzed lesion, or the system may receive user input directed to a particular list entry of one of the lists.

In any case, in response to the received user input, the system may identify a particular list entry of the first list 2806 and may display the previous-timepoint cross-sectional image from the first set of cross-sectional images 2802 that is associated with the lesion represented in the particular list entry. For example, FIG. 29 shows the system responding to user input directed toward the first entry of the first list 2806, which is associated with the axillary target lesion 404 shown and described referring to FIGS. 6-8, 14, and 24. Accordingly, the system may display the axillary target lesion 404 as represented in the appropriate previous-timepoint cross-sectional image 302, and the system may also display an overlay of the segmentation and axes associated with the axillary target lesion 404.

FIG. 29 also shows that the system has identified a predicted matching later-timepoint cross-sectional image 2902 that may include a later timepoint representation of the axillary lesion 404 previously analyzed. In the example of FIG. 29, the system automatically navigates to and displays slice 14 of 271 of the second set of cross-sectional images 2804 (as indicated over the upper-left hand region of the left side of the user interface) in response to the user input described above for initiating or continuing the guided analysis of the second set of cross-sectional images 2804. As noted above, the system may identify slice 14 as a predicted matching cross-sectional image 2902 by image co-registration or another method utilizing image processing module(s) 110 and/or machine learning module(s) 120.

As shown in FIG. 29, the predicted matching cross-sectional image 2902 is displayed contemporaneously with the previous-timepoint cross-sectional image 302 showing the previously analyzed axillary target lesion 404. The contemporaneous presentation of these cross-sectional images may allow the user to rapidly assess the similarity between the predicted matching later-timepoint cross-sectional image 2902 and the previous-timepoint cross-sectional image 302 to determine whether to modify the later-timepoint cross-sectional image (e.g., navigate to a different, neighboring slice) before performing lesion analysis on the later-timepoint representation of the target lesion that was previously analyzed.

Figure 30:
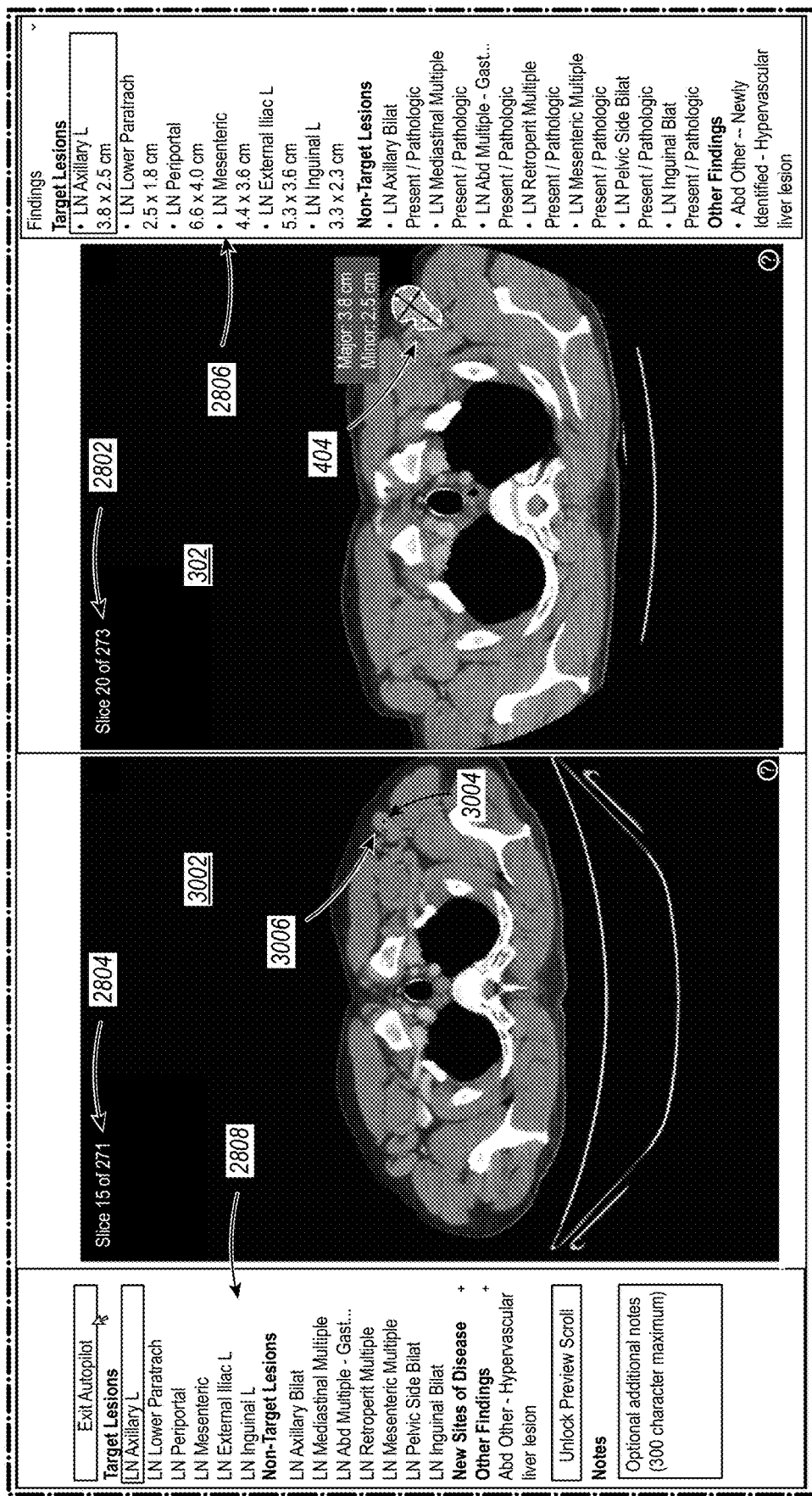
FIG. 30 illustrates an example of a display interface rendering associated with a system for facilitating lesion analysis as the system displays a modified predicted matching cross-sectional image after receiving user input modifying the predicted matching cross-sectional image, according to the present disclosure.

FIG. 30 illustrates an example of a display interface rendering as the system displays a matching cross-sectional image 3002 after receiving user input modifying or navigating away from the initial predicted matching cross-sectional image 2902. In FIG. 30, the user has provided user input modifying or navigating away from the predicted matching later-timepoint cross-sectional image 2902 by navigating to slice 15 of the second set of cross-sectional images 2804 rather than slice 14 of the second set of cross-sectional images 2804. Even with this user-directed change, the automated prediction of a matching cross-sectional image from the second set of cross-sectional images 2804 may bring the user within close range to an optimal matching later-timepoint cross-sectional image, so the disclosed systems may improve read times even without always predicting the best matching cross-sectional image.

With the matching later-timepoint cross-sectional image selected, the system may facilitate lesion analysis on the later-timepoint representation of the lesion that corresponds to the previously analyzed lesion. As shown in FIG. 30, a user control icon 3004 is positioned over a matching lesion 3006 in the later-timepoint matching cross-sectional image 3002 that corresponds to the axillary target lesion 404 previously analyzed and shown in the displayed previous-timepoint cross-sectional image 302. The user may thereafter select a pixel or pixel patch within the later-timepoint lesion (e.g., the matching lesion 3006) to begin lesion analysis thereon.

Figure 31:
FIG. 31 illustrates an example of a display interface rendering associated with a system for facilitating lesion analysis as the system determines shape and location information for the matching target lesion, according to the present disclosure.

FIG. 31 illustrates an example of a display interface rendering as the system determines shape and location information for the matching target lesion 3006. The system may implement any of the operations, functions, and/or processes described hereinabove with reference to FIGS. 1-22 to determine shape and/or location information associated with the matching lesion 3006. For instance, the system may utilize image processing module(s) 110 and/or machine learning module(s) 120 to determine a predicted shape 3102 or segmentation associated with the matching lesion 3006. The user may also modify the segmentation as described above. The system may associate a matching lesion marker 3104 (e.g., implemented as a simple "X" or other symbol for non-target lesions or other findings, or a major axis and/or a minor axis rendering for target lesions) with the matching lesion 3006 and store the matching lesion marker 3104 within the database associated with the matching lesion 3006 and/or the cross-sectional image 3002. The segmentation and/or other information for the matching lesion 3006 may also be stored. Furthermore, the system may display lesion marker, predicted shape, and/or other information associated with the matching lesion 3006 and the previously analyzed lesion 404 simultaneously within and/or overlaid on their respective cross-sectional images (3002 and 302, respectively).

It should be noted that the foregoing functionality associated with the guided analysis of lesions represented in later-timepoint second set of cross-sectional images 2804 may be applied to target lesions (as described in FIGS. 29-31), non-target lesions, and/or other lesions/findings. For instance, FIG. 32 illustrates an example of a display interface rendering as the system displays a matching cross-sectional image 3202 that matches a prior-timepoint cross-sectional image 2002 that includes a representation of a previously analyzed non-target lesion 2008 (e.g., as described with reference to FIG. 20). The previously analyzed non-target lesion 2008 corresponds to the first non-target lesion entry of the first list 2806. The system determines and/or displays a lesion marker 3206 for a matching non-target lesion 3204 of the matching cross-sectional image 3202 that corresponds to the previously analyzed non-target lesion 2008. The lesion marker 3206 may be determined at least partially based on user input (e.g., input directed toward a pixel region in the matching cross-sectional image 3202.

In some instances, for non-target lesions, the system may refrain from obtaining segmentation and/or axis information associated with the matching non-target lesion 3204. For instance, as shown in FIG. 32, the system may prompt the user to qualitatively analyze the matching non-target lesion 3204 and rapidly provide input identifying whether the matching non-target lesion 3204, as compared with the previously analyzed non-target lesion 2008, is absent or not, present or pathologic, has exhibited unequivocal progression, or was not evaluated. To facilitate rapid analysis/input, the system may provide buttons 3208 corresponding to the non-target lesion classifications noted above, including a "Absent/Not Pathologic" button, "Present/Pathologic" button, an "Unequivocal Progression" button, or a "Not Evaluated" button. Such user input for non-target lesions may also become stored in a database associated with analysis for later-timepoint lesions.

Similarly, FIG. 33 illustrates an example of a display interface rendering as the system displays a matching cross-sectional image 3302 that matches a prior-timepoint cross-sectional image 2102 that includes a representation of a previously analyzed lesion 2104 that is not a target or non-target lesion (as described with reference to FIGS. 21 and 22). The previously analyzed lesion 2104 is noted in the portion of the first list 2806 dedicated to "Other Findings." The system determines and/or displays a lesion marker 3306 for a matching lesion 3304 that is not a target lesion or a non-target lesion and that corresponds to a previously analyzed lesion 2104 that was not a target lesion or a non-target lesion. The lesion marker 3306 may be determined at least partially based on user input (e.g., input directed toward a pixel region in the matching cross-sectional image 3302).

Upon receiving user input identifying the location of the lesion in the predicted matching later-timepoint cross-sectional image, the system may prompt the user to indicate whether the lesion is "Resolved," "Improved," "Unchanged," "Worsened," or "Not Evaluated" via one or more buttons 3308. Such user input for the lesion 3304 may also become stored in a database associated with analysis for the matching lesion 3304.

As indicated hereinabove, the system may provide functionality for organizing and/or compiling the information stored for one or more lesions at one or more timepoints to generate oncological and/or patient reports. FIG. 34 illustrates an example of a display interface rendering as the system provides a summary report 3402 based on multiple lesions analyzed at different timepoints. The summary report 3402 may indicate the criteria under which the summary report 3402 was generated (e.g., "Freeform RECIST"), a generalization of the treatment response based on the lesion metrics determined for the analyzed lesions ("Stable Disease"), as well as various charts and/or tables indicating lesion metrics for lesions analyzed over one or more different timepoints.

For instance, the summary report 3402 provides a listing of target lesions 3404 that includes information associated with the target lesions analyzed over multiple timepoints. For example, the listing of target lesions 3404 of the summary report 3402 includes indications of the various anatomical locations of the analyzed target lesions as well as indications of the most recently measured major and minor axis length for the analyzed target lesions. As shown in FIG. 34, the listing of target lesions 3404 also includes a summary that provides useful metrics for the analyzed target lesions, such as the current sum of the axis lengths of the analyzed target lesions (which may include major axes, minor axes, or a combination) and/or changes in the sum of axis lengths over various timepoints (e.g., change relative to the baseline or measurements associated with a first timepoint, changes relative to the lowest sum found, changes relative to a sum associated with a prior timepoint, etc.).

The summary report 3402 of FIG. 34 also includes a listing of non-target lesions 3406 that may include lesion location information for analyzed non-target lesions and/or determined response for analyzed lesions, such as whether the non-target lesion is present/pathologic, absent/non-pathologic, is unequivocally progressing, and/or not evaluated (e.g., according to user input provided under longitudinal analysis of non-target lesions over multiple timepoints, as shown in FIG. 32).

The summary report 3402 of FIG. 34 also includes a listing of other findings 3408, which may include lesions or other findings that were tracked during analysis of cross-sectional images for a patient (e.g., as shown in FIGS. 21-22 and 33). Such lesions may comprise items of interest found that do not squarely fit within a tumor response criterion, but that reviewers believe are relevant to the wellbeing of the patient. The listing of other findings 3408 may include identifying information for the other findings provided during analysis of the other findings, as well as further action that should be taken.

FIG. 34 also illustrates that the summary report 3402 may comprise a graphical representation 3410 illustrating the composite length of the analyzed target lesions according to analysis performed at different timepoints. The composite length may comprise a summation of various lengths of various analyzed target lesions. As noted above, a target lesion may have a minor axis and a major axis associated therewith, and the system may select from among the minor and major axes for contribution to the composite length depending on the tumor response criteria (e.g., under some tumor response criteria, the system may select minor axes for lymph nodes, and major axes for masses). The graphical representation 3410 may provide users with an intuitive representation of tumor progression and/or treatment response.

The summary report 3402 may also comprise other information, such as whether new sites of disease have been identified (e.g., in a most recently performed analysis of cross-sectional images for a patient), as well as a report information section 3412. New sites of disease could be characterized as possible or definite. The report information section 3412 may comprise various types of information related to the report, such as the date the report was generated and/or an intended audience or status of the report, etc. As noted above, any number of specialists may contribute lesion analysis for cross-sectional images associated with a single patient (e.g., for any number of timepoints). Thus, the report information section 3412 of a summary report 3402 may comprise information for one or more readers involved in analyzing the lesions represented in the summary report 3402.

One will understand that the particular layout and/or form of the data represented in the summary report 3402 may be varied in different implementations, and that a summary report 3402 may comprise any additional or alternative information.

The summary report 3402 may emphasize certain data based on the tumor response criteria and/or other factors associated with the report. For example, in the listing of target lesions 3404, the minor or short axes are highlighted based on the types of target lesions measured (e.g., lymph nodes) in accordance with the criterion used (e.g., Freeform RECIST).

Other types and/or forms of reports are within the scope of this disclosure. For example, FIG. 35 illustrates a detailed table report 3502 based on one or more lesions analyzed at different timepoints and provides detailed lesion information for lesions measured at each timepoint. For instance, whereas the summary report 3402 of FIG. 34 only showed axis length for each target lesion and status classifications for each non-target lesion for the most recently analyzed timepoint, the detailed table report 3502 may show axis length and status classifications for lesions associated with more than one or all analyzed timepoints.

By way of illustration, the target lesion section 3504 of the detailed table report 3502 of FIG. 35 includes information for target lesions analyzed at two different timepoints, such as major and minor axis length, target lesion location and type (e.g., whether lymph node or mass), respective target lesion length sums for each different timepoint, and analysis appertaining thereto (e.g., indicating whether a timepoint provides a baseline sum or a lowest sum, indicating change relative to a baseline sum or a lowest sum, change relative to a prior timepoint, etc.). Furthermore, the non-target lesion section 3506 of the detailed table report 3502 of FIG. 35 may include information for all non-target lesions analyzed over the different timepoints. Also, although not explicitly shown, the detailed table report 3502 may comprise additional details associated with which reader performed analysis on which lesions and may further comprise a section for other findings.

Figure 36:
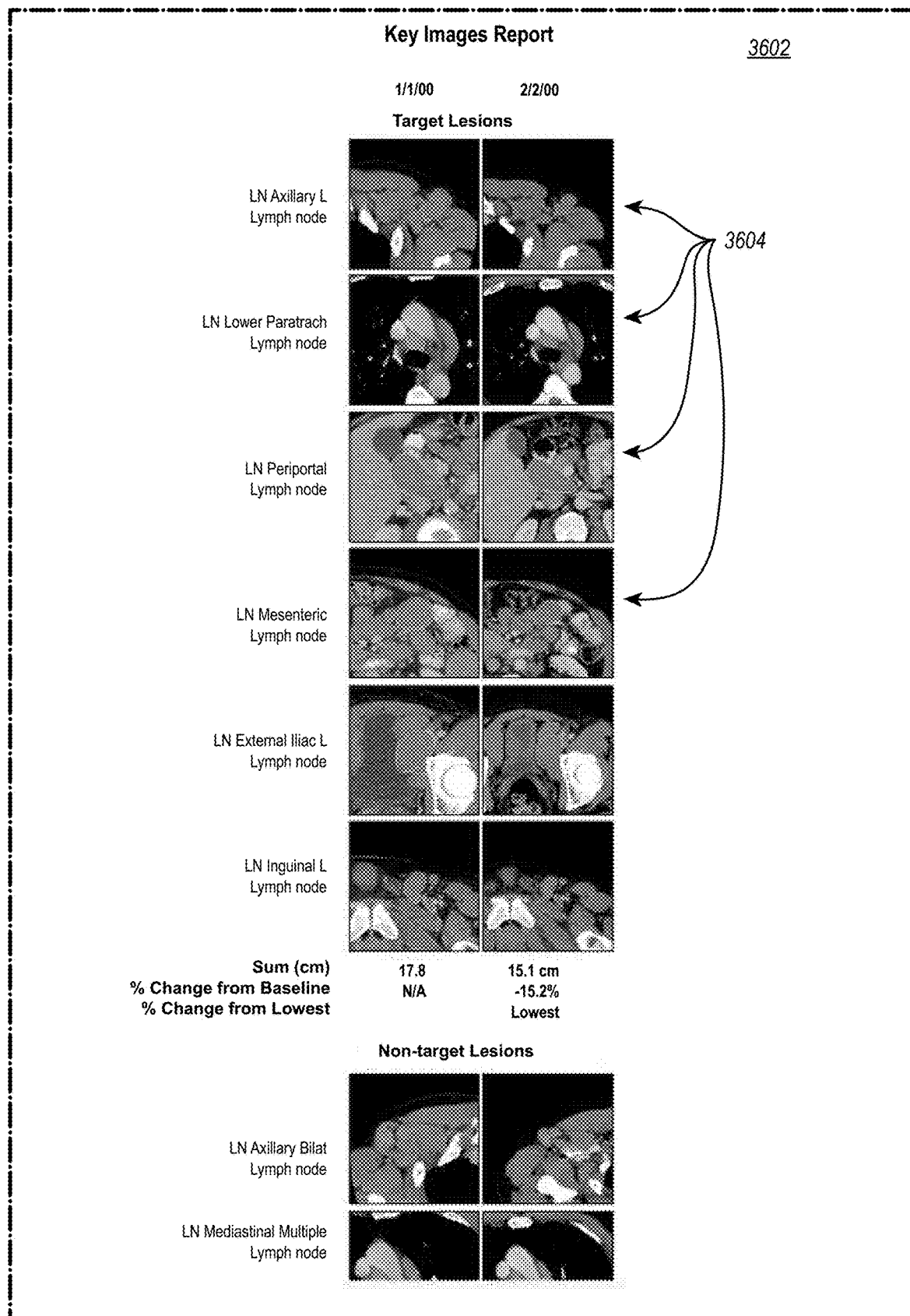
FIG. 36 illustrates an example of a display interface rendering associated with a system for facilitating lesion analysis as the system provides a key image report based on one or more lesions analyzed at different timepoints, according to the present disclosure.

FIG. 36 illustrates an example of a key image report 3602 based on one or more lesions analyzed at different timepoints. The key images 3604 of the key image report 3602 may comprise, as shown in FIG. 36, zoomed views of the analyzed lesions as represented in their respective cross-sectional images. The key images 3604 may include indications and/or highlighting of shape/segmentation and/or lesion markers for the analyzed lesions. As shown, the key images 3604 may be arranged based on timepoint to illustrate progression of the lesions over time (e.g., with treatment), and location information for any lesion may be included in a key image report. For example, different key images 3604 of the same lesion associated with different timepoints may be arranged adjacently to intuitively illustrate progression of the lesion over time for patients and/or practitioners.

Any of the foregoing reports described referring to FIGS. 27 and 34-36 may be used for oncological review, for presentation to a patient, and/or for other purposes. Those skilled in the art will recognize that the form and content of the reports, as well as the particular style and formatting of the user interface renderings shown herein, are provided as examples only and do not limit the scope of the presently disclosed embodiments. For example, the elements of the reports described herein are not exclusive to any particular type of report, and any element of any report may be combined with any other element(s) of any other reports to form a report in accordance with the present disclosure.

A set of cross-sectional medical images associated with a particular patient may include cross-sectional images for various parts of the patient's body. For instance, the set may include scans of the user's head, neck, chest, and/or abdomen. In many instances, a physician or other reviewer of cross-sectional images for lesion analysis is only specialized, trained, and/or authorized to analyze certain types of cross-sectional images. For example, one reviewer may only specialize in reviewing head and neck cross-sectional images, whereas another reviewer may only specialize in reviewing abdominal cross-sectional images. Some reviewers may be authorized to review all cross-sectional images, regardless of the anatomical location represented in the cross-sectional images.

In instances where a reviewer will only review a subset of cross-sectional images within a set of cross-sectional images (e.g., because of the radiology subspecialty of the reviewer), presenting the entire set of cross-sectional images to the reviewer may slow the analysis speed of the reviewer and may give rise to unintentional annotations being implemented into cross-sectional images that are outside of the reviewer's expertise.

Additionally, not all radiology specialists may be simultaneously available to review a set of cross-sectional images that includes images for review by different radiology specialists. Therefore, problems may arise when a patient report is generated prematurely before all cross-sectional images within a set of cross-sectional images associated with the patient have been processed by appropriate specialists for lesion analysis. For instance, reports generated under such circumstances may omit target lesions that went unanalyzed by an absent specialist, and the omission of target lesions may skew tumor response results.

Furthermore, it is uncommon for different radiology specialists to communicate with one another when interpreting exams for the same patient. This separation of reporting often gives rise to problems when the patient has a condition that can affect different body regions, such as advanced cancer. Accordingly, the reports from different radiologic specialists may not agree, may have discrepancies, or may have conflicting information with one another when considering a patient-level review by a treating clinician. It is uncommon for radiology specialists to notice these problems when working separately from one another (e.g., when reviewing at different times and/or from different places).

Because many conditions that affect different regions are treated at the patient level, the aforementioned temporal and/or spatial separation between different radiology specialists when reviewing a patient's exams often gives rise to problem under existing techniques. For example, systemic cancer therapies are used to treat metastatic disease or lymphoma that separately involves the neck, chest, abdomen, and pelvis. In such examples, a single patient-level view of the response may be more important and/or beneficial than multiple separate reports about each separate body region (e.g., a separate neck report, chest report, abdomen, etc.). Furthermore, the reporting styles of different subspecialty radiologists could lead to additional errors. For instance, a slight increase in size in two different body regions could be interpreted differently by different reviewing physicians, with one radiologist reporting progressive disease and with another radiologist reporting stable disease. This conflicting information is difficult to resolve at the patient level and is confusing for both treatment providers and patients.

Accordingly, in some embodiments, the presently disclosed systems and methods for lesion analysis include techniques for managing access to cross-sectional images within a set of cross-sectional images and for controlling the generation of a patient report, which may comprise a composite report that includes analysis from multiple specialists. The composite report could be a patient-level report.

Radiology subspecialties may include, for example, neuroradiology or body radiology (which can include cardiothoracic, chest, and/or abdomen subspecialties) or other subspecialties as known in the art. It will be appreciated that certain radiologists may be proficient at reviewing cross-sectional images under multiple or all radiological subspecialties.

The radiology specialties associated with a particular user (e.g., a physician reviewer) may be indicated by a user profile associated with the particular user. As used herein, a "user profile" refers broadly to any computer-readable/interpretable information that indicates attributes, characteristics, settings, information, and/or the like associated with a particular user. A user profile may indicate one or more radiology specialties or subspecialties associated with a user operating a system for lesion analysis. In some instances, a user profile for a particular user may persist in computer memory outside of a particular lesion analysis session (e.g., to be used in future lesion analysis sessions for the particular user). For example, a user profile may be selectively modified (e.g. by an administrator or by the user) outside of lesion analysis sessions to enable different radiology subspecialties or combinations thereof. In some instances, a user profile for a particular user may be specific to a particular lesion analysis session (e.g., the user profile may be established based on user input provided by one or more users at the beginning of a lesion analysis session).

In accordance with the present disclosure, a system may be configured to provide subsets of cross-sectional medical images to users for analysis based on a user profile associated with the user (e.g., based on radiology subspecialties associated with the users, as indicated by the user profiles).

To facilitate such functionality, in some instances, a set of cross-sectional images (and/or one or more individual cross-sectional images thereof) may comprise or be associated with metadata, which may indicate one or more body regions or radiology specialties/subspecialties associated with one or more subsets of cross-sectional images thereof. As used herein, metadata refers broadly to any computer-readable information that provides any information about any other computer-readable information (e.g., cross-sectional images and/or sets/subsets thereof).

Various techniques may be employed for associating metadata with cross-sectional images and/or sets thereof (e.g., to indicate one or more body regions and/or radiology specialties/subspecialties associated therewith). For example, metadata may be associated with the cross-sectional images or set thereof upon image capture (e.g., by the radiologic device 104) or soon thereafter (e.g., by an entity separate from the radiologic device 104).

Figure 37:
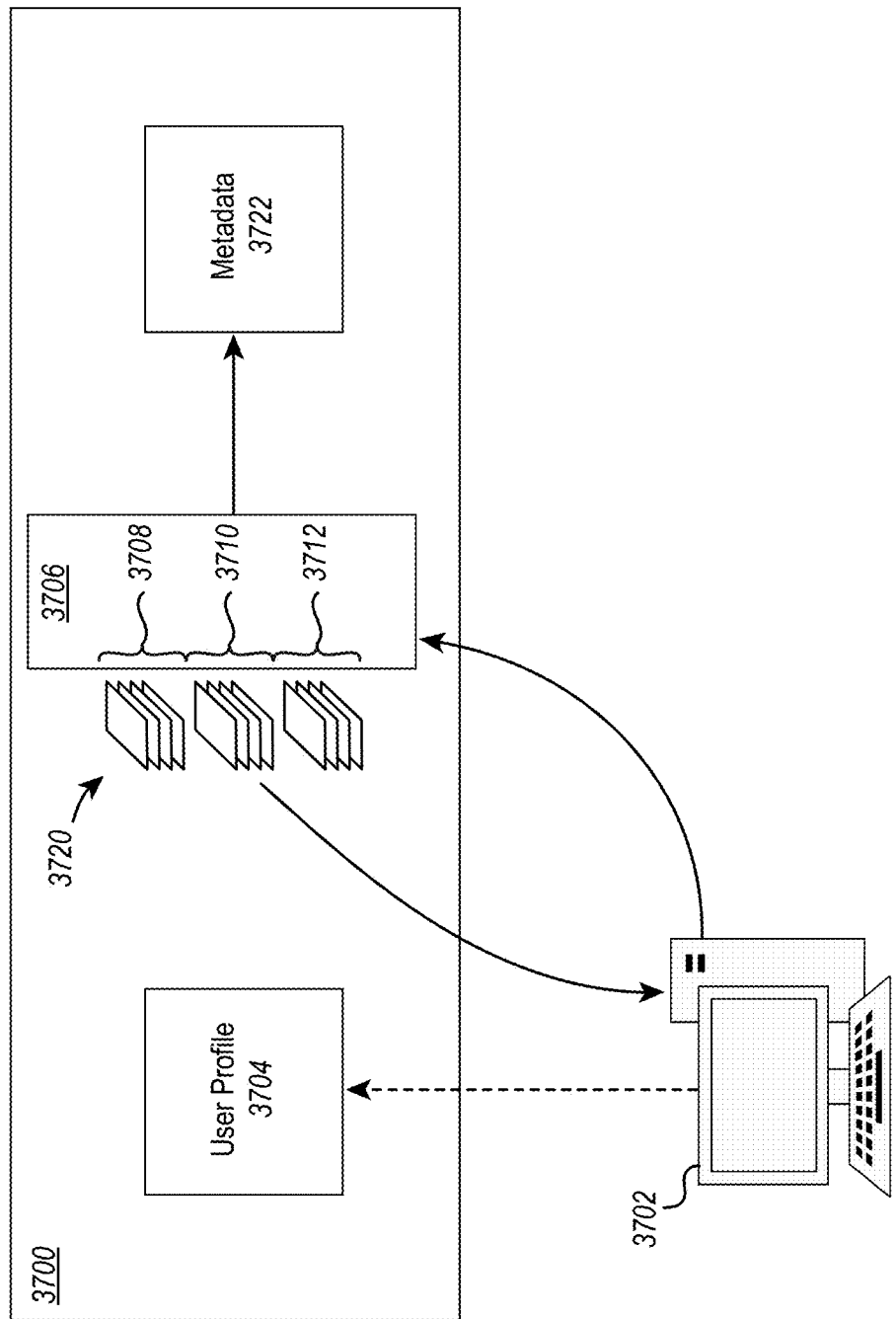
FIG. 37 illustrates a conceptual representation of prompting a user to associate cross-sectional images of a set of cross-sectional images with different specialties.

In some instances, a system prompts a user to associate cross-sectional images of a set of cross-sectional images with different body regions and/or radiology specialties/subspecialties. FIG. 37 illustrates a conceptual representation of prompting a user to associate cross-sectional images of a set of cross-sectional images with different specialties. For example, FIG. 37 illustrates a system 3700, which may at least partially correspond to a computing system 100 and/or a computing device 130*a*, 130*b*, 130*c*, or other component(s) described hereinabove with reference to FIG. 1. The system 3700 may comprise or be in communication with a user device 3702, which may at least partially correspond to a computing system 100 and/or a computing device 130*a*, 130*b*, 130*c*, described hereinabove with reference to FIG. 1. A user (e.g., a physician reviewer) may operate the user device 3702, and the user may be associated with a user profile 3704. As noted above, the user profile may indicate one or more radiology specialties and/or subspecialties associated with the user.

The system 3700 may receive a request, in association with the user profile 3704, to review a set of cross-sectional images 3720 that is accessible to the system 3700. The set of cross-sectional images 3720 may comprise different cross-sectional images capturing different portions of a patient's body and therefore being appropriate for revision by radiologists associated with different specialties/subspecialties. In some instances, the set of cross-sectional images 3720 is not already associated with metadata indicating appropriate specialties/subspecialties for the various cross-sectional images of the set. Thus, in some implementations, in response to receiving the request in association with the user profile 3704, the system provides the set of cross-sectional images 3720 to the user device 3702 and prompts a user operating the user device 3702 to identify appropriate specialties/subspecialties for the various cross-sectional images of the set of cross-sectional images 3720 (as indicated in FIG. 37 by the arrow extending from the set of cross-sectional images 3720 toward the user device 3702). In some instances, the system 3700 requires the user to complete the identification/classification of cross-sectional images prior to permitting the user to review any portion of the set of cross-sectional images 3720.

The user operating the user device 3702 may provide input 3706 in accordance with the prompt described above, which may indicate different specialties/subspecialties for different subsets of the set of cross-sectional images. By way of illustration, FIG. 37 depicts that the input 3706 indicates that a first subset 3708 of the set of cross-sectional images 3720 is associated with a head and neck body region or specialty/subspecialty, a second subset 3710 of the set of cross-sectional images 3720 is associated with a chest body region or specialty/subspecialty, and a third subset 3712 of the set of cross-sectional images 3720 is associated with an abdomen body region or specialty/subspecialty. Based on the user input, the system may associate metadata 3722 with the various subsets 3708, 3710, 3712 of cross-sectional images and/or the set of cross-sectional images 3720 indicating the appropriate body regions or specialties/subspecialties for the various subsets 3708, 3710, 3712 of cross-sectional images.

Figure 38:
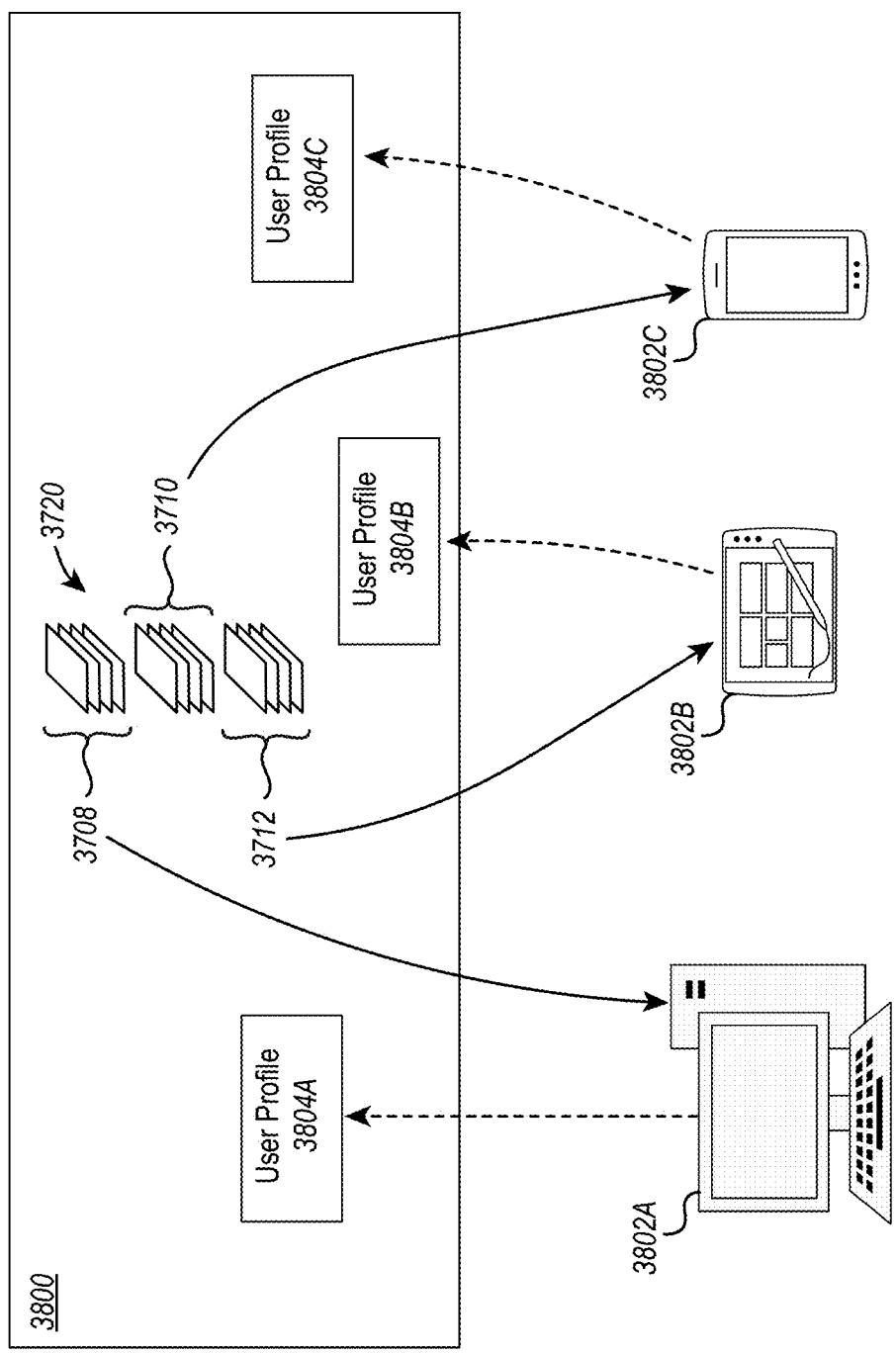
FIG. 38 illustrates a conceptual representation of identifying and providing different subsets of cross-sectional images for different users based on specialties associated with the users.

Based on the metadata (however obtained/established), a system may be prepared to provide subsets of cross-sectional images to different users for analysis based on specialties/subspecialties associated with the users. For instance, FIG. 38 illustrates a conceptual representation of identifying and providing different subsets of cross-sectional images for different users based on specialties associated with the users. In particular, FIG. 38 shows a system 3800 (which may correspond to the system 3700 described above) that receives requests to analyze at least a portion of the set of cross-sectional images 3720 in association with user profiles 3804A, 3804B, and 3804C that are associated with users operating user devices 3802A, 3802B, and 3802C. The user devices 3802A, 3802B, and 3802C may at least partially correspond to the user device 3702 described above, and it will be appreciated, in view of the present disclosure, that the user devices 3802A, 3802B, and 3802C may represent separate physical devices or may represent one or more of the same physical devices operated at different times (e.g., by different users associated with different user profiles).

As noted above, the user profiles 3804A, 3804B, and 3804C may indicate different radiology specialties/subspecialties for different users operating the different user devices 3802A, 3802B, and 3802C. For example, user profile 3804A may indicate a head and neck specialty, user profile 3804B may indicate a chest specialty, and 3804C may indicate an abdomen specialty.

In some instances, in response to the received requests, the system may identify the respective user profiles 3804A, 3804B, and 3804C and the specialties/subspecialties indicated by the user profiles 3804A, 3804B, and 3804C (e.g., head and neck, chest, and abdomen, respectively). The system may then identify, based on the user profiles 3804A, 3804C, and 3804B, appropriate respective subsets of cross-sectional images from the set of cross-sectional images 3720 to provide to the various user devices 3802A, 3802B, and 3802C. For example, the system may provide the first subset 3708 comprising head and neck cross-sectional images to user device 3802A based on user profile 3804A, the system may provide the second subset 3710 comprising chest cross-sectional images to user device 3802B based on user profile 3804B, and the system may provide the third subset 3712 comprising abdomen cross-sectional images to user device 3802C based on user profile 3804C (indicated in FIG. 38 by the arrows extending from the various subsets toward the various user devices). For a particular user device/user profile, the system 3800 may refrain from providing subsets of cross-sectional images that are not related to the same specialty/subspecialty indicated by the user profile, which may advantageously allow the user to focus on the cross-sectional images within their radiological specialty/subspecialty.

Upon receiving an applicable subset of cross-sectional images 3708, 3710, and/or 3712, users operating the various user devices 3802A, 3802B, and 3802C may carry out lesion analysis according to the principles and/or techniques described herein (which may be at least partially synchronous or asynchronous in time, depending on the availability of the various users). For example, the user devices 3802A, 3802B, and 3802C may receive user input that marks, segments, and/or labels one or more lesions represented within the corresponding subset 3708, 3710, or 3712 of cross-sectional images. In some instances, the user devices 3802A, 3802B, and 3802C may operate to provide guided presentations of respective selections of the respective subsets of cross-sectional images that include analyzed lesions (e.g., a lesion that was previously marked and/or segmented, see FIGS. 23-26 and attendant description). In some instances, the user devices 3802A, 3802B, and 3802C may operate to facilitate longitudinal analysis of lesions (e.g., see FIGS. 28-33 and attendant description)

Figure 39:
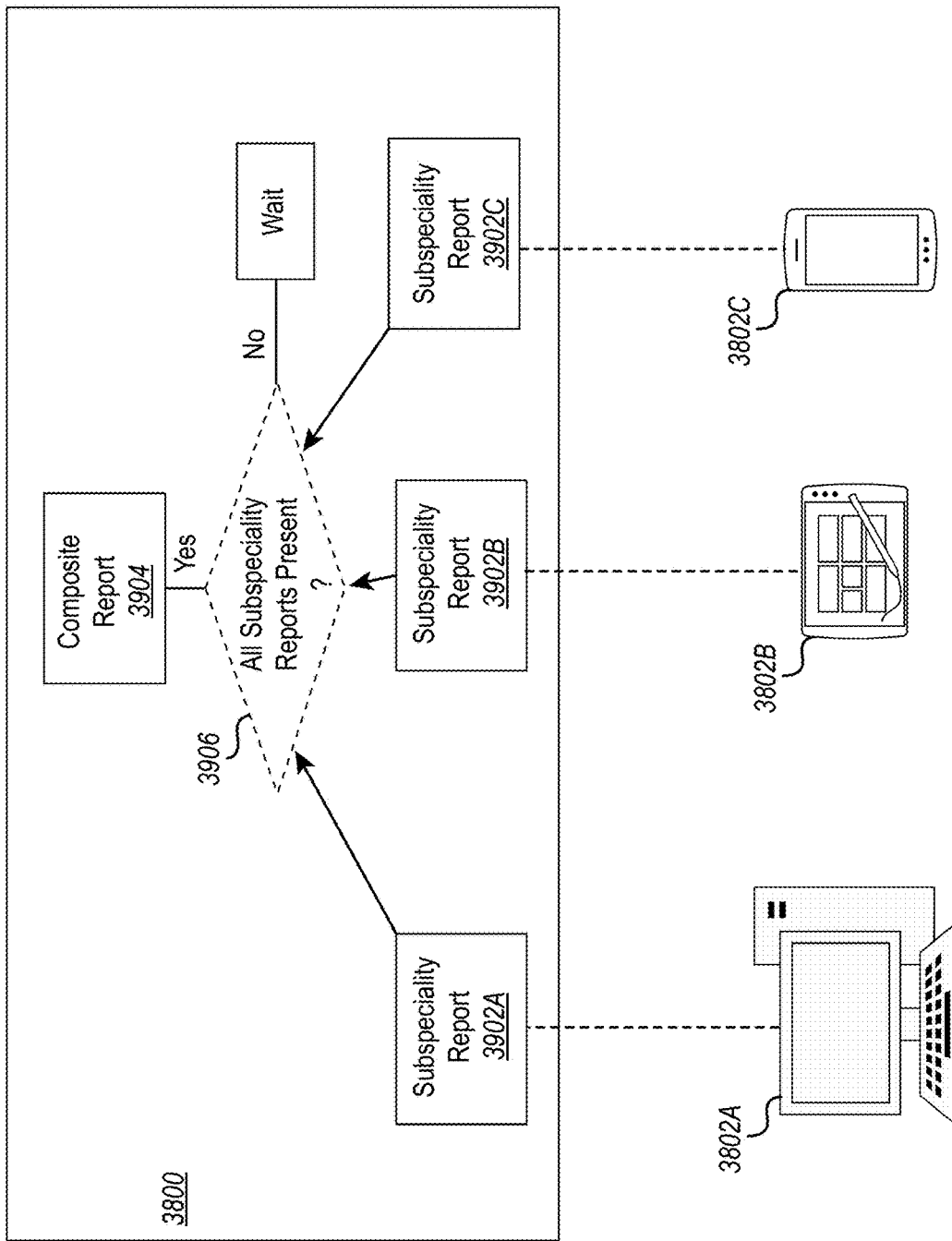
FIG. 39 illustrates a conceptual representation of generating or updating a composite report based on marking, segmentation, or labeling performed by different users for lesions represented in the different subsets of cross-sectional images.

Lesion information (e.g., based at least in part on user input at the various user devices 3802A, 3802B, and 3802C) associated with various lesions represented in the various subsets 3708, 3710, and 3712 may become organized into a subspecialty report. For example, FIG. 39 shows subspecialty reports 3902A, 3902B, and 3902C based on user input provided at the various respective user devices 3802A, 3802B, and 3802C. The subspecialty report 3902A may include lesion information for lesions represented within the first subset 3708 of cross-sectional images and analyzed using user device 3802A. Similarly, subspecialty report 3902B may include lesion information for lesions represented within the second subset 3710 of cross-sectional images and analyzed using user device 3802B, and subspecialty report 3902C may include lesion information for lesions represented within the third subset 3712 of cross-sectional images and analyzed using user device 3802C.

As used herein, a "subspecialty report" may refer to an at least partially formalized or organized report similar to one or more of those described herein with reference to FIGS. 27 and 34-36, or may refer more generally to any lesion information stored based at least in part on user input (e.g., from a radiologist reviewing cross-sectional images) provided at a user device (e.g., one of the various user devices 3802A, 3802B, and 3802C).

As depicted in FIG. 39, a system 3900 may receive the various subspecialty reports 3902A, 3902B, and 3902C. The system 3900 may at least partially correspond to the system 3800 described above. The system 3900 may be configured/configurable to generate a composite report 3904 based on the various subspecialty reports 3902A, 3902B, and 3902C received. However, FIG. 39 shows that, in some instances, the system 3900 is configured to refrain from generating or finalizing a composite report 3904 (e.g., for sending to an oncologist, patient, or other end user of the report) until the system 3900 verifies that all appropriate subspecialty reports 3902A, 3902B, and 3902C have been received.

For example, FIG. 39 illustrates a decision block 3906 associated with the system, whereby the system may determine whether all expected subspecialty reports are present. For instance, continuing with the above example where the set of cross-sectional images 3720 is associated with three separate subsets 3708, 3710, and 3712 of cross-sectional images corresponding to different specialties/subspecialties, the system 3900 may be configured to refrain from generating or finalizing a composite report 3904 until a subspecialty report (comprising lesion information obtained from lesion analysis performed) has been received in association with each of the different subsets 3708, 3710, and 3712 of the set of cross-sectional images 3720. For example, as discussed hereinabove, different radiology specialists may perform lesion analysis at different times, even when analyzing different subsets of cross-sectional images for a single patient (e.g., with one specialist analyzing abdomen images, with another specialist analyzing chest images, etc.). Thus, different subspecialty reports may be created or available at different times.

When the system 3900 determines that all applicable subspecialty reports have been received, the system 3900 may proceed to generate, finalize, update, or send a composite report 3904 for use by an end user (e.g., an oncologist or patient). For example, a system 3900 may be configured to create or update the composite report 3904 in response to determining that a final reader has completed their evaluation of a patient, or in response to determining that each subset of images that is queued or intended for analysis for a particular patient has been analyzed by one or more radiologists. Such functionality may advantageously prevent patient or oncological reports from being prematurely generated based on incomplete information (e.g., in situations where not all specialists are available to perform lesion analysis within the same time period), thereby improving patient care.

It should be appreciated that the composite report can be generated from a subset of subspecialty reports, and the inclusion of any number or type of subspecialty reports within a composite report can be selected by the physician or other healthcare provider. For example, a subspecialty radiologist can perform their respective analysis of the cross-sectional images and generate a report that includes only those findings related to their analysis and/or subspecialty. Such reports can be formatted as a patient-level report having, for example, a graph, table, key images, and/or structured text representing information from the given subspecialty radiologist.

In addition to indicating a radiology subspecialty for which the user is enabled to perform lesion analysis on cross-sectional images, user profiles may allow for a personalized experience for users when performing lesion analysis on cross-sectional images. Providing a personalized experience may improve user attentiveness and/or accuracy when performing lesion analysis as described herein.

In this regard, a user profile may indicate one or more system interaction preferences for the user. The interaction preferences may include one or more interaction presentations, such as sounds, images, animations, and/or combinations thereof.

As described hereinabove, the system may provide various control mechanisms (e.g., via I/O device interface(s) 106) to allow a user to control certain aspects of lesion analysis. These controls may include, for example, selecting a position within a pixel region corresponding to a lesion represented in a cross-sectional medical image, tracing/segmenting a pixel region associated with a lesion, selecting location information for a lesion, navigating through a guided presentation of a subset of cross-sectional medical images that include one or more marked lesions, selecting a representation of a list entry associated with a cross-sectional medical image that includes one or more marked lesions, accepting a predicted lesion shape or lesion location information generated by a machine learning module, rejecting a predicted lesion shape or lesion location information generated by a machine learning module, triggering display of a report comprising information associated with one or more marked lesions present within the plurality of cross-sectional medical images, navigating through a set of cross-sectional images, and zooming a display of a cross-sectional image.

Accordingly, the system may identify a user profile of the user accessing the system and associate one or more controls provided by the system with one or more interaction preferences/presentations specified within the user profile. In some implementations, the interaction preferences include a different interaction presentation for each of the controls provided by the system. Subsequently, in response to detecting user input operating one of the associated controls, the system presents the applicable interaction presentation.

By way of non-limiting example, a user's profile may indicate an interaction preference that includes presenting an image of a calligraphy pen as a mouse cursor instead of a traditional cursor. The system may associate the interaction presentation of presenting the calligraphy pen with the control of tracing a pixel region associated with a lesion. Thereafter, when the user's profile is activated and in response to detecting user input for tracing a pixel region associated with a lesion, the system replaces the mouse cursor with the image of the calligraphy pen, and the image persists while the user traces the pixel region.

In some embodiments, the user profile may be associated with user-selected sound and/or visual effects profiles for pre-selected actions. For example, selecting target lesions or non-target lesions may be associated with a first sound while segmenting or correcting auto-segmentation results can be associated with a different sound, such as a swooshing sound of a katana or humming of a saber as portions of the segmented lesion are lopped off by the re-segmentation action. The sounds may be preset or configurable by the user. Additionally, or alternatively, the sounds may be thematic in accordance with a genre (e.g., Western, Science Fiction, Steam Punk, Medieval, etc.) or specific to a movie, video game, song, and/or other popular culture creation (e.g., television show, play, cartoon, etc.). A visual effect could mimic lights, colors and/or other aspects of the same sound effects theme and could mimic visual effects from a specific movie, video game, song or other popular culture creation. The sounds and visual effects could be mapped to specific keys or actions in the user interface. The sound and visual effects could be used to improve user attention, enjoyment, engagement, and/or efficiency and could be used in product demonstrations, product trial versions, product challenges, and final production versions of the user interface. The sound and visual effects could be selectively turned off by the user, and the sound effects could include background music. Background music could follow the same theme as the sound and visual effects or could diverge from these at the preference of the user.

In addition to defining interaction presentations that may be associated with system controls, a user profile may also include a user interface theme that alters a rendering of at least some of the controls or the user interface for lesion analysis as described and shown herein.

In some embodiments, the user interface and associated system track the time and/or number of errors made by a user and ranks the user's performance. Points can be attributed to various actions and gained or lost in accordance with the user's performance. In some embodiments, the user interface displays the gain or loss of points in real time and/or after a task or session is completed. For example, the user interface may display a target lesion selected by the user concomitantly with a point value in accordance with the selection's adherence to one or more rules associated with the tumor response criterion/criteria followed during the reading and/or in accordance with a proper identification. In this way, different user metrics can be tracked over time and compared to other users to identify weaknesses and/or strengths of various users. In some instances, an attending radiologist can utilize such a system to score various residents who may have initially read the images. In some embodiments, such a review can be undertaken using the guided presentation functionality discussed above with respect to FIGS. 23-26 and/or the longitudinal analysis functionality discussed above with respect to FIGS. 28-33.

Example Methods Associated with Lesion Analysis

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

FIGS. 40, 41, 42 and 43 illustrate example flow diagrams 4000, 4100, 4200 and 4300, respectively, which depict acts associated with analyzing lesions in cross-sectional medical images. The discussion of the various acts represented in the flow diagrams may include references to various hardware components described in more detail with reference to FIGS. 1, 17, 38, and/or 39. One will appreciate, in view of the present disclosure, that various embodiments may omit one or more of the acts described hereinbelow.

Figure 40:
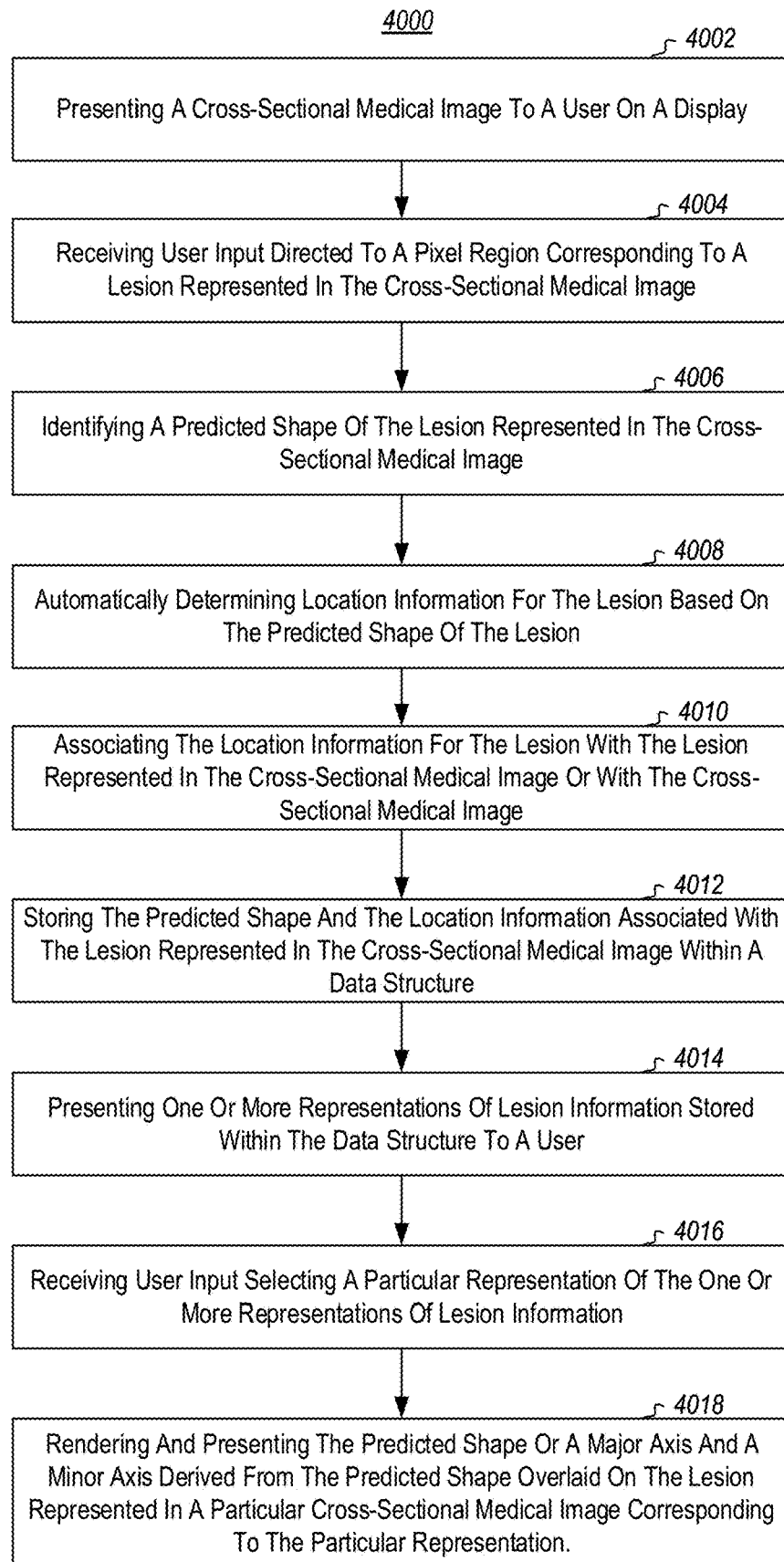
FIGS. 40-43 illustrate example flow diagrams depicting acts associated with facilitating lesion analysis.

Act 4002 of flow diagram 4000 of FIG. 40 includes presenting a cross-sectional medical image to a user on a display. Act 4002 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. The cross-sectional medical image may comprise one or more of CT images, CTP images, PET images, SPECT images, MRI images, or ultrasound images, and/or others. Such images may be obtained by a radiologic device 104.

Act 4004 of flow diagram 4000 includes receiving user input directed to a pixel region corresponding to a lesion represented in the cross-sectional medical image. Act 4004 may be carried out using one or more components (e.g., I/O device interface(s) 106, hardware processor(s) 108, hardware storage device(s) 112, and/or others) of a computing system 100 or similar device. In some implementations, the user input may comprise user input provided by a mouse cursor navigated over the lesion represented in the cross-sectional medical image, or a similar type of user input (e.g., provided via a touch screen).

In some instances, the presentation of the cross-sectional medical image may be zoomed toward the lesion represented in the cross-sectional medical image in response to the user input directed at the pixel region corresponding to the lesion.

Act 4006 of flow diagram 4000 includes identifying a predicted shape of the lesion represented in the cross-sectional medical image. Act 4006 may be carried out using one or more components (e.g., hardware processor(s) 108, image processing module(s) 110, hardware storage device(s) 112, data processing module(s) 114, primary database 116, machine learning module(s) 120, and/or others) of a computing system 100 or similar device. In some instances, the predicted shape is identified based on contrast between the pixel region corresponding to the lesion and a surrounding pixel region.

Furthermore, in some implementations, identifying the predicted shape is further based on differences in contrast between one or more separate pixel regions in one or more neighboring cross-sectional medical images (e.g., image slices ordinally adjacent to the cross-sectional medical image within which the pixel region was selected) that correspond to the pixel region to which the user input was directed and one or more separate surrounding pixel regions that surround the separate pixel regions in the one or more neighboring cross-sectional medical images.

In some implementations, after identifying the predicted shape, act 4006 may further include presenting a rendering of the predicted shape of the lesion overlaid on the lesion represented in the cross-sectional image to the user. In some instances, in addition to the predicted shape, a predicted major axis and a predicted minor axis of the lesion may also be presented, and the predicted major axis and the predicted minor axis of the lesion may be determined based at least in part on the predicted shape.

Act 4006 may further include prompting the user to accept or reject the predicted shape as displayed to the user. User input may be received that rejects the predicted shape of the lesion. User input (the same or separate user input) may be received that modifies the predicted shape of the lesion. For instance, a user-directed trace tool may be utilized to modify the predicted shape of the lesion.

Act 4008 of flow diagram 4000 includes automatically determining location information for the lesion based on the predicted shape of the lesion. Act 4008 may be carried out using one or more components (e.g., hardware processor(s) 108, image processing module(s) 110, hardware storage device(s) 112, data processing module(s) 114, primary database 116, machine learning module(s) 120, and/or others) of a computing system 100 or similar device. The location information may comprise indication of an anatomical location of the lesion which may include, for example, an indication of whether the lesion is a mass or a lymph node and/or an indication that the lesion is located in one of: a neck, a chest, an abdomen, a pelvis, an arm, or a leg.

In some instances, the location information for the lesion is determined at least in part by providing the predicted shape of the lesion as an input to a machine learning module 120 trained to identify lesion location information based on input shape. In some instances, the predicted shape as modified by the user input that modifies the predicted shape may be used as an input to the machine learning module 120 to determine the location information for the lesion. The machine learning module 120 may identify the location information for the lesion based on the predicted shape.

The machine learning module 120 may utilize one or more additional or alternative inputs for determining the location information for the lesion, such as: metadata associated with the cross-sectional medical image indicating an anatomical location of the lesion, other structures represented in the cross-sectional medical image, a pixel coordinate of the user input directed to the pixel region, and/or others.

In some instances, Act 4008 includes presenting a rendering of the location information to the user, which may, in some implementations, be presented contemporaneously with a presentation of a rendering of the lesion represented in the cross-sectional medical image. Act 4008 may also include prompting the user to either accept the location information or modify the location information. In some instances, user input modifying the location information may be received. Such user input may modify the location information selected/identified via the machine learning module 120 and/or may add additional location information to the location information selected/identified via the machine learning module 120. For instance, such user input may include a user indication of whether the lesion is a mass or a lymph node.

In some instances, in response to receiving user input modifying the location information selected/identified via the machine learning module 120, the machine learning module 120 automatically redetermines the location information by providing the predicted shape and at least a portion of the location information as modified by the user as input to the machine learning module 120. The machine learning module may then reidentify the location information for the lesion.

Act 4010 of flow diagram 4000 includes associating the location information for the lesion with the lesion represented in the cross-sectional medical image or with the cross-sectional medical image. Act 4010 may be carried out using one or more components (e.g., I/O device interface(s) 106, hardware processor(s) 108, hardware storage device(s) 112, data processing module(s) 114, primary database 116, machine learning module(s) 120, and/or others) of a computing system 100 or similar device.

Act 4012 of flow diagram 4000 includes storing the predicted shape and the location information associated with the lesion represented in the cross-sectional medical image within a data structure. Act 4012 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. In some instances, additional or alternative information associated with the lesion may be stored. For instance, a major axis and a minor axis of the lesion (e.g., determined based on the predicted shape) may be stored in the data structure in association with the lesion and in accordance with act 4012. In some instances, the location information as modified by a user according to act 4008 becomes stored within the data structure in association with the lesion.

Flow diagram 4000 may comprise acts that are performed using lesion information stored within the data structure, such as facilitating a guided presentation or review of the lesion(s) for which associated information is stored within the data structure in accordance with act 4012.

For example, act 4014 of flow diagram 4000 includes presenting one or more representations of lesion information (e.g., predicted shapes, location information, major/minor axes, and/or other lesion metrics/information) stored within the data structure to a user. Act 4016 of flow diagram 4000 includes receiving user input selecting a particular representation of the one or more representations of lesion information. Act 4018 of flow diagram 4000 includes rendering and presenting the predicted shape or a major axis or a minor axis derived from the predicted shape overlaid on the lesion represented in a particular cross-sectional medical image corresponding to the particular representation. Acts 4014, 4016, and/or 4018 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device.

Figure 41:
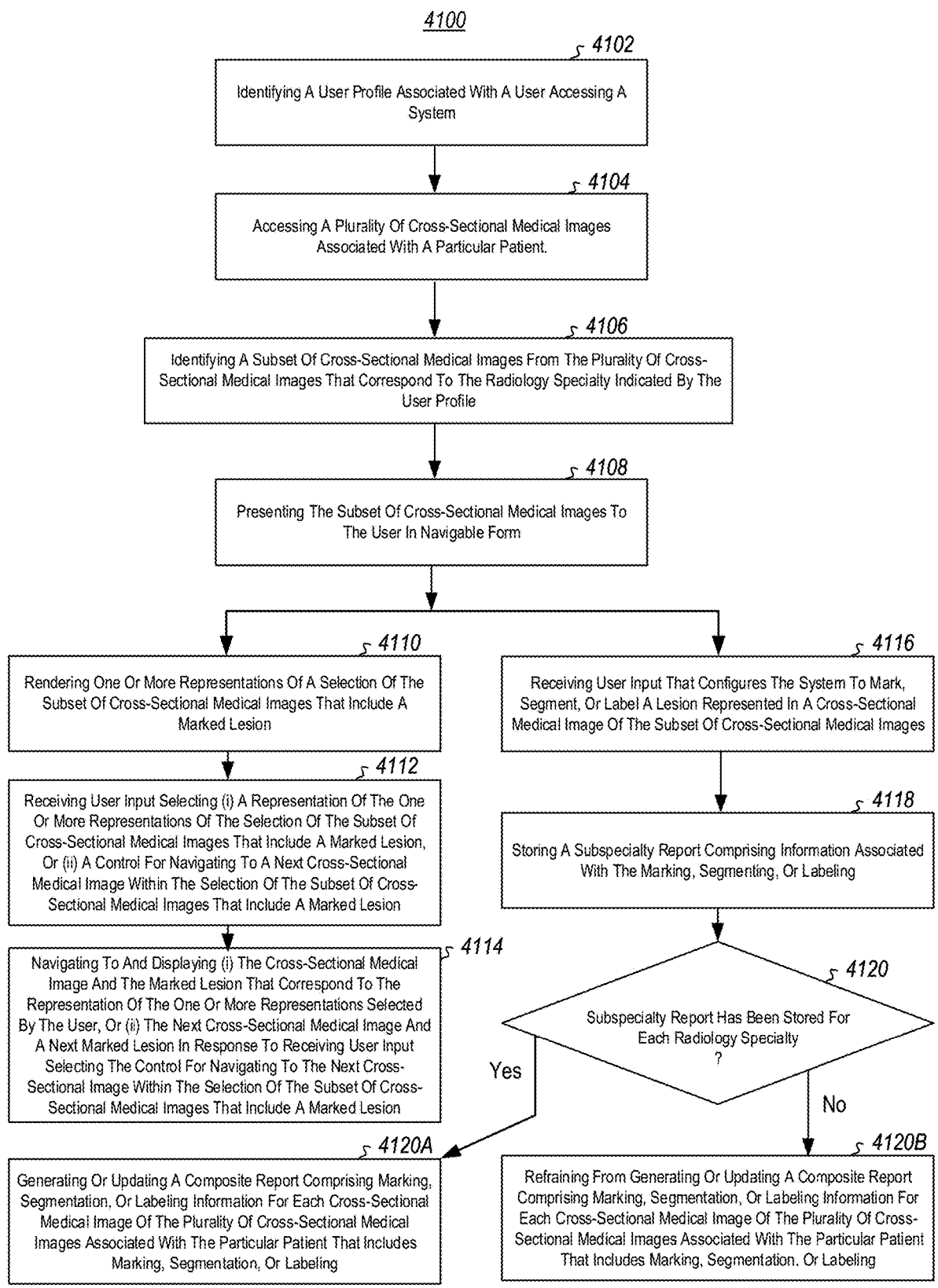

Act 4102 of flow diagram 4100 of FIG. 41 includes identifying a user profile associated with a user accessing a system. Act 4102 may be carried out using one or more components (e.g., I/O device interface(s) 106, hardware processor(s) 108, hardware storage device(s) 112, data processing module(s) 114, primary database 116, machine learning module(s) 120, and/or others) of a computing system 100 or similar device. The user profile may indicate a radiology specialty associated with the user. The radiology specialty may comprise, for example, a radiology subspecialty, such as neuroradiology or thoracic radiology (e.g., including subspecialties of chest and/or abdomen).

Act 4104 of flow diagram 4100 includes accessing a plurality of cross-sectional medical images associated with a particular patient. Act 4104 may be carried out using one or more components (e.g., I/O device interface(s) 106, hardware processor(s) 108, image processing module(s) 110, hardware storage device(s) 112, primary database 116, machine learning module(s) 120, and/or others) of a computing system 100 or similar device. In some instances, one or more of the plurality of cross-sectional medical images may comprise or be associated with metadata indicating different radiology specialties that correspond to different subsets of the plurality of cross-sectional medical images.

In some instances, no (or incomplete) metadata is initially associated with the plurality of cross-sectional medical images. Thus, in some implementations, Act 4104 may include prompting, at a user device, the user to provide user input to associate one or more cross-sectional medical images within the plurality of cross-sectional medical images with one or more radiology specialties. Based on user input, metadata may be stored for each of the one or more cross-sectional medical images, and the metadata may indicate the corresponding radiology specialty.

Act 4106 of flow diagram 4100 includes identifying a subset of cross-sectional medical images from the plurality of cross-sectional medical images that correspond to the radiology specialty indicated by the user profile. Act 4106 may be carried out using one or more components (e.g., I/O device interface(s) 106, hardware processor(s) 108, hardware storage device(s) 112, data processing module(s) 114, primary database 116, machine learning module(s) 120, and/or others) of a computing system 100 or similar device. In some instances, identifying the subset of cross-sectional medical images that are associated with the radiology specialty indicated by the user profile is based on metadata associated with one or more of the cross-sectional medical images of the plurality of cross-sectional medical images (whether established in accordance with act 4104 or otherwise).

Act 4108 of flow diagram 4100 includes presenting the subset of cross-sectional medical images to the user in navigable form. Act 4108 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device.

Flow diagram 4100 may include acts associated with lesion analysis performed using the subset of cross-sectional medical images of act 4108.

For example, act 4110 of flow diagram 4100 includes rendering one or more representations of a selection of the subset of cross-sectional medical images that include a marked lesion. Act 4110 may be carried out using one or more components (e.g., I/O device interface(s) 106, hardware processor(s) 108, hardware storage device(s) 112, primary database 116, and/or others) of a computing system 100 or similar device. The one or more representations of the selection of the subset of cross-sectional medical images that include a marked lesion may be depicted, in some implementations, as elements of a list displayed to a user.

Act 4112 of flow diagram 4100 includes receiving user input selecting (i) a representation of the one or more representations of the selection of the subset of cross-sectional medical images that include a marked lesion, or (ii)

a control for navigating to a next cross-sectional medical image within the selection of the subset of cross-sectional medical images that include a marked lesion. Act 4112 may be carried out using one or more components (e.g., I/O device interface(s) 106, hardware processor(s) 108, hardware storage device(s) 112, primary database 116, and/or others) of a computing system 100 or similar device. For example, where the one or more representations of the selection of the subset of cross-sectional medical images that include a marked lesion are depicted as elements of a list displayed to a user, a user may select one or more of the list elements. Similarly, a user may direct user input toward a selectable button configured to navigate to the cross-sectional image associated with a next or subsequent list element.

Act 4114 of flow diagram 4100 includes navigating to and displaying (i) the cross-sectional medical image and the marked lesion that correspond to the representation of the one or more representations selected by the user, or (ii) the next cross-sectional medical image and a next marked lesion in response to receiving user input selecting the control for navigating to the next cross-sectional image within the selection of the subset of cross-sectional medical images that include a marked lesion. Act 4114 may be carried out using one or more components (e.g., I/O device interface(s) 106, hardware processor(s) 108, hardware storage device(s) 112, primary database 116, and/or others) of a computing system 100 or similar device. In some instances, acts 4110, 4112, and 4114 may facilitate guided presentations of lesions represented cross-sectional medical images to allow users to quickly review and/or assess analyzed lesions (e.g., as described with reference to FIGS. 23-26).

In addition, or alternative, to acts 4110, 4112, and/or 4114 of flow diagram 4100, acts 4116, 4118, 4120A, and/or 4120B of flow diagram 4100 may be performed, which may facilitate lesion analysis (e.g., as described with reference to FIGS. 2-22).

Act 4116 of flow diagram 4100 includes receiving user input that configures the system to mark, segment, or label a lesion represented in a cross-sectional medical image of the subset of cross-sectional medical images. Act 4116 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. In some implementations, the marking or segmentation of the lesion includes determining a predicted shape for the lesion (e.g., via the machine learning module 120), and the labeling of the lesion includes providing the predicted shape and/or other inputs to a machine learning module 120 as inputs to determine anatomical location information for the lesion.

Act 4118 of flow diagram 4100 includes storing a subspecialty report comprising information associated with the marking, segmenting, or labeling. Act 4102 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. A subspecialty report may comprise any information associated with an analyzed lesion, such as shape, major/minor axis, anatomical location, or even image data associated with the lesion. A subspecialty report may take the form of a formalized report ready for end use (e.g., by a patient or an oncologist), or may simply comprise data stored in a computer-readable manner.

Flow diagram 4100 includes a decision block 4120, which includes determining whether a subspecialty report has been stored for each radiology specialty (in particular, a subspecialty report for each radiology specialty that corresponds to a subset of cross-sectional medical images from the plurality of cross-sectional medical images associated with the particular patient). In this regard, decision block 4120 may comprise determining determine that marking, segmentation, or labeling has been performed for each radiology specialty that corresponds to a subset of cross-sectional medical images from the plurality of cross-sectional medical images associated with the particular patient.

Flow diagram 4100 illustrates that, in response to determining that a subspecialty report has been stored for each radiology specialty according to decision block 4120, act 4120A may be performed. Act 4120A includes generating or updating a composite report comprising marking, segmentation, or labeling information for each cross-sectional medical image of the plurality of cross-sectional medical images associated with the particular patient that includes marking, segmentation, or labeling (e.g., comprising lesion information from each subspecialty report). Act 4120A may be carried out using one or more components (e.g., I/O device interface(s) 106, hardware processor(s) 108, hardware storage device(s) 112, data processing module(s) 114, primary database 116, and/or others) of a computing system 100 or similar device.

Flow diagram 4100 also illustrates that, in response to determining that a subspecialty report has not been stored for each radiology specialty according to decision block 4120, act 4120B may be performed. Act 4120B includes refraining from generating or updating a composite report comprising marking, segmentation, or labeling information for each cross-sectional medical image of the plurality of cross-sectional medical images associated with the particular patient that includes marking, segmentation, or labeling.

Figure 42:
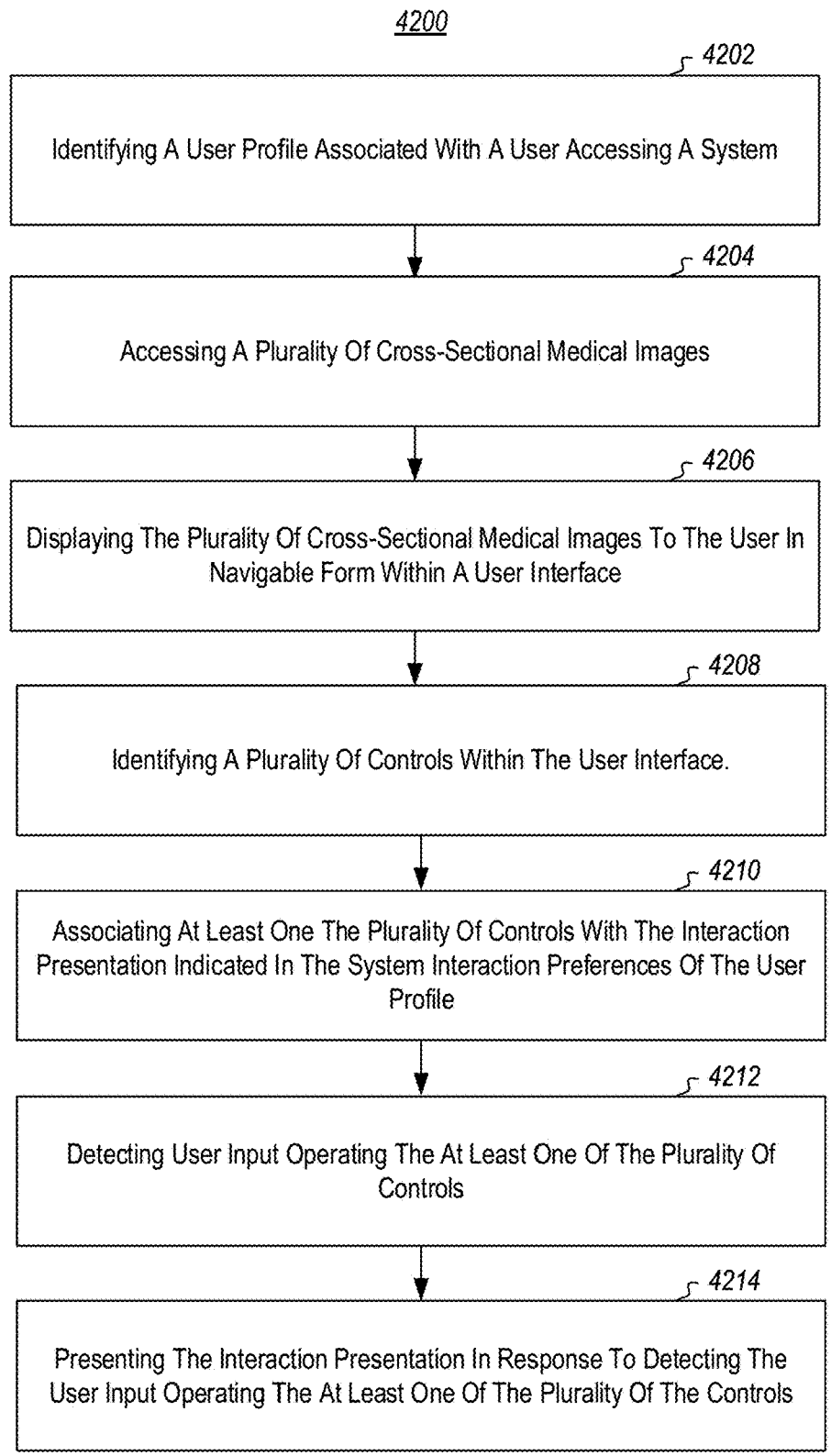

Act 4202 of flow diagram 4200 of FIG. 42 includes identifying a user profile associated with a user accessing a system. Act 4202 may be carried out using one or more components (e.g., I/O device interface(s) 106, hardware processor(s) 108, hardware storage device(s) 112, data processing module(s) 114, primary database 116, and/or others) of a computing system 100 or similar device. In some instances, the user profile indicates system interaction preferences for the user, and the system interaction preferences for the user may include an interaction presentation.

The system interaction preferences include a different interaction presentation for each of the plurality of controls. For example, the interaction presentation may include a sound, an image, and/or animation. The system interaction preferences may further include a user interface theme that alters a rendering of at least some of the plurality of controls within the user interface (see act 4208).

Act 4204 of flow diagram 4200 includes accessing a plurality of cross-sectional medical images. Act 4204 may be carried out using one or more components (e.g., I/O device interface(s) 106, hardware processor(s) 108, hardware storage device(s) 112, data processing module(s) 114, primary database 116, and/or others) of a computing system 100 or similar device. The plurality of cross-sectional medical images may comprise one or more of CT images, CTP images, PET images, SPECT images, MRI images, or ultrasound images, and/or others. Such images may be obtained by a radiologic device 104.

Act 4206 of flow diagram 4200 includes displaying the plurality of cross-sectional medical images to the user in navigable form within a user interface. Act 4206 may be carried out using one or more components (e.g., I/O device interface(s) 106, hardware processor(s) 108, image processing module(s) 110, hardware storage device(s) 112, data processing module(s) 114, primary database 116, and/or others) of a computing system 100 or similar device. The user interface may be operated by a physician reviewer that is able to perform lesion analysis on lesions represented in the plurality of cross-sectional medical images.

Act 4208 of flow diagram 4200 includes identifying a plurality of controls within the user interface. Act 4208 may be carried out using one or more components (e.g., I/O device interface(s) 106, hardware processor(s) 108, hardware storage device(s) 112, primary database 116, and/or others) of a computing system 100 or similar device.

The plurality of controls may include, by way of non-limiting example, controls for: (i) selecting a position within a pixel region corresponding to a lesion represented in the cross-sectional medical images (e.g., the lesion may comprise a target lesion, non-target lesion, or lesion that is neither a target nor a non-target lesion), (ii) tracing the pixel region associated with the lesion represented in the cross-sectional medical images, (iii) selecting location information for the lesion, (iv) navigating through a guided presentation of a subset of cross-sectional medical images of the plurality of cross-sectional medical images that include one or more marked lesions, (v) selecting a representation of a list entry associated with a cross-sectional medical image of the plurality of cross-sectional medical image that includes one or more marked lesions, (vi) accepting a predicted lesion shape or lesion location information generated by a machine learning module 120, (vii) rejecting a predicted lesion shape or lesion location information generated by a machine learning module, and/or (viii) triggering display of a report comprising information associated with one or more marked lesions present within the plurality of cross-sectional medical images.

Act 4210 of flow diagram 4200 includes associating at least one the plurality of controls with the interaction presentation indicated in the system interaction preferences of the user profile. Act 4210 may be carried out using one or more components (e.g., I/O device interface(s) 106, hardware processor(s) 108, hardware storage device(s) 112, data processing module(s) 114, primary database 116, and/or others) of a computing system 100 or similar device. Multiple controls may be associated with the same or different interaction preferences.

Act 4212 of flow diagram 4200 includes detecting user input operating the at least one of the plurality of controls. Act 4212 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. Such user input may be provided by a physician reviewer performing lesion analysis using the plurality of cross-sectional medical images.

Act 4214 of flow diagram 4200 includes presenting the interaction presentation in response to detecting the user input operating the at least one of the plurality of the controls. Act 4214 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. In some instances, presenting interaction presentations responsive to user input operating controls for lesion analysis may at least partially ameliorate the mundanity associated with performing lesion analysis, and such functionality may thereby improve the alertness and engagement of physician reviewers, thereby increasing accuracy and/or efficiency. In some implementations, when the at least one of the plurality of controls is tracing the pixel region associated with the lesion, the interaction animation may persist while the user traces the pixel region associated with the lesion.

Figure 43:
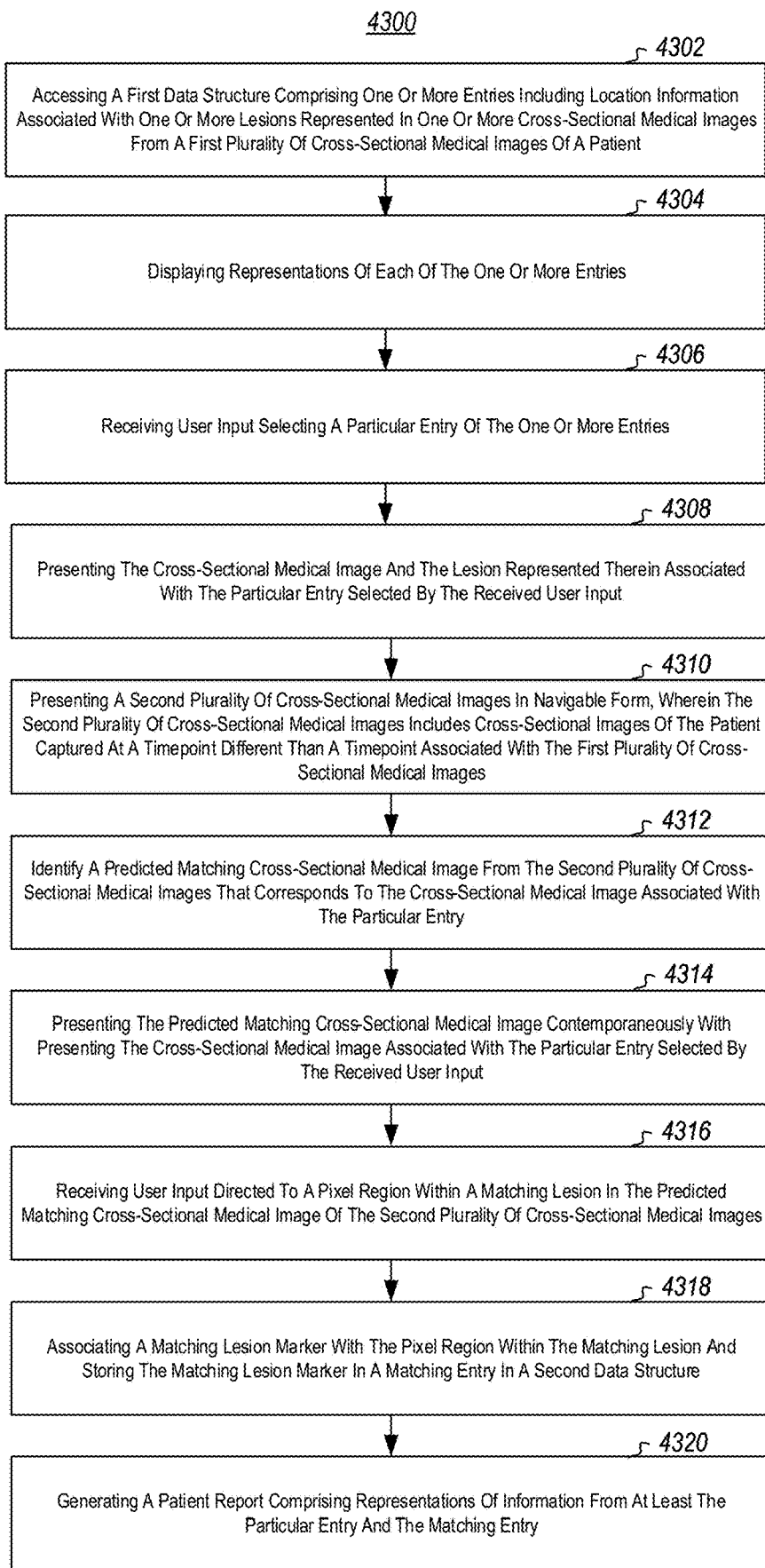

Act 4302 of flow diagram 4300 of FIG. 43 includes accessing a first data structure comprising one or more entries including location information associated with one or more lesions represented in one or more cross-sectional medical images from a first plurality of cross-sectional medical images of a patient. Act 4302 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. The one or more entries may comprise, for example, a shape associated with the one or more lesions and/or a major axis and/or a minor axis associated with the one or more lesions.

Act 4304 of flow diagram 4300 includes displaying representations of each of the one or more entries. Act 4304 may be carried out using one or more components (e.g., I/O device interface(s) 106, hardware processor(s) 108, hardware storage device(s) 112, data processing module(s) 114, primary database 116, and/or others) of a computing system 100 or similar device. In some implementations, the representations of each of the one or more entries may be displayed or presented as elements of a list (e.g., as shown in FIGS. 28-32).

Act 4306 of flow diagram 4300 includes receiving user input selecting a particular entry of the one or more entries. Act 4306 may be carried out using one or more components (e.g., I/O device interface(s) 106, hardware processor(s) 108, hardware storage device(s) 112, and/or others) of a computing system 100 or similar device. In some instances, the particular entry is selected via a user selection of a representation of the particular entry (e.g., selecting a list element corresponding to the particular entry). In some instances, the particular entry is selected via a control for navigating to a next entry, where the particular entry is the next entry.

Act 4308 of flow diagram 4300 includes presenting the cross-sectional medical image and the lesion represented therein associated with the particular entry selected by the received user input. Act 4308 may be carried out using one or more components (e.g., I/O device interface(s) 106, hardware processor(s) 108, hardware storage device(s) 112, primary database 116, and/or others) of a computing system 100 or similar device. In some instances, a lesion marker associated with the particular entry is overlaid on the lesion represented in the cross-sectional medical image corresponding to the particular entry. In some instances, a lesion marker may comprise an "X" mark, or major and/or minor axes associated with the lesion represented in the cross-sectional medical image corresponding to the particular entry.

Act 4310 of flow diagram 4300 includes presenting a second plurality of cross-sectional medical images in navigable form, wherein the second plurality of cross-sectional medical images includes cross-sectional images of the patient captured at a timepoint different than a timepoint associated with the first plurality of cross-sectional medical images.

Act 4312 of flow diagram 4300 includes identify a predicted matching cross-sectional medical image from the second plurality of cross-sectional medical images that corresponds to the cross-sectional medical image associated with the particular entry (e.g., the particular entry of acts 4306 and 4308). Act 4312 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. In some instances, act 4312 is performed in response to detecting the user input selecting the particular entry according to act 4306.

The predicted matching cross-sectional medical image may be identified using various techniques and/or factors/inputs. For example, the predicted matching cross-sectional medical image may be identified based on a slice number associated with the particular entry. In some instances, the predicted matching cross-sectional image may be identified via image co-registration between the cross-sectional medical image associated with the particular entry and at least some of the second plurality of cross-sectional medical images. In some implementations, the predicted matching cross-sectional medical image is identified by directly comparing pixels between the cross-sectional medical image associated with the particular entry and at least some of the second plurality of cross-sectional medical images (e.g., via a pixel patch comparison, image histogram analysis, intensity similarity, etc.).

Act 4314 of flow diagram 4300 includes presenting the predicted matching cross-sectional medical image contemporaneously with presenting the cross-sectional medical image associated with the particular entry selected by the received user input. Act 4314 may be carried out using one or more components (e.g., I/O device interface(s) 106, hardware processor(s) 108, hardware storage device(s) 112, primary database 116, and/or others) of a computing system 100 or similar device. In some implementations, the predicted matching cross-sectional image may be changed or redefined based on user input received for navigating to a different cross-sectional medical image of the second plurality of cross-sectional medical images.

Act 4316 of flow diagram 4300 includes receiving user input directed to a pixel region within a matching lesion in the predicted matching cross-sectional medical image of the second plurality of cross-sectional medical images. Act 4316 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. The matching lesion may correspond to the lesion identified by the lesion marker associated with the particular entry.

Act 4318 of flow diagram 4300 includes associating a matching lesion marker with the pixel region within the matching lesion and storing the matching lesion marker in a matching entry in a second data structure. Act 4318 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. The first and second data structures may comprise different parts of the same data structure or may comprise separate data structures.

In some instances, act 4318 further includes copying the location information for the lesion associated with the particular entry from the particular entry into the matching entry (e.g., the lesion associated with the particular entry and the matching lesion may both comprise representations of the same physical lesion of the patient's body, such that location information for both the matching lesion and the lesion associated with the particular entry may be the same)

Furthermore, act 4318 may also include storing segmentation information associated with the matching lesion into matching entry of the second database. The segmentation information may include a shape associated with the matching lesion and a major axis and/or a minor axis associated with the matching lesion. In some instances, the segmentation information is obtained at least in part by a machine learning module 120.

Act 4320 of flow diagram 4300 includes generating a patient report comprising representations of information from at least the particular entry and the matching entry. Act 4320 may be carried out using one or more components (e.g., I/O device interface(s) 106, hardware processor(s) 108, image processing module(s) 110, hardware storage device(s) 112, data processing module(s) 114, primary database 116, machine learning module(s) 120, and/or others) of a computing system 100 or similar device. The patient report may comprise any lesion information stored within the first data structure and/or the second data structure. In some instances, the patient report comprises an image of the lesion associated with the particular entry and the matching lesion.

Additional Details Concerning Computing Systems

As noted above, a computing system 100 may include and/or be used to perform any of the operations described herein. Computing system 100 may take various different forms. For example, computing system 100 may be embodied as a tablet, a desktop, a laptop, a mobile device, a cloud device, a head-mounted display, or a standalone device. Computing system 100 may also be a distributed system that includes one or more connected computing components/devices that are in communication with computing system 100.

Regarding the hardware processor(s) 108, it will be appreciated that the functionality described herein can be performed, at least in part, by one or more hardware logic components (e.g., the processor(s) 108). That is, any of the disclosed method acts and/or operations may be performed by the processor(s) 108. Illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

Hardware storage device(s) 112 may be physical system memory, which may be volatile, non-volatile, or some combination of the two. The term "memory" may also be used herein to refer to non-volatile mass storage such as physical storage media. If computing system 100 is distributed, the processing, memory, and/or storage capability may be distributed as well.

The disclosed embodiments may comprise or utilize a special-purpose or general-purpose computer including computer hardware, such as, for example, one or more processors (such as hardware processor(s) 108) and system memory (such as hardware storage device(s) 112), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Computer-readable media that carry computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computing system 100 may also be connected (via a wired or wireless connection) to external sensors (e.g., one or more remote radiologic devices 104) or devices via a network 128. For example, computing system 100 can communicate with any number devices or cloud services to obtain or process data. In some cases, network 128 may itself be a cloud network. Furthermore, computing system 100 may also be connected through one or more wired or wireless networks 128 to remote/separate computer systems(s) that are configured to perform any of the processing described with regard to computing system 100.

A "network," like network 128, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computing system 100 will include one or more communication channels that are used to communicate with the network 128. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

I claim:

1. A system for analyzing lesions in cross-sectional medical images, comprising:
   one or more processors; and
   one or more hardware storage devices storing computer-executable instructions that are executable by the one or more processors to configure the system to:
      identify a user profile associated with a user accessing the system, the user profile indicating a radiology specialty associated with the user;
      access a plurality of cross-sectional medical images associated with a particular patient;
      identify a subset of cross-sectional medical images from the plurality of cross-sectional medical images that correspond to the radiology specialty indicated by the user profile;
      present the subset of cross-sectional medical images to the user in navigable form;
      receive user input that configures the system to mark, segment, or label a lesion represented in a cross-sectional medical image of the subset of cross-sectional medical images;
      store a subspecialty report comprising information associated with the marking, segmenting, or labeling;

determine that marking, segmentation, or labeling has been performed for each radiology specialty that corresponds to a subset of cross-sectional medical images from the plurality of cross-sectional medical images associated with the particular patient; and in response to so determining, generate or update a composite report comprising marking, segmentation, or labeling information for each cross-sectional medical image of the plurality of cross-sectional medical images associated with the particular patient that includes marking, segmentation, or labeling.

2. The system of claim 1, wherein the radiology specialty is a radiology subspecialty comprising any of: neuroradiology or body radiology, wherein body radiology comprises chest and/or abdomen subspecialties.

3. The system of claim 1, wherein identifying the subset of cross-sectional medical images that are associated with the radiology specialty indicated by the user profile is based on metadata associated with one or more of the cross-sectional medical images of the plurality of cross-sectional medical images.

4. The system of claim 1, wherein the computer-executable instructions are executable to configure the system to:
prompt, at a user device, the user to provide user input to associate one or more cross-sectional medical images within the plurality of cross-sectional medical images with one or more radiology specialties; and
store metadata for each of the one or more cross-sectional medical images, the metadata indicating the corresponding radiology specialty.

5. The system of claim 1, wherein the computer-executable instructions are executable to configure the system to render one or more representations of a selection of the subset of cross-sectional medical images that include a marked lesion.

6. The system of claim 5, wherein the computer-executable instructions are executable to configure the system to receive user input selecting:
a representation of the one or more representations of the selection of the subset of cross-sectional medical images that include a marked lesion; or
a control for navigating to a next cross-sectional medical image within the selection of the subset of cross-sectional medical images that include a marked lesion.

7. The system of claim 6, wherein the computer-executable instructions are executable to configure the system to navigate to and display:
the cross-sectional medical image and the marked lesion that correspond to the representation of the one or more representations selected by the user; or
the next cross-sectional medical image and a next marked lesion in response to receiving user input selecting the control for navigating to the next cross-sectional image within the selection of the subset of cross-sectional medical images that include a marked lesion.

8. The system of claim 1, wherein the segmentation or labeling is performed at least in part utilizing machine learning.

9. The system of claim 1, wherein the subspecialty report includes a view of the lesion.

10. The system of claim 1, wherein the computer-executable instructions are executable to configure the system to:
determine that marking, segmentation, or labeling has not been performed for each radiology specialty that corresponds to a subset of cross-sectional medical images from the plurality of cross-sectional medical images associated with the particular patient; and in response to so determining, refrain from generating or updating a composite report comprising marking, segmentation, or labeling information for each cross-sectional medical image of the plurality of cross-sectional medical images associated with the particular patient that includes marking, segmentation, or labeling.

11. A method for analyzing lesions in cross-sectional medical images, comprising:
identifying a user profile associated with a user accessing a system, the user profile indicating a radiology specialty associated with the user;
accessing a plurality of cross-sectional medical images associated with a particular patient;
identifying a subset of cross-sectional medical images from the plurality of cross-sectional medical images that correspond to the radiology specialty indicated by the user profile; and
presenting the subset of cross-sectional medical images to the user in navigable form;
receiving user input that configures the system to mark, segment, or label a lesion represented in a cross-sectional medical image of the subset of cross-sectional medical images;
storing a subspecialty report comprising information associated with the marking, segmenting, or labeling;
determining that marking, segmentation, or labeling has been performed for each radiology specialty that corresponds to a subset of cross-sectional medical images from the plurality of cross-sectional medical images associated with the particular patient; and
in response to so determining, generating or updating a composite report comprising marking, segmentation, or labeling information for each cross-sectional medical image of the plurality of cross-sectional medical images associated with the particular patient that includes marking, segmentation, or labeling.

12. The method of claim 11, wherein the radiology specialty is a radiology subspecialty comprising any of: neuroradiology or body radiology, wherein body radiology comprises chest and/or abdomen subspecialties.

13. The method of claim 11, wherein identifying the subset of cross-sectional medical images that are associated with the radiology specialty indicated by the user profile is based on metadata associated with one or more of the cross-sectional medical images of the plurality of cross-sectional medical images.

14. The method of claim 11, further comprising:
prompting, at a user device, the user to provide user input to associate one or more cross-sectional medical images within the plurality of cross-sectional medical images with one or more radiology specialties; and
storing metadata for each of the one or more cross-sectional medical images, the metadata indicating the corresponding radiology specialty.

15. The method of claim 11, further comprising:
determining that marking, segmentation, or labeling has not been performed for each radiology specialty that corresponds to a subset of cross-sectional medical images from the plurality of cross-sectional medical images associated with the particular patient; and
in response to so determining, refraining from generating or updating a composite report comprising marking, segmentation, or labeling information for each cross-sectional medical image of the plurality of cross-sectional medical images associated with the particular patient that includes marking, segmentation, or labeling.

16. A system for analyzing cross-sectional medical images, comprising:
- one or more processors; and
- one or more hardware storage devices storing computer-executable instructions that are executable by the one or more processors to configure the system to:
  - access a plurality of cross-sectional medical images associated with a particular patient;
  - present the cross-sectional medical images or a subset thereof to the user in navigable form;
  - receive user input that configures the system to mark, segment, or label a cross-sectional medical image of the cross-sectional medical images;
  - store a first subspecialty report comprising information associated with the marking, segmenting, or labeling;
  - determine that a second subspecialty report comprising marking, segmentation, or labeling of a cross-sectional image has been generated for at least one additional radiology specialty that corresponds to the cross-sectional medical images or a subset thereof; and
  - in response to so determining, generate or update a composite report comprising the marking, segmentation, or labeling information associated with the first subspecialty report and the second subspecialty report.

17. The system of claim 16, wherein the first subspecialty is a radiology subspecialty comprising any of: neuroradiology or body radiology, wherein body radiology comprises chest and/or abdomen subspecialties.

18. The system of claim 16, further comprising identifying a subset of the cross-sectional medical images associated with the first subspecialty and presenting the subset to the user, wherein identifying the subset of cross-sectional medical images that are associated with the first subspecialty is based on metadata associated with one or more of the cross-sectional medical images of the plurality of cross-sectional medical images.

19. The system of claim 16, wherein the computer-executable instructions are executable to configure the system to:
- prompt, at a user device, the user to provide user input to associate one or more cross-sectional medical images within the plurality of cross-sectional medical images with one or more radiology specialties; and
- store metadata for each of the one or more cross-sectional medical images, the metadata indicating the corresponding radiology specialty.

20. The system of claim 16, wherein the computer-executable instructions are executable to configure the system to render one or more representations of a selection of a subset of cross-sectional medical images that include a marked lesion.

21. The system of claim 16, wherein the first subspecialty report includes a view of a lesion.

22. A system for analyzing cross-sectional medical images, comprising:
- one or more processors; and
- one or more hardware storage devices storing computer-executable instructions that are executable by the one or more processors to configure the system to:
  - access a plurality of cross-sectional medical images associated with a particular patient;
  - identify a subset of cross-sectional medical images from the plurality of cross-sectional medical images that correspond to a first radiology specialty;
  - present the subset of cross-sectional medical images to the user in navigable form;
  - receive user input that configures the system to mark, segment, or label a cross-sectional medical image of the subset of cross-sectional medical images;
  - store a first subspecialty report comprising information associated with the marking, segmenting, or labeling;
  - determine that a second subspecialty report comprising marking, segmentation, or labeling of a cross-sectional image has been generated for at least one additional radiology specialty that corresponds to a subset of cross-sectional medical images from the plurality of cross-sectional medical images associated with the particular patient; and
  - in response to so determining, generate or update a composite report comprising the marking, segmentation, or labeling information associated with the first subspecialty report and the second subspecialty report.

* * * * *